US008603490B2

(12) United States Patent
Ruprecht

(10) Patent No.: US 8,603,490 B2
(45) Date of Patent: Dec. 10, 2013

(54) MODIFIED HUMAN IMMUNODEFICIENCY VIRUS CLADE C ENVELOPE POLYPEPTIDES OBTAINED FROM A ZAMBIAN ISOLATE

(75) Inventor: Ruth M. Ruprecht, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 823 days.

(21) Appl. No.: 12/286,159

(22) Filed: Sep. 29, 2008

(65) Prior Publication Data

US 2010/0092513 A1 Apr. 15, 2010

Related U.S. Application Data

(63) Continuation of application No. PCT/US2007/007774, filed on Mar. 28, 2007.

(60) Provisional application No. 60/787,270, filed on Mar. 29, 2006.

(51) Int. Cl.
A61K 39/21 (2006.01)
C07H 21/04 (2006.01)

(52) U.S. Cl.
USPC .................. 424/208.1; 424/199.1; 536/23.72

(58) Field of Classification Search
None
See application file for complete search history.

(56) References Cited

U.S. PATENT DOCUMENTS 5,792,459 A * 8/1998 Haigwood ................ 424/188.1

FOREIGN PATENT DOCUMENTS

WO 2005/028625 A2 3/2005

OTHER PUBLICATIONS

Lian, Y., et al., 2005, Evaluation of envelope vaccines derived from the South African subtype C human immunodeficiency virus type 1 TV1 strain, J. Virol. 79(21):13338-13349.*

Ndung'u, T., et al., 2001, Construction and analysis of an infectious human immunodeficiency virus type 1 subtype C molecular clone, J. Virol. 75(11):4964-4972.*

Liu, Y., et al., 2006, Selection on the human immunodeficiency virus type 1 proteome following primary infection, J. Virol. 80(19):9519-9529.*

Kassa, A., et al., 2009, Transitions to and from the CD4-bound conformation are modulated by a single-residue change in the human immunodeficiency virus type 1 gp120 inner domain, J. Virol. 83(17):8364-8378.*

Duenas-Decamp, M. J., 2009, Determinants flanking the CD4 binding loop modulate macrophage tropism of human immunodeficiency virus type 1 R5 envelopes, J. Virol. 83(6):2575-2583.*

Lee, S.-K., et al., 2000, A single point mutation in HIV-1 V3 loop alters the immunogenic properties of rgp120, Arch. Virol. 145:2087-2103.*

Desrosiers, R. C., Mar. 2004, Prospects for an AIDS vaccine, Nat. Med. 10(3):221-223.*

Gallo, R. C., 2005, The end or the beginning of the drive to an HIV-preventive vaccine: a view from over 20 years, The Lancet 366:1894-1898.*

Walker, B. D., and D. R. Burton, May 2008, Toward an AIDS vaccine, Science 320:760-764.*

Davis, H. L., May/Jun. 2008, Novel vaccines and adjuvant systems, Human Vaccines 4(3):246-250.*

Bures et al., Journal of Virology, 76(5):2233-2244 (2002).

Song et al., Journal of Virology, 80(17):8729-8738 (2006).

Lian Y et al., Evaluation of Envelope Vaccines Derived from the South African Subtype C Human Immunodeficiency Virus Type 1 TV1 Strain. J. Virology, Nov. 2005, vol. 79, pp. 13338-13349.

Wyatt R et al., Functional and Immunologic Characterization of Human Immunodeficiency Virus Type 1 Envelope Glycoproteins Containing Deletions of the Major Variable Regions. J Virology, Aug. 1993, vol. 67, pp. 4557-4565.

Office Action from Canadian Patent Application No. 2,648,086, mailed on Nov. 30, 2011.

* cited by examiner

*Primary Examiner* — Jeffrey S. Parkin
(74) *Attorney, Agent, or Firm* — Edwards Wildman Palmer LLP; Peter F. Corless

(57) ABSTRACT

The invention provides methods and compositions for raising an immune response in a subject by administering an HIV antigen. The HIV antigens include HIV clade C polynucleotides and polypeptides. The invention also provides for recombinant HIV viral particles and compositions.

12 Claims, 40 Drawing Sheets

PRETTYBOX of: aa2.msf(*) February 9, 2006 11:32:04.33

```
1157ipenvd123-codon-op   E R E K R A V G I G   A V F L G F L G A A   G S T M G A A S I T   L T V Q A R Q L L S   G I V Q Q Q D N L L   443
157ipenvd1234-codon-op   E R E K R A V G I G   A V F L G F L G A A   G S T M G A A S I T   L T V Q A R Q L L S   G I V Q Q Q D N L L   422
iv-1157ip-env-codon-op   E R E K R A V G I G   A V F L G F L G A A   G S T M G A A S I T   L T V Q A R Q L L S   G I V Q Q Q D N L L   548
  hiv1084ienv-codon-op   E R G K R A V G I G   A L F L G F L G A A   G S T M G A A S L T   L T V Q A R Q L L S   G I V Q Q Q N N L L   532

             Consensus   E R - K R A V G I G   A - F L G F L G A A   G S T M G A A S - T   L T V Q A R Q L L S   G I V Q Q Q - N L L   550

1157ipenvd123-codon-op   R A I E A Q Q H M L   Q L T V W G I K Q L   Q A R V L A I E R Y   L Q D Q Q L L G I W   G C S G K L I C T T   493
157ipenvd1234-codon-op   R A I E A Q Q H M L   Q L T V W G I K Q L   Q A R V L A I E R Y   L Q D Q Q L L G I W   G C S G K L I C T T   472
iv-1157ip-env-codon-op   R A I E A Q Q H M L   Q L T V W G I K Q L   Q A R V L A I E R Y   L Q D Q Q L L G I W   G C S G K L I C T T   598
  hiv1084ienv-codon-op   R A I E A Q Q H M L   Q L T V W G I K Q L   Q A R V L A I E R Y   L Q D Q Q L L G I W   G C S G K L I C T T   582

             Consensus   R A I E A Q Q H M L   Q L T V W G I K Q L   Q A R V L A I E R Y   L Q D Q Q L L G I W   G C S G K L I C T T   600

1157ipenvd123-codon-op   A V P W N A S W S N   K S Q T D I W E N M   T W M Q W D K E I S   K H T D T I Y R L L   E D S Q N Q Q E K N   543
157ipenvd1234-codon-op   A V P W N A S W S N   K S Q T D I W E N M   T W M Q W D K E I S   K H T D T I Y R L L   E D S Q N Q Q E K N   522
iv-1157ip-env-codon-op   A V P W N A S W S N   K S Q T D I W E N M   T W M Q W D K E I S   K H T D T I Y R L L   E D S Q N Q Q E K N   648
  hiv1084ienv-codon-op   D V P W N S S W S S   K S Y E D I W T N M   T W M Q W D K E I N   N Y T N T I Y Q L L   V D S Q T Q Q E K N   632

             Consensus   - V P W N - S W S -   K S - - D I W - N M   T W M Q W D K E I -   - - T - T I Y - L L   - D S Q - Q Q E K N   650

1157ipenvd123-codon-op   E K D L L A L D S W   E N L W N W F S I T   K W L W Y I K I F I   M I V G G L I G L R   I I F A V L S I V S   593
157ipenvd1234-codon-op   E K D L L A L D S W   E N L W N W F S I T   K W L W Y I K I F I   M I V G G L I G L R   I I F A V L S I V S   572
iv-1157ip-env-codon-op   E K D L L A L D S W   E N L W N W F S I T   K W L W Y I K I F I   M I V G G L I G L R   I I F A V L S I V S   698
  hiv1084ienv-codon-op   E K E L L A L D S W   K N L W N W F N I T   N W L W Y I K I F I   M I V G G L I G L R   I I F A V L S M V N   682

             Consensus   E K - L L A L D S W   - N L W N W F - I T   - W L W Y I K I F I   M I V G G L I G L R   I I F A V L S - V -   700

1157ipenvd123-codon-op   R V R Q G Y S P L S   F Q T H L P T P R G   P D R P E G I E E E   G G E R D R D R S I   R L V N G S L A L I   643
157ipenvd1234-codon-op   R V R Q G Y S P L S   F Q T H L P T P R G   P D R P E G I E E E   G G E R D R D R S I   R L V N G S L A L I   622
iv-1157ip-env-codon-op   R V R Q G Y S P L S   F Q T H L P T P R G   P D R P E G I E E E   G G E R D R D R S I   R L V N G S L A L I   748
  hiv1084ienv-codon-op   R V R Q G Y S P L S   F Q T L T P N P R G   P D R L G R I E E E   G G E Q D R D R S I   R L V S G F L A L A   732
             Consensus   R V R Q G Y S P L S   F Q T - - P - P R G   P D R - - - I E E E   G G E - D R D R S I   R L V - G - L A L -   750
```

FIGURE 1 (CONTINUED)

PETTYBOX of: aa2.msf(*) February 9, 2006 11:32:04.33

```
1157ipenvd123-codon-op   WDDLRSLCLF SYHRLRDLLL IVTRIVELLG R........RG WEALKYWWNL 686
157ipenvd1234-codon-op   WDDLRSLCLF SYHRLRDLLL IVTRIVELLG R........RG WEALKYWWNL 665
iv-1157ip-env-codon-op   WDDLRSLCLF SYHRLRDLLL IVTRIVELLG R........RG WEALKYWWNL 791
hiv1084ienv-codon-op     WDDLRSLCLF SYHRLRDCIL IVARAAELLG RSSLRGLQKG WEALKYLGSL 782

Consensus                WDDLRSLCLF SYHRLRD--L IV-R--ELLG R--------G WEALKY---L 800

1157ipenvd123-codon-op   LQYWSQELKN SAVSLLNATA IAVAEGTDRV IEVVQGACRA IRHIPRRMRQ 736
157ipenvd1234-codon-op   LQYWSQELKN SAVSLLNATA IAVAEGTDRV IEVVQGACRA IRHIPRRMRQ 715
iv-1157ip-env-codon-op   LQYWSQELKN SAVSLLNATA IAVAEGTDRV IEVVQGACRA IRHIPRRMRQ 841
hiv1084ienv-codon-op     VQYWGLELKK SAVSLLDTTA IAVAEGTDRV IELVQRICRA ICNIPRRIRQ 832

Consensus                -QYW--ELK- SAVSLL--TA IAVAEGTDRV IE-VQ--CRA I--IPRR-RQ 850

1157ipenvd123-codon-op   GLERILL* 743
157ipenvd1234-codon-op   GLERILL* 722
iv-1157ip-env-codon-op   GLERILL* 848
hiv1084ienv-codon-op     GFEAALQ* 839

Consensus                G-E--L-- 858
```

FIGURE 1 (CONTINUED)

```
                                   1                                                    50
   dna2.msf{1157ipenvd123-codon-op}  ~~~~~~~~~~ ~~~~~~~~~~ ~~~~~~~~~~ ~~~~~~~~~~ ~~~~~~~~~~
  dna2.msf{1157ipenvd1234-codon-op}  ~~~~~~~~~~ ~~~~~~~~~~ ~~~~~~~~~~ ~~~~~~~~~~ ~~~~~~~~~~
dna2.msf{shiv-1157ip-env-codon-op}  atgcgcgtga aggagaagta ccagcacctg tggcgctggg gctggcgctg
    dna2.msf{hiv1084ienv-codon-op}  ~~~~~~~~~a tgcgcgtgcg cggcatccag cgcaactacc cccagtggtg
                         Consensus  ---------- ---------- ---------- ---------- ----------

                                   51                                                  100
   dna2.msf{1157ipenvd123-codon-op}  ~~~~~~~~~~ ~~~~~~~~~~ ~~~~~~~~~~ ~~~~~~~~~~ ~~~~~~~~~~
  dna2.msf{1157ipenvd1234-codon-op}  ~~~~~~~~~~ ~~~~~~~~~~ ~~~~~~~~~~ ~~~~~~~~~~ ~~~~~~~~~~
dna2.msf{shiv-1157ip-env-codon-op}  gggcaccatg ctgctgggca tgctgatgat ctgctccgcc accgagaagc
    dna2.msf{hiv1084ienv-codon-op}  gatctggggc atcctgggct tcctgatgat ctacaacggc atgggctccc
                         Consensus  ---------- ---------- ---------- ---------- ----------

                                   101                                                 150
   dna2.msf{1157ipenvd123-codon-op}  ~~~~~~~~~~ ~~~~~~~~~~ ~~~~~~~~~~ ~~~~~~~~~~ ~~~~~~~~~~
  dna2.msf{1157ipenvd1234-codon-op}  ~~~~~~~~~~ ~~~~~~~~~~ ~~~~~~~~~~ ~~~~~~~~~~ ~~~~~~~~~~
dna2.msf{shiv-1157ip-env-codon-op}  tgtgggtgac cgtgtactac ggcgtgcccg tgtggaagga ggccaagacc
    dna2.msf{hiv1084ienv-codon-op}  tgtgggtgac cgtgtactac ggcgtgcccg tgtggaagga ggccaagacc
                         Consensus  ---------- ---------- ---------- ---------- ----------

                                   151                                                 200
   dna2.msf{1157ipenvd123-codon-op}  ~~~~~~~~~~ ~~~~~~~~~~ ~~~~~~~~~~ ~~~~~~~~~~ ~~~~~~~~~~
  dna2.msf{1157ipenvd1234-codon-op}  ~~~~~~~~~~ ~~~~~~~~~~ ~~~~~~~~~~ ~~~~~~~~~~ ~~~~~~~~~~
dna2.msf{shiv-1157ip-env-codon-op}  accctgttct gcgcctccga cgccaaggcc tacgagaagg aggtgcacaa
    dna2.msf{hiv1084ienv-codon-op}  accctgttct gcgcctccga cgccaaggcc tacgagcgcg aggtgcacaa
                         Consensus  ---------- ---------- ---------- ---------- ----------

                                   201                                                 250
   dna2.msf{1157ipenvd123-codon-op}  ~~~~~~~~~~ ~~~~~~~~~~ ~~~~~~~~~~ ~~~~atgcgC gtgaAGGAGa
  dna2.msf{1157ipenvd1234-codon-op}  ~~~~~~~~~~ ~~~~~~~~~~ ~~~~~~~~~~ ~~~~atgcgC gtgaAGGAGa
dna2.msf{shiv-1157ip-env-codon-op}  catctgggcc acccacgcct gcgtgcccac cgaccccaaC ccccAGGAGa
    dna2.msf{hiv1084ienv-codon-op}  catctgggcc acccacgcct gcgtgcccac cgaccccaaC ccccAGGAGc
                         Consensus  ---------- ---------- ---------- ---------C ----AGGAG-
```

FIGURE 2

```
                                      251                                                    300
   dna2.msf{1157ipenvd123-codon-op}   agtacCaGcA cctgtgGcgC tgGggCTggc gCtgGgGcac catgctgcTG
  dna2.msf{1157ipenvd1234-codon-op}   agtacCaGcA cctgtgGcgC tgGggCTggc gCtgGgGcac catgctgcTG
 dna2.msf{shiv-1157ip-env-codon-op}   tcgtgCtGgA gaacgtGacC gaGaaCTtca aCatGtGgaa ggacgacaTG
   dna2.msf{hiv1084ienv-codon-op}     tggtgCtGgA gaacgtGacC gaGaaCTtca aCatGtGgga gaacgacaTG
                         Consensus    -----C-G-A ------G--C --G--CT--- -C--G-G--- --------TG

                                      301                                                    350
   dna2.msf{1157ipenvd123-codon-op}   GgcatgCtGA TGatCtgctc CgcCAcCgag aaGctGtggg tGaCCgTGtA
  dna2.msf{1157ipenvd1234-codon-op}   GgcatgCtGA TGatCtgctc CgcCAcCgag aaGctGtggg tGaCCgTGtA
 dna2.msf{shiv-1157ip-env-codon-op}   GtggacCaGA TGcaCgagga CatCAtCtcc ctGtgGgacc aGtCCcTGaA
   dna2.msf{hiv1084ienv-codon-op}     GtggacCaGA TGcaCgagga CatCAtCtcc ctGtgGgacc aGtCCcTGaA
                         Consensus    G-----C-GA TG--C----- C--CA-C--- --G--G---- -G-CC-TG-A

                                      351                                                    400
   dna2.msf{1157ipenvd123-codon-op}   ctaCgGCGTG cccgTGtgga aggaGgcCaa GACCaccctg TtctgcgcCt
  dna2.msf{1157ipenvd1234-codon-op}   ctaCgGCGTG cccgTGtgga aggaGgcCaa GACCaccctg TtctgcgcCt
 dna2.msf{shiv-1157ip-env-codon-op}   gccCtGCGTG aagcTGaccc ccctGtgCgt GACCctgaag TgctccaaCt
   dna2.msf{hiv1084ienv-codon-op}     gccCtGCGTG aagcTGaccc ccctGtgCgt GACCctgaac Tg......Ca
                         Consensus    ---C-GCGTG ----TG---- ----G--C-- GACC------ T-------C-

                                      401                                                    450
   dna2.msf{1157ipenvd123-codon-op}   cCgaCgccaA GgcCtaCgag aaggaggtgc AcaAcATctg ggccacccac
  dna2.msf{1157ipenvd1234-codon-op}   cCgaCgccaA GgcCtaCgag aaggaggtgc AcaAcATctg ggccacccac
 dna2.msf{shiv-1157ip-env-codon-op}   tCacCcgcgA GggCaaCgtg acctacaagg AggAgATgga caaggtgaag
   dna2.msf{hiv1084ienv-codon-op}     cCgaCgtgaA GtcCgcCaac tccacctccg AggAcATgcg caactgctcc
                         Consensus    -C--C----A G--C--C--- ---------- A--A-AT--- ----------

                                      451                                                    500
   dna2.msf{1157ipenvd123-codon-op}   gcCtgCgtgc cCAcCGaccc CAacccCcag gagatcgtGc tGgAGaacgT
  dna2.msf{1157ipenvd1234-codon-op}   gcCtgCgtgc cCAcCGaccc CAacccCcag gagatcgtGc tGgAGaacgT
 dna2.msf{shiv-1157ip-env-codon-op}   aaCtgCtcct tCAaCGtgac CAccggCatc cgcgacaaGa aGcAGaaggT
   dna2.msf{hiv1084ienv-codon-op}     ttCaaCgtga cCAcCGagat CAaggaCcgc aagaagctGg aGcAGgcccT
                         Consensus    --C--C---- -CA-CG---- CA----C--- --------G- -G-AG----T
```

FIGURE 2 (CONTINUED)

```
                                    501                                                  550
   dna2.msf{1157ipenvd123-codon-op}  GacCgagaac tTcaACatgt gGaaggacga CatggtGgAC cagatgcaCg
  dna2.msf{1157ipenvd1234-codon-op}  GacCgagaac tTcaACatgt gGaaggacga CatggtGgAC cagatgcaCg
 dna2.msf{shiv-1157ip-env-codon-op}  GaaCgccctg tTctACcgcc tGgacatcac CccoctGgAC gagaacaaCa
    dna2.msf{hiv1084ienv-codon-op}   GttCtaccgc cTggACatcg tG......cc CctgaaGaAC tcctcctcCt
                         Consensus   G--C------ -T--AC---- -G-------- C-----G-AC --------C-

                                    551                                                  600
   dna2.msf{1157ipenvd123-codon-op}  aggACatCat CtccctgtGg gaccagtcCc tgAAgcCCTg CgtgggcgCC
  dna2.msf{1157ipenvd1234-codon-op}  aggACatCat CtccctgtGg gaccagtcCc tgAAgcCCTg CgtgggcgCC
 dna2.msf{shiv-1157ip-env-codon-op}  acaACtcCtc CgagtaccGc ttgatcaaCt gcAAgtCCTc CaccatcaCC
    dna2.msf{hiv1084ienv-codon-op}   ccaACttCtc CgagtaccGc ctgatcaaCt gcAAcaCCTc CaccgtgtCC
                         Consensus   ---AC--C-- C-------G- --------C- --AA--CCT- C-------CC

                                    601                                                  650
   dna2.msf{1157ipenvd123-codon-op}  ggcGCCTGCC CCAAGGTGAA CTTCGACCCC ATCCCCATCC ACTACTGCGC
  dna2.msf{1157ipenvd1234-codon-op}  ggcGCCTGCC CCAAGGTGAA CTTCGACCCC ATCCCCATCC ACTACTGCGC
 dna2.msf{shiv-1157ip-env-codon-op}  cagGCCTGCC CCAAGGTGAA CTTCGACCCC ATCCCCATCC ACTACTGCGC
    dna2.msf{hiv1084ienv-codon-op}   cagGCCTGCC CCAAGGTGAA CTTCGACCCC ATCCCCATCC ACTACTGCGC
                         Consensus   ---GCCTGCC CCAAGGTGAA CTTCGACCCC ATCCCCATCC ACTACTGCGC

                                    651                                                  700
   dna2.msf{1157ipenvd123-codon-op}  CCCCGCCGGC TACGCCATCC TGAAGTGCAA CAACAAGACC TTCAACGGCa
  dna2.msf{1157ipenvd1234-codon-op}  CCCCGCCGGC TACGCCATCC TGAAGTGCAA CAACAAGACC TTCAACGGCa
 dna2.msf{shiv-1157ip-env-codon-op}  CCCCGCCGGC TACGCCATCC TGAAGTGCAA CAACAAGACC TTCAACGGCa
    dna2.msf{hiv1084ienv-codon-op}   CCCCGCCGGC TACGCCATCC TGAAGTGCAA CAACAAGACC TTCAACGGCt
                         Consensus   CCCCGCCGGC TACGCCATCC TGAAGTGCAA CAACAAGACC TTCAACGGC-

                                    701                                                  750
   dna2.msf{1157ipenvd123-codon-op}  CCGGCCCCTG CcACAACGTG TCCACCGTGC AGTGCACCCA CGGCATCAAG
  dna2.msf{1157ipenvd1234-codon-op}  CCGGCCCCTG CcACAACGTG TCCACCGTGC AGTGCACCCA CGGCATCAAG
 dna2.msf{shiv-1157ip-env-codon-op}  CCGGCCCCTG CcACAACGTG TCCACCGTGC AGTGCACCCA CGGCATCAAG
    dna2.msf{hiv1084ienv-codon-op}   CCGGCCCCTG CaACAACGTG TCCACCGTGC AGTGCACCCA CGGCATCAAG
                         Consensus   CCGGCCCCTG C-ACAACGTG TCCACCGTGC AGTGCACCCA CGGCATCAAG
```

FIGURE 2 (CONTINUED)

```
                                    751                                                   800
 dna2.msf{1157ipenvd123-codon-op}   CCCGTGGTGT CCACCCAGCT GCTGCTGAAC GGCTCCCTGG CCGAGcgcGA
 dna2.msf{1157ipenvd1234-codon-op}  CCCGTGGTGT CCACCCAGCT GCTGCTGAAC GGCTCCCTGG CCGAGcgcGA
 dna2.msf{shiv-1157ip-env-codon-op} CCCGTGGTGT CCACCCAGCT GCTGCTGAAC GGCTCCCTGG CCGAGcgcGA
 dna2.msf{hiv1084ienv-codon-op}     CCCGTGGTGT CCACCCAGCT GCTGCTGAAC GGCTCCCTGG CCGAGgagGA
                         Consensus  CCCGTGGTGT CCACCCAGCT GCTGCTGAAC GGCTCCCTGG CCGAG---GA

                                    801                                                850
 dna2.msf{1157ipenvd123-codon-op}   gATCATCATC CGCTCCGAGA ACCTGACCgA CAACGTGAAG ACCATCATCG
 dna2.msf{1157ipenvd1234-codon-op}  gATCATCATC CGCTCCGAGA ACCTGACCgA CAACGTGAAG ACCATCATCG
 dna2.msf{shiv-1157ip-env-codon-op} gATCATCATC CGCTCCGAGA ACCTGACCgA CAACGTGAAG ACCATCATCG
 dna2.msf{hiv1084ienv-codon-op}     cATCATCATC CGCTCCGAGA ACCTGACCaA CAACGTGAAG ACCATCATCG
                         Consensus  -ATCATCATC CGCTCCGAGA ACCTGACC-A CAACGTGAAG ACCATCATCG

                                    851                                                900
 dna2.msf{1157ipenvd123-codon-op}   TGCACtTcAA cGAgTcCGTG gAGATCaacT GCACCgGCgC CggC......
 dna2.msf{1157ipenvd1234-codon-op}  TGCACtTcAA cGAgTcCGTG gAGATCaacT GCACCgGCgC CggC......
 dna2.msf{shiv-1157ip-env-codon-op} TGCACtTcAA cGAgTcCGTG gAGATCaacT GCACCcGCcC CaaCaacaac
 dna2.msf{hiv1084ienv-codon-op}     TGCACcTgAA gGAcTaCGTG aAGATCgtgT GCACCcGCcC CaaCaacaac
                         Consensus  TGCAC-T-AA -GA-T-CGTG -AGATC---T GCACC-GC-C C--C------

                                    901                                                950
 dna2.msf{1157ipenvd123-codon-op}   .......... .......... .......... .......... ..........
 dna2.msf{1157ipenvd1234-codon-op}  .......... .......... .......... .......... ..........
 dna2.msf{shiv-1157ip-env-codon-op} acccgcaagt ccatccgcat cggccccggc caggccttct acgccaccgg
 dna2.msf{hiv1084ienv-codon-op}     acccgcaagt ccatgcgcat cggccccggc caggccttct acgccaccgg
                         Consensus  ---------- ---------- ---------- ---------- ----------

                                    951                                               1000
 dna2.msf{1157ipenvd123-codon-op}   .......... .......... .....GCCCA CTGCAACATC TCCaaggagA
 dna2.msf{1157ipenvd1234-codon-op}  .......... .......... .....GCCCA CTGCAACATC TCCaaggagA
 dna2.msf{shiv-1157ip-env-codon-op} cgacatcatc ggcgacatcc gccagGCCCA CTGCAACATC TCCaaggagA
 dna2.msf{hiv1084ienv-codon-op}     cgagatcatc ggcaacatcc gcgagGCCCA CTGCAACATC TCCggctccA
                         Consensus  ---------- ---------- -----GCCCA CTGCAACATC TCC------A
```

FIGURE 2 (CONTINUED)

```
                                     1001                                                  1050
  dna2.msf{1157ipenvd123-codon-op}   AcTGGAACAA gACCCTGCAG tGgGTGcgcg gcAAGCTGGa gGAGCACTTC
 dna2.msf{1157ipenvd1234-codon-op}   AcTGGAACAA gACCCTGCAG tGgGTGcgcg gcAAGCTGGa gGAGCACTTC
dna2.msf{shiv-1157ip-env-codon-op}   AcTGGAACAA gACCCTGCAG tGgGTGcgcg gcAAGCTGGa gGAGCACTTC
  dna2.msf{hiv1084ienv-codon-op}     AgTGGAACAA cACCCTGCAG cGcGTGaaga agAAGCTGGg cGAGCACTTC
                       Consensus     A-TGGAACAA -ACCCTGCAG -G-GTG---- --AAGCTGG- -GAGCACTTC

                                     1051                                                  1100
  dna2.msf{1157ipenvd123-codon-op}   CCCAACAA.. .gACCATCGt gTTCAAGCCC TCCTCCGGCG GCGACCTGGA
 dna2.msf{1157ipenvd1234-codon-op}   CCCAACAA.. .gACCATCGt gTTCAAGCCC TCCTCCGGCG GCGACCTGGA
dna2.msf{shiv-1157ip-env-codon-op}   CCCAACAA.. .gACCATCGt gTTCAAGCCC TCCTCCGGCG GCGACCTGGA
  dna2.msf{hiv1084ienv-codon-op}     CCCAACAAca ccACCATCGa cTTCAAGCCC TCCTCCGGCG GCGACCTGGA
                       Consensus     CCCAACAA-- --ACCATCG- -TTCAAGCCC TCCTCCGGCG GCGACCTGGA

                                     1101                                                  1150
  dna2.msf{1157ipenvd123-codon-op}   GATCACCACC CACTCCTTCA ACTGCCGCGG CGAGTTCTTC TACTGCAACa
 dna2.msf{1157ipenvd1234-codon-op}   GATCACCACC CACTCCTTCA ACTGCCGCGG CGAGTTCTTC TACTGCAAC.
dna2.msf{shiv-1157ip-env-codon-op}   GATCACCACC CACTCCTTCA ACTGCCGCGG CGAGTTCTTC TACTGCAACa
  dna2.msf{hiv1084ienv-codon-op}     GATCACCACC CACTCCTTCA ACTGCCGCGG CGAGTTCTTC TACTGCAACa
                       Consensus     GATCACCACC CACTCCTTCA ACTGCCGCGG CGAGTTCTTC TACTGCAAC-

                                     1151                                                  1200
  dna2.msf{1157ipenvd123-codon-op}   cctccaagct gttcaacggc accgacaact ccacccacat ggacaccggc
 dna2.msf{1157ipenvd1234-codon-op}   .......... .......... .......... .......... ..........
dna2.msf{shiv-1157ip-env-codon-op}   cctccaagct gttcaacggc accgacaact ccacccacat ggacaccggc
  dna2.msf{hiv1084ienv-codon-op}     cctccaagct gttcaacggc acctccgagt cca....... ..........
                       Consensus     ---------- ---------- ---------- ---------- ----------

                                     1201                                                  1250
  dna2.msf{1157ipenvd123-codon-op}   aacgacaccg tgatCaCCat cCCCTGCcgc ATCAAGCAGA TCATCAACAT
 dna2.msf{1157ipenvd1234-codon-op}   .......... ..ggCgCCgg cCCCTGCcgc ATCAAGCAGA TCATCAACAT
dna2.msf{shiv-1157ip-env-codon-op}   aacgacaccg tgatCaCCat cCCCTGCcgc ATCAAGCAGA TCATCAACAT
  dna2.msf{hiv1084ienv-codon-op}     ....actcca ccatCaCCct gCCCTGCaag ATCAAGCAGA TCATCAACAT
                       Consensus     ---------- ----C-CC-- -CCCTGC--- ATCAAGCAGA TCATCAACAT
```

FIGURE 2 (CONTINUED)

```
                               1251                                               1300
dna2.msf{1157ipenvd123-codon-op}   GTGGCAGGag GTGGGgCGCG CCATGTACGC CCCCCCCATC GagGGCAACA
dna2.msf{1157ipenvd1234-codon-op}  GTGGCAGGag GTGGGgCGCG CCATGTACGC CCCCCCCATC GagGGCAACA
dna2.msf{shiv-1157ip-env-codon-op} GTGGCAGGag GTGGGgCGCG CCATGTACGC CCCCCCCATC GagGGCAACA
dna2.msf{hiv1084ienv-codon-op}     GTGGCAGGgc GTGGGcCGCG CCATGTACGC CCCCCCCATC GccGGCAACA
                         Consensus GTGGCAGG-- GTGGG-CGCG CCATGTACGC CCCCCCCATC G--GGCAACA

                                   1301                                               1350
dna2.msf{1157ipenvd123-codon-op}   TCACCTGCAA GTCCAACATC ACCGGCCTGC TGCTGgtgCG CGACGGCGGC
dna2.msf{1157ipenvd1234-codon-op}  TCACCTGCAA GTCCAACATC ACCGGCCTGC TGCTGgtgCG CGACGGCGGC
dna2.msf{shiv-1157ip-env-codon-op} TCACCTGCAA GTCCAACATC ACCGGCCTGC TGCTGgtgCG CGACGGCGGC
dna2.msf{hiv1084ienv-codon-op}     TCACCTGCAA GTCCAACATC ACCGGCCTGC TGCTGaccCG CGACGGCGGC
                         Consensus TCACCTGCAA GTCCAACATC ACCGGCCTGC TGCTG---CG CGACGGCGGC

                                   1351                                               1400
dna2.msf{1157ipenvd123-codon-op}   cAggacaact cCacCAACaa CACCGAGAcC TTCCGCCCCG GCGGCGGCGA
dna2.msf{1157ipenvd1234-codon-op}  cAggacaact cCacCAACaa CACCGAGAcC TTCCGCCCCG GCGGCGGCGA
dna2.msf{shiv-1157ip-env-codon-op} cAggacaact cCacCAACaa CACCGAGAcC TTCCGCCCCG GCGGCGGCGA
dna2.msf{hiv1084ienv-codon-op}     aA........ .CggCAACgg CACCGAGAtC TTCCGCCCCG GCGGCGGCGA
                         Consensus -A-------- -C--CAAC-- CACCGAGA-C TTCCGCCCCG GCGGCGGCGA

                                   1401                                               1450
dna2.msf{1157ipenvd123-codon-op}   CATGCGCaAC AACTGGCGCT CCGAGCTGTA CAAGTACAAG GTGGTGgAGA
dna2.msf{1157ipenvd1234-codon-op}  CATGCGCaAC AACTGGCGCT CCGAGCTGTA CAAGTACAAG GTGGTGgAGA
dna2.msf{shiv-1157ip-env-codon-op} CATGCGCaAC AACTGGCGCT CCGAGCTGTA CAAGTACAAG GTGGTGgAGA
dna2.msf{hiv1084ienv-codon-op}     CATGCGCgAC AACTGGCGCT CCGAGCTGTA CAAGTACAAG GTGGTGaAGA
                         Consensus CATGCGC-AC AACTGGCGCT CCGAGCTGTA CAAGTACAAG GTGGTG-AGA

                                   1451                                               1500
dna2.msf{1157ipenvd123-codon-op}   TCaAGCCCCT GGGCATCGCC CCCACCAAGG CCAAGCGCCG CGTGGTGGAG
dna2.msf{1157ipenvd1234-codon-op}  TCaAGCCCCT GGGCATCGCC CCCACCAAGG CCAAGCGCCG CGTGGTGGAG
dna2.msf{shiv-1157ip-env-codon-op} TCaAGCCCCT GGGCATCGCC CCCACCAAGG CCAAGCGCCG CGTGGTGGAG
dna2.msf{hiv1084ienv-codon-op}     TCgAGCCCCT GGGCATCGCC CCCACCAAGG CCAAGCGCCG CGTGGTGGAG
                         Consensus TC-AGCCCCT GGGCATCGCC CCCACCAAGG CCAAGCGCCG CGTGGTGGAG
```

FIGURE 2 (CONTINUED)

```
                                   1501                                                1550
  dna2.msf{1157ipenvd123-codon-op}  CGCGagAAGC GCGCCGTGGG CATCGGCGCC gTGTTCCTGG GCTTCCTGGG
 dna2.msf{1157ipenvd1234-codon-op}  CGCGagAAGC GCGCCGTGGG CATCGGCGCC gTGTTCCTGG GCTTCCTGGG
dna2.msf{shiv-1157ip-env-codon-op}  CGCGagAAGC GCGCCGTGGG CATCGGCGCC gTGTTCCTGG GCTTCCTGGG
   dna2.msf{hiv1084ienv-codon-op}   CGCGgcAAGC GCGCCGTGGG CATCGGCGCC cTGTTCCTGG GCTTCCTGGG
                         Consensus  CGCG--AAGC GCGCCGTGGG CATCGGCGCC -TGTTCCTGG GCTTCCTGGG

                                   1551                                                1600
  dna2.msf{1157ipenvd123-codon-op}  CGCCGCCGGC TCCACCATGG GCGCCGCCTC CaTcACCCTG ACCGTGCAGG
 dna2.msf{1157ipenvd1234-codon-op}  CGCCGCCGGC TCCACCATGG GCGCCGCCTC CaTcACCCTG ACCGTGCAGG
dna2.msf{shiv-1157ip-env-codon-op}  CGCCGCCGGC TCCACCATGG GCGCCGCCTC CaTcACCCTG ACCGTGCAGG
   dna2.msf{hiv1084ienv-codon-op}   CGCCGCCGGC TCCACCATGG GCGCCGCCTC CcTgACCCTG ACCGTGCAGG
                         Consensus  CGCCGCCGGC TCCACCATGG GCGCCGCCTC C-T-ACCCTG ACCGTGCAGG

                                   1601                                                1650
  dna2.msf{1157ipenvd123-codon-op}  CCCGCCAGCT GCTGTCCGGC ATCGTGCAGC AGCAGgACAA CCTGCTGCGC
 dna2.msf{1157ipenvd1234-codon-op}  CCCGCCAGCT GCTGTCCGGC ATCGTGCAGC AGCAGgACAA CCTGCTGCGC
dna2.msf{shiv-1157ip-env-codon-op}  CCCGCCAGCT GCTGTCCGGC ATCGTGCAGC AGCAGgACAA CCTGCTGCGC
   dna2.msf{hiv1084ienv-codon-op}   CCCGCCAGCT GCTGTCCGGC ATCGTGCAGC AGCAGaACAA CCTGCTGCGC
                         Consensus  CCCGCCAGCT GCTGTCCGGC ATCGTGCAGC AGCAG-ACAA CCTGCTGCGC

                                   1651                                                1700
  dna2.msf{1157ipenvd123-codon-op}  GCCATCGAGG CCCAGCAGCA CATGCTGCAG CTGACCGTGT GGGGCATCAA
 dna2.msf{1157ipenvd1234-codon-op}  GCCATCGAGG CCCAGCAGCA CATGCTGCAG CTGACCGTGT GGGGCATCAA
dna2.msf{shiv-1157ip-env-codon-op}  GCCATCGAGG CCCAGCAGCA CATGCTGCAG CTGACCGTGT GGGGCATCAA
   dna2.msf{hiv1084ienv-codon-op}   GCCATCGAGG CCCAGCAGCA CATGCTGCAG CTGACCGTGT GGGGCATCAA
                         Consensus  GCCATCGAGG CCCAGCAGCA CATGCTGCAG CTGACCGTGT GGGGCATCAA

                                   1701                                                1750
  dna2.msf{1157ipenvd123-codon-op}  aCAGCTGCAG GCCCGCGTGC TGGCCATCGA GCGCTACCTG CAGGACCAGC
 dna2.msf{1157ipenvd1234-codon-op}  aCAGCTGCAG GCCCGCGTGC TGGCCATCGA GCGCTACCTG CAGGACCAGC
dna2.msf{shiv-1157ip-env-codon-op}  aCAGCTGCAG GCCCGCGTGC TGGCCATCGA GCGCTACCTG CAGGACCAGC
   dna2.msf{hiv1084ienv-codon-op}   gCAGCTGCAG GCCCGCGTGC TGGCCATCGA GCGCTACCTG CAGGACCAGC
                         Consensus  -CAGCTGCAG GCCCGCGTGC TGGCCATCGA GCGCTACCTG CAGGACCAGC
```

FIGURE 2 (CONTINUED)

```
                 1251                                          1300
dna2.msf{1157ipenvd123-codon-op}   GTGGCAGGag GTGGGgCGCG CCATGTACGC CCCCCCCATC GagGGCAACA
dna2.msf{1157ipenvd1234-codon-op}  GTGGCAGGag GTGGGgCGCG CCATGTACGC CCCCCCCATC GagGGCAACA
dna2.msf{shiv-1157ip-env-codon-op} GTGGCAGGag GTGGGgCGCG CCATGTACGC CCCCCCCATC GagGGCAACA
dna2.msf{hiv1084ienv-codon-op}     GTGGCAGGgc GTGGGcCGCG CCATGTACGC CCCCCCCATC GccGGCAACA
                         Consensus GTGGCAGG-- GTGGG-CGCG CCATGTACGC CCCCCCCATC G--GGCAACA

                                   1301                                              1350
dna2.msf{1157ipenvd123-codon-op}   TCACCTGCAA GTCCAACATC ACCGGCCTGC TGCTGgtgCG CGACGGCGGC
dna2.msf{1157ipenvd1234-codon-op}  TCACCTGCAA GTCCAACATC ACCGGCCTGC TGCTGgtgCG CGACGGCGGC
dna2.msf{shiv-1157ip-env-codon-op} TCACCTGCAA GTCCAACATC ACCGGCCTGC TGCTGgtgCG CGACGGCGGC
dna2.msf{hiv1084ienv-codon-op}     TCACCTGCAA GTCCAACATC ACCGGCCTGC TGCTGaccCG CGACGGCGGC
                         Consensus TCACCTGCAA GTCCAACATC ACCGGCCTGC TGCTG---CG CGACGGCGGC

                                   1351                                              1400
dna2.msf{1157ipenvd123-codon-op}   cAggacaact cCacCAACaa CACCGAGAcC TTCCGCCCCG GCGGCGGCGA
dna2.msf{1157ipenvd1234-codon-op}  cAggacaact cCacCAACaa CACCGAGAcC TTCCGCCCCG GCGGCGGCGA
dna2.msf{shiv-1157ip-env-codon-op} cAggacaact cCacCAACaa CACCGAGAcC TTCCGCCCCG GCGGCGGCGA
dna2.msf{hiv1084ienv-codon-op}     aA........ .CggCAACgg CACCGAGAtC TTCCGCCCCG GCGGCGGCGA
                         Consensus -A-------- -C--CAAC-- CACCGAGA-C TTCCGCCCCG GCGGCGGCGA

                                   1401                                              1450
dna2.msf{1157ipenvd123-codon-op}   CATGCGCaAC AACTGGCGCT CCGAGCTGTA CAAGTACAAG GTGGTGgAGA
dna2.msf{1157ipenvd1234-codon-op}  CATGCGCaAC AACTGGCGCT CCGAGCTGTA CAAGTACAAG GTGGTGgAGA
dna2.msf{shiv-1157ip-env-codon-op} CATGCGCaAC AACTGGCGCT CCGAGCTGTA CAAGTACAAG GTGGTGgAGA
dna2.msf{hiv1084ienv-codon-op}     CATGCGCgAC AACTGGCGCT CCGAGCTGTA CAAGTACAAG GTGGTGaAGA
                         Consensus CATGCGC-AC AACTGGCGCT CCGAGCTGTA CAAGTACAAG GTGGTG-AGA

                                   1451                                              1500
dna2.msf{1157ipenvd123-codon-op}   TCaAGCCCCT GGGCATCGCC CCCACCAAGG CCAAGCGCCG CGTGGTGGAG
dna2.msf{1157ipenvd1234-codon-op}  TCaAGCCCCT GGGCATCGCC CCCACCAAGG CCAAGCGCCG CGTGGTGGAG
dna2.msf{shiv-1157ip-env-codon-op} TCaAGCCCCT GGGCATCGCC CCCACCAAGG CCAAGCGCCG CGTGGTGGAG
dna2.msf{hiv1084ienv-codon-op}     TCgAGCCCCT GGGCATCGCC CCCACCAAGG CCAAGCGCCG CGTGGTGGAG
                         Consensus TC-AGCCCCT GGGCATCGCC CCCACCAAGG CCAAGCGCCG CGTGGTGGAG
```

FIGURE 2 (CONTINUED)

```
                                    1751                                                 1800
 dna2.msf{1157ipenvd123-codon-op}   AGCTGCTGGG CATCTGGGGC TGCTCCGGCA AGCTGATCTG CACCACCGcC
dna2.msf{1157ipenvd1234-codon-op}   AGCTGCTGGG CATCTGGGGC TGCTCCGGCA ACCTGATCTG CACCACCGcC
dna2.msf{shiv-1157ip-env-codon-op}  AGCTGCTGGG CATCTGGGGC TGCTCCGGCA AGCTGATCTG CACCACCGcC
   dna2.msf{hiv1084ienv-codon-op}   AGCTGCTGGG CATCTGGGGC TGCTCCGGCA AGCTGATCTG CACCACCGaC
                        Consensus   AGCTGCTGGG CATCTGGGGC TGCTCCGGCA AGCTGATCTG CACCACCG-C

                                    1801                                                 1850
 dna2.msf{1157ipenvd123-codon-op}   GTGCCCTGGA ACgCCTCCTG GTCCaaCAAG TCCcAgaccG ACATCTGGga
dna2.msf{1157ipenvd1234-codon-op}   GTGCCCTGGA ACgCCTCCTG GTCCaaCAAG TCCcAgaccG ACATCTGGga
dna2.msf{shiv-1157ip-env-codon-op}  GTGCCCTGGA ACgCCTCCTG GTCCaaCAAG TCCcAgaccG ACATCTGGga
   dna2.msf{hiv1084ienv-codon-op}   GTGCCCTGGA ACtCCTCCTG GTCCtcCAAG TCCtAcgagG ACATCTGGac
                        Consensus   GTGCCCTGGA AC-CCTCCTG GTCC--CAAG TCC-A----G ACATCTGG--

                                    1851                                                 1900
 dna2.msf{1157ipenvd123-codon-op}   gAACATGACC TGGATGCAGT GGGACAAGGA GATCtcCAAg cACACCgACA
dna2.msf{1157ipenvd1234-codon-op}   gAACATGACC TGGATGCAGT GGGACAAGGA GATCtcCAAg cACACCgACA
dna2.msf{shiv-1157ip-env-codon-op}  gAACATGACC TGGATGCAGT GGGACAAGGA GATCtcCAAg cACACCgACA
   dna2.msf{hiv1084ienv-codon-op}   cAACATGACC TGGATGCAGT GGGACAAGGA GATCaaCAAc tACACCaACA
                        Consensus   -AACATGACC TGGATGCAGT GGGACAAGGA GATC--CAA- -ACACC-ACA

                                    1901                                                 1950
 dna2.msf{1157ipenvd123-codon-op}   CCATCTACCg cCTGCTGGaG GACTCCCAGA aCCAGCAGGA GAAGAACGAG
dna2.msf{1157ipenvd1234-codon-op}   CCATCTACCg cCTGCTGGaG GACTCCCAGA aCCAGCAGGA GAAGAACGAG
dna2.msf{shiv-1157ip-env-codon-op}  CCATCTACCg cCTGCTGGaG GACTCCCAGA aCCAGCAGGA GAAGAACGAG
   dna2.msf{hiv1084ienv-codon-op}   CCATCTACCa gCTGCTGGtG GACTCCCAGA cCCAGCAGGA GAAGAACGAG
                        Consensus   CCATCTACC- -CTGCTGG-G GACTCCCAGA -CCAGCAGGA GAAGAACGAG

                                    1951                                                 2000
 dna2.msf{1157ipenvd123-codon-op}   AAGGAcCTGC TGGCCCTGGA CTCCTGGgAG AACCTGTGGA ACTGGTTCtc
dna2.msf{1157ipenvd1234-codon-op}   AAGGAcCTGC TGGCCCTGGA CTCCTGGgAG AACCTGTGGA ACTGGTTCtc
dna2.msf{shiv-1157ip-env-codon-op}  AAGGAcCTGC TGGCCCTGGA CTCCTGGgAG AACCTGTGGA ACTGGTTCtc
   dna2.msf{hiv1084ienv-codon-op}   AAGGAgCTGC TGGCCCTGGA CTCCTGGaAG AACCTGTGGA ACTGGTTCaa
                        Consensus   AAGGA-CTGC TGGCCCTGGA CTCCTGG-AG AACCTGTGGA ACTGGTTC--
```

FIGURE 2 (CONTINUED)

```
                                         2001                                                2050
    dna2.msf{1157ipenvd123-codon-op}     CATCACCAAg TGGCTGTGGT ACATCAAGAT CTTCATCATG ATCGTGGGCG
   dna2.msf{1157ipenvd1234-codon-op}     CATCACCAAg TGGCTGTGGT ACATCAAGAT CTTCATCATG ATCGTGGGCG
  dna2.msf{shiv-1157ip-env-codon-op}     CATCACCAAg TGGCTGTGGT ACATCAAGAT CTTCATCATG ATCGTGGGCG
     dna2.msf{hiv1084ienv-codon-op}      CATCACCAAc TGGCTGTGGT ACATCAAGAT CTTCATCATG ATCGTGGGCG
                          Consensus      CATCACCAA- TGGCTGTGGT ACATCAAGAT CTTCATCATG ATCGTGGGCG

                                         2051                                                2100
    dna2.msf{1157ipenvd123-codon-op}     GCCTGATCGG CCTGCGCATC ATCTTCGCCG TGCTGTCCAT cGTGtcCCGC
   dna2.msf{1157ipenvd1234-codon-op}     GCCTGATCGG CCTGCGCATC ATCTTCGCCG TGCTGTCCAT cGTGtcCCGC
  dna2.msf{shiv-1157ip-env-codon-op}     GCCTGATCGG CCTGCGCATC ATCTTCGCCG TGCTGTCCAT cGTGtcCCGC
     dna2.msf{hiv1084ienv-codon-op}      GCCTGATCGG CCTGCGCATC ATCTTCGCCG TGCTGTCCAT gGTGaaCCGC
                          Consensus      GCCTGATCGG CCTGCGCATC ATCTTCGCCG TGCTGTCCAT -GTG--CCGC

                                         2101                                                2150
    dna2.msf{1157ipenvd123-codon-op}     GTGCGCCAGG GCTACTCCCC CCTGTCCTTC CAGACCCacc tgCCCAcCCC
   dna2.msf{1157ipenvd1234-codon-op}     GTGCGCCAGG GCTACTCCCC CCTGTCCTTC CAGACCCacc tgCCCAcCCC
  dna2.msf{shiv-1157ip-env-codon-op}     GTGCGCCAGG GCTACTCCCC CCTGTCCTTC CAGACCCacc tgCCCAcCCC
     dna2.msf{hiv1084ienv-codon-op}      GTGCGCCAGG GCTACTCCCC CCTGTCCTTC CAGACCCtga ccCCCAaCCC
                          Consensus      GTGCGCCAGG GCTACTCCCC CCTGTCCTTC CAGACCC--- --CCCA-CCC

                                         2151                                                2200
    dna2.msf{1157ipenvd123-codon-op}     CCGCGGCCCC GACCGCCccG aggGCATCGA GGAGGAGGGC GGCGAGCgcG
   dna2.msf{1157ipenvd1234-codon-op}     CCGCGGCCCC GACCGCCccG aggGCATCGA GGAGGAGGGC GGCGAGCgcG
  dna2.msf{shiv-1157ip-env-codon-op}     CCGCGGCCCC GACCGCCccG aggGCATCGA GGAGGAGGGC GGCGAGCgcG
     dna2.msf{hiv1084ienv-codon-op}      CCGCGGCCCC GACCGCCtgG gccGCATCGA GGAGGAGGGC GGCGAGCagG
                          Consensus      CCGCGGCCCC GACCGCC--G ---GCATCGA GGAGGAGGGC GGCGAGC--G

                                         2201                                                2250
    dna2.msf{1157ipenvd123-codon-op}     ACCGCGACCG CTCCATCCGC CTGGTGaaCG GCTcCCTGGC CCTGatCTGG
   dna2.msf{1157ipenvd1234-codon-op}     ACCGCGACCG CTCCATCCGC CTGGTGaaCG GCTcCCTGGC CCTGatCTGG
  dna2.msf{shiv-1157ip-env-codon-op}     ACCGCGACCG CTCCATCCGC CTGGTGaaCG GCTcCCTGGC CCTGatCTGG
     dna2.msf{hiv1084ienv-codon-op}      ACCGCGACCG CTCCATCCGC CTGGTGtcCG GCTtCCTGGC CCTGgcCTGG
                          Consensus      ACCGCGACCG CTCCATCCGC CTGGTG--CG GCT-CCTGGC CCTG--CTGG
```

FIGURE 2 (CONTINUED)

```
                                     2251                                                2300
 dna2.msf{1157ipenvd123-codon-op}    GACGACCTGC GCTCCCTGTG CCTGTTCTCC TACCACCGCC TGCGCGACct
dna2.msf{1157ipenvd1234-codon-op}    GACGACCTGC GCTCCCTGTG CCTGTTCTCC TACCACCGCC TGCGCGACct
dna2.msf{shiv-1157ip-env-codon-op}   GACGACCTGC GCTCCCTGTG CCTGTTCTCC TACCACCGCC TGCGCGACct
   dna2.msf{hiv1084ienv-codon-op}    GACGACCTGC GCTCCCTGTG CCTGTTCTCC TACCACCGCC TGCGCGACtg
                        Consensus    GACGACCTGC GCTCCCTGTG CCTGTTCTCC TACCACCGCC TGCGCGAC--

                                     2301                                                2350
 dna2.msf{1157ipenvd123-codon-op}    gcTgCTGATC GTGaCCCGCa tCGtgGAGCT GCTGGGCCGC cgC.......
dna2.msf{1157ipenvd1234-codon-op}    gcTgCTGATC GTGaCCCGCa tCGtgGAGCT GCTGGGCCGC cgC.......
dna2.msf{shiv-1157ip-env-codon-op}   gcTgCTGATC GTGaCCCGCa tCGtgGAGCT GCTGGGCCGC cgC.......
   dna2.msf{hiv1084ienv-codon-op}    caTcCTGATC GTGgCCCGCg cCGccGAGCT GCTGGGCCGC tcCtccctgc
                        Consensus    --T-CTGATC GTG-CCCGC- -CG--GAGCT GCTGGGCCGC --C-------

                                     2351                                                2400
 dna2.msf{1157ipenvd123-codon-op}    .......... ....GGCTGG GAGGCCCTGA AGTACtgGtG gaaCCTGcTG
dna2.msf{1157ipenvd1234-codon-op}    .......... ....GGCTGG GAGGCCCTGA AGTACtgGtG gaaCCTGcTG
dna2.msf{shiv-1157ip-env-codon-op}   .......... ....GGCTGG GAGGCCCTGA AGTACtgGtG gaaCCTGcTG
   dna2.msf{hiv1084ienv-codon-op}    gcggcctgca gaagGGCTGG GAGGCCCTGA AGTACctGgG ctcCCTGgTG
                        Consensus    ---------- ----GGCTGG GAGGCCCTGA AGTAC--G-G ---CCTG-TG

                                     2401                                                2450
 dna2.msf{1157ipenvd123-codon-op}    CAGTACTGGt cCCaGGAGCT GAAGAAcTCC GCCgTgTCCC TGCTGaACgC
dna2.msf{1157ipenvd1234-codon-op}    CAGTACTGGt cCCaGGAGCT GAAGAAcTCC GCCgTgTCCC TGCTGaACgC
dna2.msf{shiv-1157ip-env-codon-op}   CAGTACTGGt cCCaGGAGCT GAAGAAcTCC GCCgTgTCCC TGCTGaACgC
   dna2.msf{hiv1084ienv-codon-op}    CAGTACTGGg gCCtGGAGCT GAAGAAgTCC GCCaTcTCCC TGCTGgACaC
                        Consensus    CAGTACTGG- -CC-GGAGCT GAAGAA-TCC GCC-T-TCCC TGCTG-AC-C

                                     2451                                                2500
 dna2.msf{1157ipenvd123-codon-op}    CACCGCCATC GCCGTGGCCG AGGGCACCGA CCGCgTgATC GAGgTGgTgC
dna2.msf{1157ipenvd1234-codon-op}    CACCGCCATC GCCGTGGCCG AGGGCACCGA CCGCgTgATC GAGgTGgTgC
dna2.msf{shiv-1157ip-env-codon-op}   CACCGCCATC GCCGTGGCCG AGGGCACCGA CCGCgTgATC GAGgTGgTgC
   dna2.msf{hiv1084ienv-codon-op}    CACCGCCATC GCCGTGGCCG AGGGCACCGA CCGCaTcATC GAGcTGaTcC
                        Consensus    CACCGCCATC GCCGTGGCCG AGGGCACCGA CCGC-T-ATC GAG-TG-T-C
```

FIGURE 2 (CONTINUED)

```
                                  2501                                                2550
  dna2.msf{1157ipenvd123-codon-op}  AGgGCgcCTG CCGCGCCATC cGCcACATCC CCCGCCGCAT gCGCCAGGGC
 dna2.msf{1157ipenvd1234-codon-op}  AGgGCgcCTG CCGCGCCATC cGCcACATCC CCCGCCGCAT gCGCCAGGGC
dna2.msf{shiv-1157ip-env-codon-op}  AGgGCgcCTG CCGCGCCATC cGCcACATCC CCCGCCGCAT gCGCCAGGGC
   dna2.msf{hiv1084ienv-codon-op}   AGcGCatCTG CCGCGCCATC tGCaACATCC CCCGCCGCAT cCGCCAGGGC
                        Consensus   AG-GC--CTG CCGCGCCATC -GC-ACATCC CCCGCCGCAT -CGCCAGGGC

                                  2551                 2571
  dna2.msf{1157ipenvd123-codon-op}  cTgGAGcgCa tCCTGCtGTg A
 dna2.msf{1157ipenvd1234-codon-op}  cTgGAGcgCa tCCTGCtGTg A
dna2.msf{shiv-1157ip-env-codon-op}  cTgGAGcgCa tCCTGCtGTg A
   dna2.msf{hiv1084ienv-codon-op}   tTcGAGgcCg cCCTGCaGTa A
                        Consensus   -T-GAG--C- -CCTGC-GT- A
```

FIGURE 2 (CONTINUED)

ATGCGCGTGAAGGAGAAGTACCAGCACCTGTGGCGCTGGGGCTGGCG
CTGGGGCACCATGCTGCTGGGCATGCTGATGATCTGCTCCGCCACCGA
GAAGCTGTGGGTGACCGTGTACTACGGCGTGCCCGTGTGGAAGGAGGC
CAAGACCACCCTGTTCTGCGCCTCCGACGCCAAGGCCTACGAGAAGGA
GGTGCACAACATCTGGGCCACCCACGCCTGCGTGCCCACCGACCCCAA
CCCCCAGGAGATCGTGCTGGAGAACGTGACCGAGAACTTCAACATGTG
GAAGGACGACATGGTGGACCAGATGCACGAGGACATCATCTCCCTGTG
GGACCAGTCCCTGAAGCCCTGCGTGAAGCTGACCCCCCTGTGCGTGAC
CCTGAAGTGCTCCAACTTCACCCGCGAGGGCAACGTGACCTACAAGGA
GGAGATGGACAAGGTGAAGAACTGCTCCTTCAACGTGACCACCGGCAT
CCGCGACAAGAAGCAGAAGGTGAACGCCCTGTTCTACCGCCTGGACAT
CACCCCCCTGGACGAGAACAACAACAACTCCTCCGAGTACCGCTTGATC
AACTGCAAGTCCTCCACCATCACCCAGGCCTGCCCCAAGGTGAACTTCG
ACCCCATCCCCATCCACTACTGCGCCCCCGCCGGCTACGCCATCCTGAA
GTGCAACAACAAGACCTTCAACGGCACCGGCCCCTGCCACAACGTGTC
CACCGTGCAGTGCACCCACGGCATCAAGCCCGTGGTGTCCACCCAGCT
GCTGCTGAACGGCTCCCTGGCCGAGCGCGAGATCATCATCCGCTCCGA
GAACCTGACCGACAACGTGAAGACCATCATCGTGCACTTCAACGAGTCC
GTGGAGATCAACTGCACCCGCCCCAACAACAACACCCGCAAGTCCATCC
GCATCGGCCCCGGCCAGGCCTTCTACGCCACCGGCGACATCATCGGCG
ACATCCGCCAGGCCCACTGCAACATCTCCAAGGAGAACTGGAACAAGAC
CCTGCAGTGGGTGCGCGGCAAGCTGGAGGAGCACTTCCCCAACAAGAC
CATCGTGTTCAAGCCCTCCTCCGGCGGCGACCTGGAGATCACCACCCA
CTCCTTCAACTGCCGCGGCGAGTTCTTCTACTGCAACACCTCCAAGCTG
TTCAACGGCACCGACAACTCCACCCACATGGACACCGGCAACGACACC
GTGATCACCATCCCCTGCCGCATCAAGCAGATCATCAACATGTGGCAGG
AGGTGGGGCGCGCCATGTACGCCCCCCCCATCGAGGGCAACATCACCT
GCAAGTCCAACATCACCGGCCTGCTGCTGGTGCGCGACGGCGGCCAG
GACAACTCCACCAACAACACCGAGACCTTCCGCCCCGGCGGCGGCGAC
ATGCGCAACAACTGGCGCTCCGAGCTGTACAAGTACAAGGTGGTGGAG
ATCAAGCCCCTGGGCATCGCCCCCACCAAGGCCAAGCGCCGCGTGGTG
GAGCGCGAGAAGCGCGCCGTGGGCATCGGCGCCGTGTTCCTGGGCTT
CCTGGGCGCCGCCGGCTCCACCATGGGCGCCGCCTCCATCACCCTGAC
CGTGCAGGCCCGCCAGCTGCTGTCCGGCATCGTGCAGCAGCAGGACAA
CCTGCTGCGCGCCATCGAGGCCCAGCAGCACATGCTGCAGCTGACCGT
GTGGGGCATCAAACAGCTGCAGGCCCGCGTGCTGGCCATCGAGCGCTA
CCTGCAGGACCAGCAGCTGCTGGGCATCTGGGGCTGCTCCGGCAAGCT
GATCTGCACCACCGCCGTGCCCTGGAACGCCTCCTGGTCCAACAAGTC
CCAGACCGACATCTGGGAGAACATGACCTGGATGCAGTGGGACAAGGA
GATCTCCAAGCACACCGACACCATCTACCGCCTGCTGGAGGACTCCCA
GAACCAGCAGGAGAAGAACGAGAAGGACCTGCTGGCCCTGGACTCCTG
GGAGAACCTGTGGAACTGGTTCTCCATCACCAAGTGGCTGTGGTACATC
AAGATCTTCATCATGATCGTGGGCGGCCTGATCGGCCTGCGCATCATCT
TCGCCGTGCTGTCCATCGTGTCCCGCGTGCGCCAGGGCTACTCCCCCC
TGTCCTTCCAGACCCACCTGCCCACCCCCCGCGGCCCCGACCGCCCCG
AGGGCATCGAGGAGGAGGGCGGCGAGCGCGACCGCGACCGCTCCATC

FIGURE 8

CGCCTGGTGAACGGCTCCCTGGCCCTGATCTGGGACGACCTGCGCTCC
CTGTGCCTGTTCTCCTACCACCGCCTGCGCGACCTGCTGCTGATCGTGA
CCCGCATCGTGGAGCTGCTGGGCCGCCGCGGCTGGGAGGCCCTGAAG
TACTGGTGGAACCTGCTGCAGTACTGGTCCCAGGAGCTGAAGAACTCC
GCCGTGTCCCTGCTGAACGCCACCGCCATCGCCGTGGCCGAGGGCACC
GACCGCGTGATCGAGGTGGTGCAGGGCGCCTGCCGCGCCATCCGCCA
CATCCCCCGCCGCATGCGCCAGGGCCTGGAGCGCATCCTGCTGTGA
SEQ ID NO: 1

FIGURE 8 (CONTINUED)

MRVKEKYQHLWRWGWRWGTMLLGMLMICSATEKLWVTVYYGVPVWKEAKTT
LFCASDAKAYEKEVHNIWATHACVPTDPNPQEIVLENVTENFNMWKDDMVDQ
MHEDIISLWDQSLKPCVKLTPLCVTLKCSNFTREGNVTYKEEMDKVKNCSFNVT
TGIRDKKQKVNALFYRLDITPLDENNNNSSEYRLINCKSSTITQACPKVNFDPIPI
HYCAPAGYAILKCNNKTFNGTGPCHNVSTVQCTHGIKPVVSTQLLLNGSLAERE
IIIRSENLTDNVKTIIVHFNESVEINCTRPNNNTRKSIRIGPGQAFYATGDIIGDIRQ
AHCNISKENWNKTLQWVRGKLEEHFPNKTIVFKPSSGGDLEITTHSFNCRGEFF
YCNTSKLFNGTDNSTHMDTGNDTVITIPCRIKQIINMWQEVGRAMYAPPIEGNIT
CKSNITGLLLVRDGGQDNSTNNTETFRPGGGDMRNNWRSELYKYKVVEIKPLG
IAPTKAKRRVVEREKRAVGIGAVFLGFLGAAGSTMGAASITLTVQARQLLSGIVQ
QQDNLLRAIEAQQHMLQLTVWGIKQLQARVLAIERYLQDQQLLGIWGCSGKLIC
TTAVPWNASWSNKSQTDIWENMTWMQWDKEISKHTDTIYRLLEDSQNQQEKN
EKDLLALDSWENLWNWFSITKWLWYIKIFIMIVGGLIGLRIIFAVLSIVSRVRQGYS
PLSFQTHLPTPRGPDRPEGIEEEGGERDRDRSIRLVNGSLALIWDDLRSLCLFS
YHRLRDLLLIVTRIVELLGRRGWEALKYWWNLLQYWSQELKNSAVSLLNATAIA
VAEGTDRVIEVVQGACRAIRHIPRRMRQGLERILL*

SEQ ID NO: 2

FIGURE 9

ATGCGCGTGAAGGAGAAGTACCAGCACCTGTGGCGCTGGGGCTGGCGCTG
GGGCACCATGCTGCTGGGCATGCTGATGATCTGCTCCGCCACCGAGAAGCT
GTGGGTGACCGTGTACTACGGCGTGCCCGTGTGGAAGGAGGCCAAGACCA
CCCTGTTCTGCGCCTCCGACGCCAAGGCCTACGAGAAGGAGGTGCACAACA
TCTGGGCCACCCACGCCTGCGTGCCCACCGACCCCAACCCCCAGGAGATC
GTGCTGGAGAACGTGACCGAGAACTTCAACATGTGGAAGGACGACATGGTG
GACCAGATGCACGAGGACATCATCTCCCTGTGGGACCAGTCCCTGAAGCCC
TGCGTGGGCGCCGGCGCCTGCCCCAAGGTGAACTTCGACCCCATCCCCATC
CACTACTGCGCCCCCGCCGGCTACGCCATCCTGAAGTGCAACAACAAGACC
TTCAACGGCACCGGCCCCTGCCACAACGTGTCCACCGTGCAGTGCACCCAC
GGCATCAAGCCCGTGGTGTCCACCCAGCTGCTGCTGAACGGCTCCCTGGCC
GAGCGCGAGATCATCATCCGCTCCGAGAACCTGACCGACAACGTGAAGACC
ATCATCGTGCACTTCAACGAGTCCGTGGAGATCAACTGCACCCGCCCCAACA
ACAACACCCGCAAGTCCATCCGCATCGGCCCCGGCCAGGCCTTCTACGCCA
CCGGCGACATCATCGGCGACATCCGCCAGGCCCACTGCAACATCTCCAAGG
AGAACTGGAACAAGACCCTGCAGTGGGTGCGCGGCAAGCTGGAGGAGCAC
TTCCCCAACAAGACCATCGTGTTCAAGCCCTCCTCCGGCGGCGACCTGGAG
ATCACCACCCACTCCTTCAACTGCCGCGGCGAGTTCTTCTACTGCAACACCT
CCAAGCTGTTCAACGGCACCGACAACTCCACCCACATGGACACCGGCAACG
ACACCGTGATCACCATCCCCTGCCGCATCAAGCAGATCATCAACATGTGGCA
GGAGGTGGGGCGCGCCATGTACGCCCCCCCCATCGAGGGCAACATCACCT
GCAAGTCCAACATCACCGGCCTGCTGCTGGTGCGCGACGGCGGCCAGGAC
AACTCCACCAACAACACCGAGACCTTCCGCCCCGGCGGCGGCGACATGCG
CAACAACTGGCGCTCCGAGCTGTACAAGTACAAGGTGGTGGAGATCAAGCC
CCTGGGCATCGCCCCCACCAAGGCCAAGCGCCGCGTGGTGGAGCGCGAGA
AGCGCGCCGTGGGCATCGGCGCCGTGTTCCTGGGCTTCCTGGGCGCCGCC
GGCTCCACCATGGGCGCCGCCTCCATCACCCTGACCGTGCAGGCCCGCCA
GCTGCTGTCCGGCATCGTGCAGCAGCAGGACAACCTGCTGCGCGCCATCGA
GGCCCAGCAGCACATGCTGCAGCTGACCGTGTGGGGCATCAAACAGCTGCA
GGCCCGCGTGCTGGCCATCGAGCGCTACCTGCAGGACCAGCAGCTGCTGG
GCATCTGGGGCTGCTCCGGCAAGCTGATCTGCACCACCGCCGTGCCCTGGA
ACGCCTCCTGGTCCAACAAGTCCCAGACCGACATCTGGGAGAACATGACCT
GGATGCAGTGGGACAAGGAGATCTCCAAGCACACCGACACCATCTACCGCC
TGCTGGAGGACTCCCAGAACCAGCAGGAGAAGAACGAGAAGGACCTGCTG
GCCCTGGACTCCTGGGAGAACCTGTGGAACTGGTTCTCCATCACCAAGTGG
CTGTGGTACATCAAGATCTTCATCATGATCGTGGGCGGCCTGATCGGCCTGC
GCATCATCTTCGCCGTGCTGTCCATCGTGTCCCGCGTGCGCCAGGGCTACT
CCCCCCTGTCCTTCCAGACCCACCTGCCCACCCCCCGCGGCCCCGACCGC
CCCGAGGGCATCGAGGAGGAGGGCGGCGAGCGCGACCGCGACCGCTCCA
TCCGCCTGGTGAACGGCTCCCTGGCCCTGATCTGGGACGACCTGCGCTCCC
TGTGCCTGTTCTCCTACCACCGCCTGCGCGACCTGCTGCTGATCGTGACCC
GCATCGTGGAGCTGCTGGGCCGCCGCGGCTGGGAGGCCCTGAAGTACTGG
TGGAACCTGCTGCAGTACTGGTCCCAGGAGCTGAAGAACTCCGCCGTGTCC
CTGCTGAACGCCACCGCCATCGCCGTGGCCGAGGGCACCGACCGCGTGAT
CGAGGTGGTGCAGGGCGCCTGCCGCGCCATCCGCCACATCCCCCGCCGCA
TGCGCCAGGGCCTGGAGCGCATCCTGCTGTGA

SEQ ID NO: 3

FIGURE 10

MRVKEKYQHLWRWGWRWGTMLLGMLMICSATEKLWVTVYYGVPVWKEAKTT
LFCASDAKAYEKEVHNIWATHACVPTDPNPQEIVLENVTENFNMWKDDMVDQ
MHEDIISLWDQSLKPCVGAGACPKVNFDPIPIHYCAPAGYAILKCNNKTFNGTG
PCHNVSTVQCTHGIKPVVSTQLLLNGSLAEREIIIRSENLTDNVKTIIVHFNESVEI
NCTRPNNNTRKSIRIGPGQAFYATGDIIGDIRQAHCNISKENWNKTLQWVRGKL
EEHFPNKTIVFKPSSGGDLEITTHSFNCRGEFFYCNTSKLFNGTDNSTHMDTGN
DTVITIPCRIKQIINMWQEVGRAMYAPPIEGNITCKSNITGLLLVRDGGQDNSTNN
TETFRPGGGDMRNNWRSELYKYKVVEIKPLGIAPTKAKRRVVEREKRAVGIGA
VFLGFLGAAGSTMGAASITLTVQARQLLSGIVQQQDNLLRAIEAQQHMLQLTVW
GIKQLQARVLAIERYLQDQQLLGIWGCSGKLICTTAVPWNASWSNKSQTDIWEN
MTWMQWDKEISKHTDTIYRLLEDSQNQQEKNEKDLLALDSWENLWNWFSITK
WLWYIKIFIMIVGGLIGLRIIFAVLSIVSRVRQGYSPLSFQTHLPTPRGPDRPEGIE
EEGGERDRDRSIRLVNGSLALIWDDLRSLCLFSYHRLRDLLLIVTRIVELLGRRG
WEALKYWWNLLQYWSQELKNSAVSLLNATAIAVAEGTDRVIEVVQGACRAIRHI
PRRMRQGLERILL*
SEQ ID NO: 4

FIGURE 11

ATGCGCGTGAAGGAGAAGTACCAGCACCTGTGGCGCTGGGGCTGGCGCTG
GGGCACCATGCTGCTGGGCATGCTGATGATCTGCTCCGCCACCGAGAAGC
TGTGGGTGACCGTGTACTACGGCGTGCCCGTGTGGAAGGAGGCCAAGACC
ACCCTGTTCTGCGCCTCCGACGCCAAGGCCTACGAGAAGGAGGTGCACAA
CATCTGGGCCACCCACGCCTGCGTGCCCACCGACCCCAACCCCCAGGAGA
TCGTGCTGGAGAACGTGACCGAGAACTTCAACATGTGGAAGGACGACATGG
TGGACCAGATGCACGAGGACATCATCTCCCTGTGGGACCAGTCCCTGAAGC
CCTGCGTGGGCGCCGGCGCCTGCCCCAAGGTGAACTTCGACCCCATCCCC
ATCCACTACTGCGCCCCCGCCGGCTACGCCATCCTGAAGTGCAACAACAAG
ACCTTCAACGGCACCGGCCCCTGCCACAACGTGTCCACCGTGCAGTGCAC
CCACGGCATCAAGCCCGTGGTGTCCACCCAGCTGCTGCTGAACGGCTCCC
TGGCCGAGCGCGAGATCATCATCCGCTCCGAGAACCTGACCGACAACGTG
AAGACCATCATCGTGCACTTCAACGAGTCCGTGGAGATCAACTGCACCGGC
GCCGGCGCCCACTGCAACATCTCCAAGGAGAACTGGAACAAGACCCTGCA
GTGGGTGCGCGGCAAGCTGGAGGAGCACTTCCCCAACAAGACCATCGTGT
TCAAGCCCTCCTCCGGCGGCGACCTGGAGATCACCACCCACTCCTTCAACT
GCCGCGGCGAGTTCTTCTACTGCAACACCTCCAAGCTGTTCAACGGCACCG
ACAACTCCACCCACATGGACACCGGCAACGACACCGTGATCACCATCCCCT
GCCGCATCAAGCAGATCATCAACATGTGGCAGGAGGTGGGGCGCGCCATG
TACGCCCCCCCCATCGAGGGCAACATCACCTGCAAGTCCAACATCACCGGC
CTGCTGCTGGTGCGCGACGGCGGCCAGGACAACTCCACCAACAACACCGA
GACCTTCCGCCCCGGCGGCGGCGACATGCGCAACAACTGGCGCTCCGAG
CTGTACAAGTACAAGGTGGTGGAGATCAAGCCCCTGGGCATCGCCCCCAC
CAAGGCCAAGCGCCGCGTGGTGGAGCGCGAGAAGCGCGCCGTGGGCATC
GGCGCCGTGTTCCTGGGCTTCCTGGGCGCCGCCGGCTCCACCATGGGCG
CCGCCTCCATCACCCTGACCGTGCAGGCCCGCCAGCTGCTGTCCGGCATC
GTGCAGCAGCAGGACAACCTGCTGCGCGCCATCGAGGCCCAGCAGCACAT
GCTGCAGCTGACCGTGTGGGGCATCAAACAGCTGCAGGCCCGCGTGCTGG
CCATCGAGCGCTACCTGCAGGACCAGCAGCTGCTGGGCATCTGGGGCTGC
TCCGGCAAGCTGATCTGCACCACCGCCGTGCCCTGGAACGCCTCCTGGTC
CAACAAGTCCCAGACCGACATCTGGGAGAACATGACCTGGATGCAGTGGG
ACAAGGAGATCTCCAAGCACACCGACACCATCTACCGCCTGCTGGAGGACT
CCCAGAACCAGCAGGAGAAGAACGAGAAGGACCTGCTGGCCCTGGACTCC
TGGGAGAACCTGTGGAACTGGTTCTCCATCACCAAGTGGCTGTGGTACATC
AAGATCTTCATCATGATCGTGGGCGGCCTGATCGGCCTGCGCATCATCTTC
GCCGTGCTGTCCATCGTGTCCCGCGTGCGCCAGGGCTACTCCCCCCTGTC
CTTCCAGACCCACCTGCCCACCCCCCGCGGCCCCGACCGCCCCGAGGGC
ATCGAGGAGGAGGGCGGCGAGCGCGACCGCGACCGCTCCATCCGCCTGG
TGAACGGCTCCCTGGCCCTGATCTGGGACGACCTGCGCTCCCTGTGCCTG
TTCTCCTACCACCGCCTGCGCGACCTGCTGCTGATCGTGACCCGCATCGTG
GAGCTGCTGGGCCGCCGCGGCTGGGAGGCCCTGAAGTACTGGTGGAACC
TGCTGCAGTACTGGTCCCAGGAGCTGAAGAACTCCGCCGTGTCCCTGCTGA
ACGCCACCGCCATCGCCGTGGCCGAGGGCACCGACCGCGTGATCGAGGT
GGTGCAGGGCGCCTGCCGCGCCATCCGCCACATCCCCCGCCGCATGCGC
CAGGGCCTGGAGCGCATCCTGCTGTGA
SEQ ID NO: 5

FIGURE 12

MRVKEKYQHLWRWGWRWGTMLLGMLMICSATEKLWVTVYYGVPVWKEAKTT
LFCASDAKAYEKEVHNIWATHACVPTDPNPQEIVLENVTENFNMWKDDMVDQ
MHEDIISLWDQSLKPCVGAGACPKVNFDPIPIHYCAPAGYAILKCNNKTFNGTG
PCHNVSTVQCTHGIKPVVSTQLLLNGSLAEREIIIRSENLTDNVKTIIVHFNESVEI
NCTGAGAHCNISKENWNKTLQWVRGKLEEHFPNKTIVFKPSSGGDLEITTHSF
NCRGEFFYCNTSKLFNGTDNSTHMDTGNDTVITIPCRIKQIINMWQEVGRAMYA
PPIEGNITCKSNITGLLLVRDGGQDNSTNNTETFRPGGGDMRNNWRSELYKYK
VVEIKPLGIAPTKAKRRVVEREKRAVGIGAVFLGFLGAAGSTMGAASITLTVQAR
QLLSGIVQQQDNLLRAIEAQQHMLQLTVWGIKQLQARVLAIERYLQDQQLLGIW
GCSGKLICTTAVPWNASWSNKSQTDIWENMTWMQWDKEISKHTDTIYRLLEDS
QNQQEKNEKDLLALDSWENLWNWFSITKWLWYIKIFIMIVGGLIGLRIIFAVLSIV
SRVRQGYSPLSFQTHLPTPRGPDRPEGIEEEGGERDRDRSIRLVNGSLALIWD
DLRSLCLFSYHRLRDLLLIVTRIVELLGRRGWEALKYWWNLLQYWSQELKNSAV
SLLNATAIAVAEGTDRVIEVVQGACRAIRHIPRRMRQGLERILL*
SEQ ID NO: 6

FIGURE 13

ATGCGCGTGAAGGAGAAGTACCAGCACCTGTGGCGCTGGGGCTGGCGCT
GGGGCACCATGCTGCTGGGCATGCTGATGATCTGCTCCGCCACCGAGAAG
CTGTGGGTGACCGTGTACTACGGCGTGCCCGTGTGGAAGGAGGCCAAGA
CCACCCTGTTCTGCGCCTCCGACGCCAAGGCCTACGAGAAGGAGGTGCAC
AACATCTGGGCCACCCACGCCTGCGTGCCCACCGACCCCAACCCCCAGGA
GATCGTGCTGGAGAACGTGACCGAGAACTTCAACATGTGGAAGGACGACA
TGGTGGACCAGATGCACGAGGACATCATCTCCCTGTGGGACCAGTCCCTG
AAGCCCTGCGTGGGCGCCGGCGCCTGCCCCAAGGTGAACTTCGACCCCA
TCCCCATCCACTACTGCGCCCCCGCCGGCTACGCCATCCTGAAGTGCAAC
AACAAGACCTTCAACGGCACCGGCCCCTGCCACAACGTGTCCACCGTGCA
GTGCACCCACGGCATCAAGCCCGTGGTGTCCACCCAGCTGCTGCTGAACG
GCTCCCTGGCCGAGCGCGAGATCATCATCCGCTCCGAGAACCTGACCGAC
AACGTGAAGACCATCATCGTGCACTTCAACGAGTCCGTGGAGATCAACTGC
ACCGGCGCCGGCGCCCACTGCAACATCTCCAAGGAGAACTGGAACAAGAC
CCTGCAGTGGGTGCGCGGCAAGCTGGAGGAGCACTTCCCCAACAAGACC
ATCGTGTTCAAGCCCTCCTCCGGCGGCGACCTGGAGATCACCACCCACTC
CTTCAACTGCCGCGGCGAGTTCTTCTACTGCAACGGCGCCGGCCCCTGCC
GCATCAAGCAGATCATCAACATGTGGCAGGAGGTGGGGCGCGCCATGTAC
GCCCCCCCCATCGAGGGCAACATCACCTGCAAGTCCAACATCACCGGCCT
GCTGCTGGTGCGCGACGGCGGCCAGGACAACTCCACCAACAACACCGAG
ACCTTCCGCCCCGGCGGCGGCGACATGCGCAACAACTGGCGCTCCGAGC
TGTACAAGTACAAGGTGGTGGAGATCAAGCCCCTGGGCATCGCCCCCACC
AAGGCCAAGCGCCGCGTGGTGGAGCGCGAGAAGCGCGCCGTGGGCATC
GGCGCCGTGTTCCTGGGCTTCCTGGGCGCCGCCGGCTCCACCATGGGCG
CCGCCTCCATCACCCTGACCGTGCAGGCCCGCCAGCTGCTGTCCGGCATC
GTGCAGCAGCAGGACAACCTGCTGCGCGCCATCGAGGCCCAGCAGCACA
TGCTGCAGCTGACCGTGTGGGGCATCAAACAGCTGCAGGCCCGCGTGCT
GGCCATCGAGCGCTACCTGCAGGACCAGCAGCTGCTGGGCATCTGGGGC
TGCTCCGGCAAGCTGATCTGCACCACCGCCGTGCCCTGGAACGCCTCCTG
GTCCAACAAGTCCCAGACCGACATCTGGGAGAACATGACCTGGATGCAGT
GGGACAAGGAGATCTCCAAGCACACCGACACCATCTACCGCCTGCTGGAG
GACTCCCAGAACCAGCAGGAGAAGAACGAGAAGGACCTGCTGGCCCTGG
ACTCCTGGGAGAACCTGTGGAACTGGTTCTCCATCACCAAGTGGCTGTGG
TACATCAAGATCTTCATCATGATCGTGGGCGGCCTGATCGGCCTGCGCATC
ATCTTCGCCGTGCTGTCCATCGTGTCCCGCGTGCGCCAGGGCTACTCCCC
CCTGTCCTTCCAGACCCACCTGCCCACCCCCCGCGGCCCCGACCGCCCC
GAGGGCATCGAGGAGGAGGGCGGCGAGCGCGACCGCGACCGCTCCATC
CGCCTGGTGAACGGCTCCCTGGCCCTGATCTGGGACGACCTGCGCTCCCT
GTGCCTGTTCTCCTACCACCGCCTGCGCGACCTGCTGCTGATCGTGACCC
GCATCGTGGAGCTGCTGGGCCGCCGCGGCTGGGAGGCCCTGAAGTACTG
GTGGAACCTGCTGCAGTACTGGTCCCAGGAGCTGAAGAACTCCGCCGTGT
CCCTGCTGAACGCCACCGCCATCGCCGTGGCCGAGGGCACCGACCGCGT
GATCGAGGTGGTGCAGGGCGCCTGCCGCGCCATCCGCCACATCCCCCGC
CGCATGCGCCAGGGCCTGGAGCGCATCCTGCTGTGA

SEQ ID NO: 7

FIGURE 14

MRVKEKYQHLWRWGWRWGTMLLGMLMICSATEKLWVTVYYGVPVWKEAKTT
LFCASDAKAYEKEVHNIWATHACVPTDPNPQEIVLENVTENFNMWKDDMVDQ
MHEDIISLWDQSLKPCVGAGACPKVNFDPIPIHYCAPAGYAILKCNNKTFNGTG
PCHNVSTVQCTHGIKPVVSTQLLLNGSLAEREIIIRSENLTDNVKTIIVHFNESVEI
NCTGAGAHCNISKENWNKTLQWVRGKLEEHFPNKTIVFKPSSGGDLEITTHSF
NCRGEFFYCNGAGPCRIKQIINMWQEVGRAMYAPPIEGNITCKSNITGLLLVRD
GGQDNSTNNTETFRPGGGDMRNNWRSELYKYKVVEIKPLGIAPTKAKRRVVE
REKRAVGIGAVFLGFLGAAGSTMGAASITLTVQARQLLSGIVQQQDNLLRAIEA
QQHMLQLTVWGIKQLQARVLAIERYLQDQQLLGIWGCSGKLICTTAVPWNASW
SNKSQTDIWENMTWMQWDKEISKHTDTIYRLLEDSQNQQEKNEKDLLALDSW
ENLWNWFSITKWLWYIKIFIMIVGGLIGLRIIFAVLSIVSRVRQGYSPLSFQTHLPT
PRGPDRPEGIEEEGGERDRDRSIRLVNGSLALIWDDLRSLCLFSYHRLRDLLLIV
TRIVELLGRRGWEALKYWWNLLQYWSQELKNSAVSLLNATAIAVAEGTDRVIEV
VQGACRAIRHIPRRMRQGLERILL*

SEQ ID NO: 8

FIGURE 15

GCATGCTGTAGAGCAAGAAATGGAGCCAGTAGATCCTAGACTAGAGCCCTG
GAAGCATCCAGGAAGCAGGCCTAAAACTGCTTGTACCAATTGCTATTGTAAA
AAGTGTTGCTTTCATTGCCAAGTTTGTTTCATAACAAAAGCCCTAGGCATCTC
CTATGGCAGGAAGAAGCGGAGACAGCGACGAAGAGCTCATCAGAACAGTC
AGACTCATCAAGCTTCTCTATCAAAGCAGTAAGTAGTACATGTAATGCAATC
TATACAAATAGAAATAGTAGCATTAGTAGTAGCAATAATAATAGCAATAGTTG
TGTGGTCCATAGTAATCATAGAATATAGGAAAATATTAAGACAAAGAAAAATA
GACAGGTTAATTAATAGACTAATAGAAAGAGCAGAAGACAGTGGCAATGAG
AGTGAAGGAGAAATATCAGCACTTGTGGAGATGGGGGTGGAGATGGGGCA
TCATGCTCCTTGGGATGTTGATGATCTGTAGTGCTACAGAAAAATTGTGGGT
CACAGTCTATTATGGGGTACCTGTATGGAAAGAAGCAAAAACTACTTTATTC
TGTGCATCAAATGCTAAAGCATATGAGAAAGAAGTACATAACATCTGGGCTA
CACATGCCTGTGTACCCACAGACCCCAACCCACAAGAAATAGTTTTGGGAA
ATGTAACAGAAAATTTTAACATGTGGAAAAATGACATGGTGGATCAGATGCA
TGAGGATATAATCAGTTTATGGGATCAAAGCCTAAAGCCATGTGTAAAGTTG
ACTTCACTCTGTGTCACTTTAAAGTGTAGTAATTTTACCGGGAAGAGTAATGT
TACCTACAAAGGGGATATGGAAGTAAAAAATTGCTCTTTCAATGTAACCACA
GAAATAAGAGATAAGAAGCAGAAAGTGTATGCTCTTTTTTATAGACTTGATAT
AACACCACTTGATGACAACTCTAGTGAGTATATATTAATAAATTGCAATTCCT
CAACCATAACACAAGCCTGTCCAAAGGTCAATTTTGACCCAATTCCTATACA
TTATTGTGCTCCAGCTGGTTATGCGATTCTAAAGTGTAATAATAAGACATTTA
ATGGGACAGGACCATGCCATAATGTCAGTACAGTACAATGTACACATGGAAT
TAAGCCAGTGGTATCAACTCAACTACTGTTAAACGGTAGCCTAGCAGAAGG
GGAGATAATAATTAGATCTGAAAATCTGACAGACAATGTCAAAACAATAATA
GTACACTTTAATGAATCTGTAGAAATTACTTGTACAAGACCCAACAATAATAC
AAGAAAAAGTATAAGCATAGGACCAGGACAAGCAATCTATGCCACAGGTGA
TATAATAGGAGACATAAGACAAGCACACTGTAACATTAGTAAAGAAAATTGG
AACAAAACTTTACAATGGGTAAGGGGAAAATTAAAAGAACACTTCCCTAATA
AAACAATAGTATTTAAACCATCCTCAGGAGGGGATCTAGAAATTACAACACA
TAGCTTTAATTGTAGAGGAGAATTTTTCTATTGCAACACATCAAAACTGTTTA
ATAGTACAGACAATAGTACACACATGGGTACAGAAAATAATACAATCATCAC
AATCCCATGTAGAATAAAACAAATTATAAACATGTGGCAGGAGGTAGGACGA
GCAATGTATGCCCCCCCCATAGAAGGAAACATAACATGTAAATCAAATATCA
CAGGACTACTACTGGTACGTGATGGAGGATGGGACAACAGTACAAATGACA
CAGAAACATTCAGGCCTGGAGGAGGAGATATGAGGGACAATTGGAGAAGT
GAATTATATAAATATAAGGTGGTAGAAGTCAAGCCATTGGGAATAGCACCCA
CTAAGGCAAAAAGGAGAGTGGTGGAGAGAGAAAAAAGAGCAGTGGGAATA
GGAGCTGTGTTCCTTGGGTTCTTGGGAGCAGCAGGAAGCACTATGGGCGC
GGCGTCAATAACGCTGACGGTACAGGCCAGACAACTGTTGTCTGGTATAGT
GCAGCAGCAAGACAATTTGCTGAGAGCTATAGAGGCGCAACAACATATGTT
GCAACTCACAGTCTGGGGCATTAAGCAGCTCCAGGCGAGAGTCCTGGCTAT
AGAAAGATACCTACAGGATCAACAGCTCCTAGGGATTTGGGGCTGCTCTGG
AAAACTCATCTGCACCACTGCTGTGCCTTGGAACGACAGTTGGAGTAATAAA
TCTCAAACAGATATTTGGGAGAACATGACCTGGATGCAGTGGGATAGAGAA
ATTAGTAGACACACAGACACAATATACAGGTTGCTTGAAGACTCACAAAACC
AGCAGGAGAAAAATGAAAAAGATTTATTAGCATTGGACAGTTGGAAAAATTT
GTGGAATTGGTTTAGCATAACAAGGTGGCTGTGGTATATAAAAATATTCATA

FIGURE 16

ATGATAGTAGGAGGCCTGATAGGTTTGAGAATAATTTTTGCTGTGCTCTCGA
TAGTGAATAGAGTTAGGCAGGGATACTCACCATTATCGTTTCAGACCCACCT
CCCACTTCCGAGGGGAGCCGACAGGCCCGAAGGAATAGAAGAAGAAGGTG
GAGAGAGAGACAGAGACAGATCCATTCGATTAGTGACCGGATCCTTAGCAC
TTATCTGGGACGATCTGCGGAGCCTGTGCCTCTTCAGCTACCACCGCTTGA
GAGACTTACTCTTGATTGTAACGAGGACTGTGGAACTCCTGGGACGCAGAG
GGTGGGAAGCCCTCAAATATTGGTGGAATCTCCTACTGTATTGGAGTCAGG
AACTAAAGAATAGTGCTGTTAGCTTGCTCAACGCCACAGCCATAGCAGTAAG
ACAATATGGGTGGAGCTATTTCCATGAGGCGGTCCAGGCCGTCTGGAGATC
TGCGACAGAGACTCTTGCGGGCGCGTGGGGAGACTTATGGGAGATTCTTA
GGAGAGGTGGAAGATGGATACTCGCAATCCCCAGGAGGATTAGACAAGGG
CTCGAGCTCACTCTCTTGTGAGGGACAGAAATACAATCAGGGACAGCATAT
GAATACTCCATGGAGAAACCCAGCTGAAGAGGGAGAAAAATTAGCATACAG
AAAACAAAATATGGATGATATAGATGAGGAAGATGATGACTTGGTAGGGGTA
TCAGTGAGGCCAAAAGTTCTCCTAAGAACAATGAGTTACAAATTGGCAATAG
ACATGTCTCATTTTATAAAAGAAAAGGGGGGACTGGAAGGGATTTATTACAG
TGCAAGAAGACATAGAATCTTAGACATATACTTAGAAAAGGAAGAAGGCATC
ATACCAGATTGGCAGGATTACACCTCAGGACCAGGAATTAGATACCCAAAG
ACATTTGGCTGGCTATGGAAATTAGTCCCTGTAGATGTATCAGATGAGGCAC
AGGAGGATGAGGAGCATTACTTAATGCATCCAGCTCAAACTTCCCAGTGGG
ATGACCCTTGGGGAGAGGTTCTAGCATGGAAGTTTGATCCAACTCTGGCCT
ACACTTATGAGGCATATGTTAGATACCCAGAAGAGTTTGGAAGCAAGTCAG
GCCTGTCAGAGGAAGAGGTTAGAAGAAGGCTAACCGCAAGAGGCCTTCTTA
ACATGGCTGACAAGAAGGAAACTCGCTGAAACAGCAGGGACTTTCCACAAG
GGGATGTTACGGGGAGGTACTGGGGAGGAGCCGGTCGGGAACGCCCACT
TTCTTGATGTATAAATATCACTGCATTTCGCTCTGTATTCAGTCGCTCTGCGG
AGAGGCTGGCAGATTGAGCCCTGGGAGGTTCTCTCCAGCACTAGCAGGTA
GAGCCTGGGTGTTCCCTGCTAGACTCTCACCAGCACTTGGCCGGTGCTGG
GCAGAGTGACTCCACGCTTGCTTACTTAAAGCCCTCTTCAATAAAGCTGCCA
TTTAGAAGTA

SEQ ID NO:9

FIGURE 16 (CONTINUED)

MRVKEKYQHLWRWGWRWGIMLLGMLMICSATEKLWVTVYYGVPVWKEAKT
TLFCASNAKAYEKEVHNIWATHACVPTDPNPQEIVLGNVTENFNMWKNDMVD
QMHEDIISLWDQSLKPCVKLTSLCVTLKCSNFTGKSNVTYKGDMEVKNCSFN
VTTEIRDKKQKVYALFYRLDITPLDDNSSEYILINCNSSTITQACPKVNFDPIPIH
YCAPAGYAILKCNNKTFNGTGPCHNVSTVQCTHGIKPVVSTQLLLNGSLAEGE
IIIRSENLTDNVKTIIVHFNESVEITCTRPNNNTRKSISIGPGQAIYATGDIIGDIRQ
AHCNISKENWNKTLQWVRGKLKEHFPNKTIVFKPSSGGDLEITTHSFNCRGEF
FYCNTSKLFNSTDNSTHMGTENNTIITIPCRIKQIINMWQEVGRAMYAPPIEGNI
TCKSNITGLLLVRDGGWDNSTNDTETFRPGGGDMRDNWRSELYKYKVVEVK
PLGIAPTKAKRRVVEREKRAVGIGAVFLGFLGAAGSTMGAASITLTVQARQLL
SGIVQQQDNLLRAIEAQQHMLQLTVWGIKQLQARVLAIERYLQDQQLLGIWGC
SGKLICTTAVPWNDSWSNKSQTDIWENMTWMQWDREISRHTDTIYRLLEDS
QNQQEKNEKDLLALDSWKNLWNWFSITRWLWYIKIFIMIVGGLIGLRIIFAVLSI
VNRVRQGYSPLSFQTHLPLPRGADRPEGIEEEGGERDRDRSIRLVTGSLALIW
DDLRSLCLFSYHRLRDLLLIVTRTVELLGRRGWEALKYWWNLLLYWSQELKN
SAVSLLNATAIAVRQYGWSYFHEAVQAVWRSATETLAGAWGDLWEILRRGG
RWILAIPRRIRQGLELTLL*

SEQ ID NO: 10

FIGURE 17

```
SHIV-1157i    Nef   MGGAISMRRSRPSGDLRQRLLRARGETYGRLLGEVEDG
SHIV-1157ipd  Nef   ------------------------------F-------

YSQSPGGLDKGLSSLSCEGQKYNQGQYMNTPWRNPAEEREKLAYRKQNMDDIDEEDDDL
-----------S--------------H-----------G---------- ---------

VGVSVRPKVPLRTMSYKLAIDMSHFIKEKGGLEGIYYSARRHRILDIYLEKEEGIIPDW
---------L-------------------------------------------------

QDYTSGPGIRYPKTFGWLWKLVPVNVSDEAQEDEEHYLMHPAQTSQWDDPWGEVLAWKF
------------------------D----------------------------------

DPTLAYTYEAYVRYPEEFGSKSGLSEEEVRRRLTARGLLNMADKKETR
------------------------------------------------
```

SEQ ID NO: 11

FIGURE 18

MODIFIED HUMAN IMMUNODEFICIENCY VIRUS CLADE C ENVELOPE POLYPEPTIDES OBTAINED FROM A ZAMBIAN ISOLATE

RELATED APPLICATION

This application is a continuation application of International Application No. PCT/US2007/ 007774, which designated the United States and was filed on Mar. 28, 2007, and which claims the benefit of U.S. Provisional Application No. 60/787,270, filed on Mar. 29, 2006. The entire teachings of the above applications are incorporated herein by reference.

GOVERNMENT SUPPORT

The invention was supported, in whole or in part, by a grant P01 AI48240 from the National Institutes of Health-NIAID. The Government has certain rights in the invention.

SEQUENCE LISTING

The instant application contains a Sequence Listing which has been submitted via EFS-Web and is hereby incorporated by reference in its entirety. Said ASCII COPY, created on Dec. 7, 2009, is named 67925CON.txt, and is 76,062 bytes in size.

BACKGROUND

Acquired immune deficiency syndrome (AIDS) is a major health threat throughout the world. HIV is the leading cause of AIDS. To date there are no effective vaccines for AIDS. For these reasons there are great efforts to create vaccines and suitable models for testing the vaccines. One target of therapeutic vaccines in the envelope protein of HIV (gp160). During infection, gp160 is cleaved by host cell proteases to from the gp120 and gp41. Barnett et al. (US2002/0146683) describes numerous HIV Env polypeptides in which at least one of the native B-sheet configurations has been modified. The constructs are taught to be used in vaccine compositions. Vajdy et al. (US2005/0175631) teaches pharmaceutical compositions for the treatment of AIDS in which the compositions have an HIV antigen and a mucosal adjuvant.

SUMMARY OF THE INVENTION

The invention provides methods and compositions for raising an immune response in a subject by administering an HIV antigen. The HIV antigens include HIV clade C polynucleotides and polypeptides. The invention also provides for recombinant HIV viral particles and compositions. The recombinant HIV viral particles are particularly useful in animal models for studying HIV.

In one aspect, the invention provides for a method of inducing an immune response in a subject comprising administering the polypeptides or polynucleotides encoding an HIV clade C envelope in an amount sufficient to induce an immune response in the subject.

In another aspect, the invention provides an isolated HIV envelope polypeptide. The polypeptide comprises the amino acid sequence of SEQ ID NO:2.

In another aspect, the invention provides a modified HIV clade C envelope polypeptide in which the V1 region is deleted. In yet another aspect, the V1/V2 (SEQ ID NO:4), V1, V2, V3 (SEQ ID NO:6) or V1, V2, V3, V4 (SEQ ID NO:8) regions of the modified HIV clade C envelope polypeptide are deleted.

In another aspect, the present invention provides an isolated polynucleotide encoding an HIV envelope polypeptide. The polynucleotide comprises the nucleotide sequence of SEQ ID NO:1. In another aspect, the invention provides a modified HIV clade C envelope polynucleotide in which the V1 region is deleted. In yet another aspect, the V1/V2 (SEQ ID NO:3), V1, V2, V3 (SEQ ID NO:5) or V1, V2, V3, V4 (SEQ ID NO:7) regions of the modified HIV clade C envelope polynucleotide are deleted.

The invention also provides for vectors and compositions which include the HIV clade C envelope polynucleotides and polypeptides of the invention.

In yet another aspect, the present invention provides an HIV recombinant viral particle having an envelope region with the nucleotide sequence of SEQ ID NO: 9 or SEQ ID NO:10. In another aspect the HIV recombinant viral particle comprising the nucleotide sequence of ATCC accession No.

In still another aspect, the invention provides a method for assessing the efficacy of a candidate AIDS vaccine in a non-human primate. The method includes the steps of administering a candidate AIDS vaccine to a subject, infecting the non-human primate with the viral particle of the invention, and detecting disease progression.

BRIEF DESCRIPTION OF THE DRAWINGS

FIG. 2 depicts an alignment of the nucleic acid sequence of the HIV envelope consensus region (SEQ ID NO: 14) with the envelope regions of strains 1084i (SEQ ID NO: 15), full-length 1157ip (SEQ ID NO:1), 1157ip with deletions in envelope variable regions 1, 2 and 3 (SEQ ID NO: 5), and 1157ip with deletions in envelope variable regions 1, 2, 3 and 4 (SEQ ID NO: 7).

FIG. 8 depicts the nucleotide sequence of the envelope region of the construct designated 1157ip env (SEQ ID NO: 1).

FIG. 9 depicts the amino acid sequence of the envelope region of the construct designated 1157ip env. (SEQ ID NO: 2).

FIG. 10 depicts the nucleotide sequence of the envelope region of the construct designated 1157ipdv12 (SEQ ID NO: 3).

FIG. 11 depicts the amino acid sequence of the envelope region of the construct designated 1157ipdv12 (SEQ ID NO: 4).

FIG. 12 depicts the nucleotide sequence of the envelope region of the construct designated 1157ipdv123 (SEQ ID NO: 5).

FIG. 13 depicts the amino acid sequence of the envelope region of the construct designated 1157ipdv123 (SEQ ID NO: 6).

FIG. 14 depicts the nucleotide sequence of the envelope region of the construct designated 1157ipdv1234 (SEQ ID NO: 7).

FIG. 15 depicts the amino acid sequence of the envelope region of the construct designated 1157ipdv1234 (SEQ ID NO: 8).

FIG. 16 depicts the nucleotide sequence of the envelope region of the construct designated 1157ipd3 (SEQ ID NO: 9).

FIG. 17 depicts the amino acid sequence of the envelope region of the construct designated 1157ipd3 (SEQ ID NO: 10).

FIG. 18 depicts the amino acid sequences of the Nef region of the constructs designated 1157ipd (SEQ ID NO: 11) and 1157i (SEQ ID NO: 16).

DETAILED DESCRIPTION

Definitions

Figure 1:
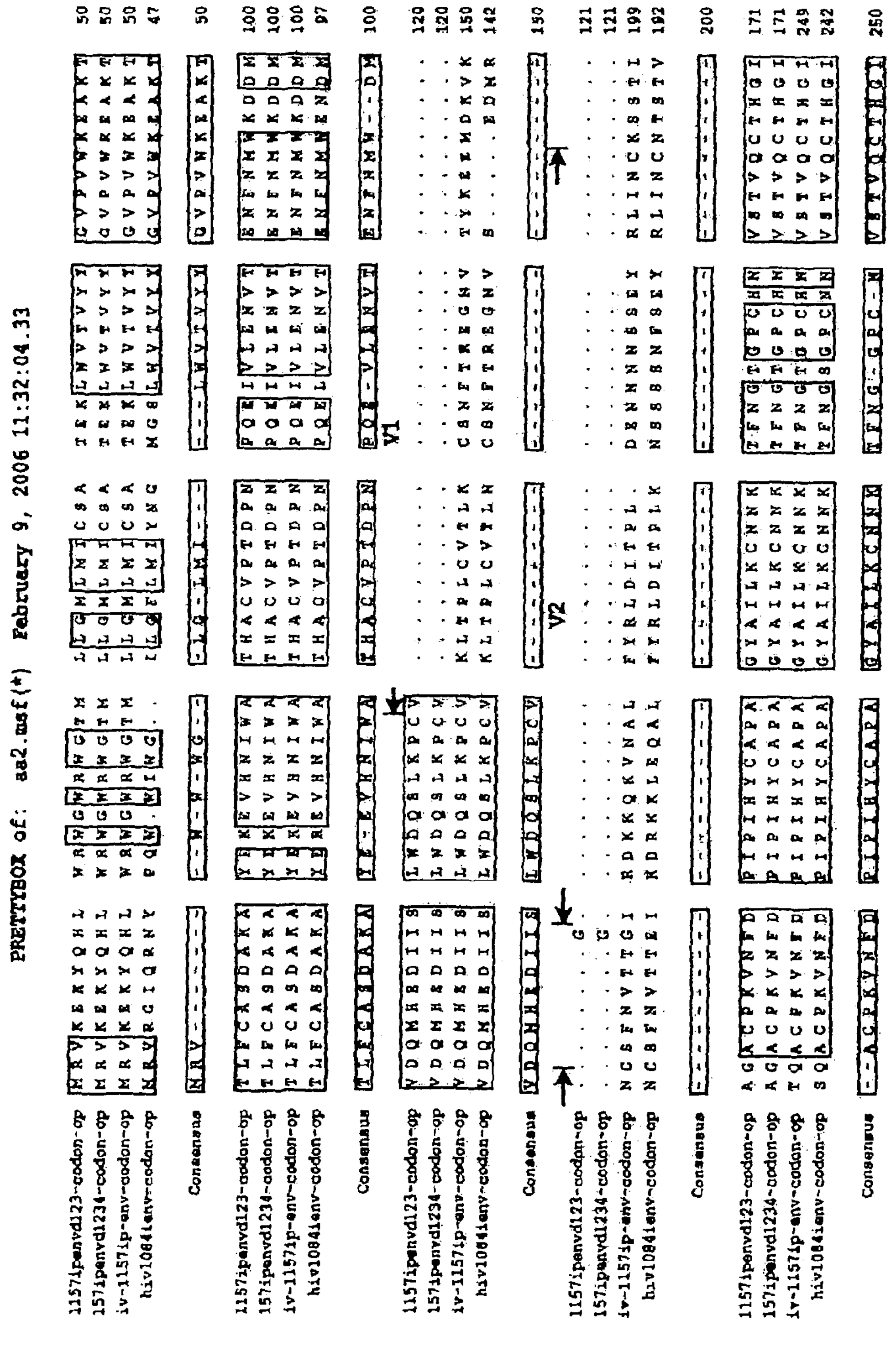
FIG. 1 depicts an alignment of the amino acid sequence of the HIV envelope consensus region (SEQ ID NO:12) with the envelope regions of strains 1084i (SEQ ID NO:13), full-length 1157ip (SEQ ID NO:2), 1157ip with deletions in envelope variable regions 1, 2 and 3 (SEQ ID NO: 6), and 1157ip with deletions in envelope variable regions 1, 2, 3 and 4 (SEQ ID NO: 8).
Figure 1:
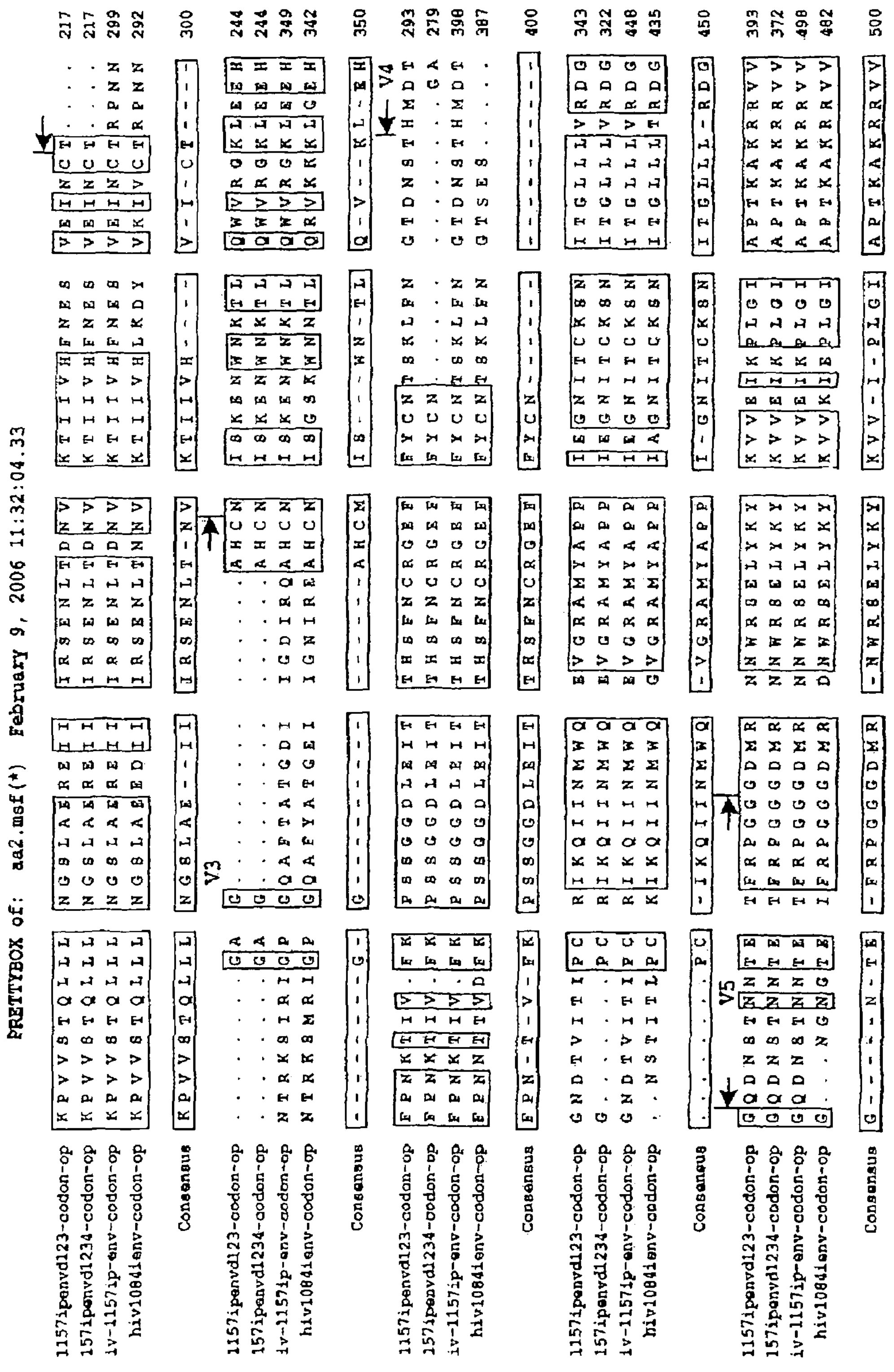

As used herein, a "polynucleotide" refers to a covalently linked sequence of nucleotides (i.e., ribonucleotides for RNA and deoxyribonucleotides for DNA) in which the 3' position of the pentose of one nucleotide is joined by a phosphodiester linkage to the 5' position of the pentose of the next nucleotide. The term "polynucleotide" includes single- and double-stranded polynucleotides. "Polynucleotide" also embraces a short polynucleotide, often referred to as an oligonucleotide (e.g., a primer or a probe). A polynucleotide has a "5'-terminus" and a "3'-terminus" because polynucleotide phosphodiester linkages occur between the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. As used herein, a polynucleotide sequence, even if internal to a larger polynucleotide (e.g., a sequence region within a polynucleotide), also can be said to have 5'- and 3'-ends.

The term "polynucleotide" as it is employed herein embraces chemically, enzymatically, or metabolically modified forms of a polynucleotide. The term also captures sequences that include any of the known base analogs of DNA and RNA, and includes modifications such as deletions, additions and substitutions (generally conservative in nature), to the native sequence, so long as the nucleic acid molecule encodes a therapeutic or antigenic protein. Modifications of polynucleotides may have any number of effects including, for example, facilitating expression of the polypeptide product in a host cell.

The polynucleotides used in the present invention include polynucleotides encoding for an immunogenic fragment or derivative thereof. Such immunogenic fragments or derivatives thereof include fragments encoding for a B-cell epitope or a T-cell epitope. The polynucleotides used in the present invention also include polynucleotides encoding for an env gene or recombinant HIV viral particle.

As used herein a "polypeptide" is a molecular chain of amino acids and does not refer to a specific length of the product. Thus, peptides, oligopeptides dimers, multimers, and the like are included within the definition of polypeptide. This term is also intended to include polypeptide that have been subjected to post-expression modifications such as, for example, glycosylations, acetylations, phosphorylations and the like. Furthermore, for purposes of the present invention, a "polypeptide" refers to a protein that includes modifications, such as deletions, additions and substitutions (generally conservative in nature), to the native sequence, as long as the protein maintains the desired activity.

As used herein, "isolated" is meant, when referring to a polynucleotide or a polypeptide, that the indicated molecule is separate and discrete from the whole organism with which the molecule is found in nature or, when the polynucleotide or polypeptide is not found in nature, is sufficiently free of other biological macromolecules so that the polynucleotide or polypeptide can be used for its intended purpose.

As used herein, "antigen" refers to a molecule containing one or more epitopes (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes.

Also for purposes of the present invention, an "antigen" refers to a protein that includes modifications, such as deletions, additions and substitutions (generally conservative in nature), to the native sequence, so long as the protein maintains the ability to elicit an immunological response, as defined herein. Antigens of the present invention include the polypeptides of SEQ ID NOs: 2, 4, 6, 8, 10 and 11 and variants thereof.

As used herein, the term "inducing an immune response" to an antigen or composition is the development in a subject of a humoral and/or a cellular immune response to an antigen present in the composition of interest. A "humoral immune response" refers to an immune response mediated by antibody molecules, while a "cellular immune response" is one mediated by T-lymphocytes and/or other white blood cells. The antigen of interest may also elicit an antibody-mediated immune response. Hence, an immunological response may include one or more of the following effects: the production of antibodies by B-cells; and/or the activation of suppressor, cytotoxic, or helper T-cells and/or T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

A cellular immune response involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, specific effector cells, such as B and plasma cells as well as cytotoxic T cells, against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. In addition, a chemokine response may be induced by various white blood or endothelial cells in response to an administered antigen.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

A cell-mediated immunological response maybe determined by a number of assays known in the art including, lymphoproliferation (lymphocyte activation) assays, CTL cytotoxic cell assays, or by assaying for T-lymphocytes specific for the antigen in a sensitized subject. Such assays are well known in the art. See, e.g., Erickson et al., J. Immunol. (1993) 151:4189-4199; Doe et al., Eur. J. Immunol. (1994) 24:2369-2376. Cell-mediated immune response may also be determined by the measurement of intracellular cytokines or cytokine secretion by T-cell populations (e.g., by ELISPOT technique), or by measurement of epitope specific T-cells (e.g., by the tetramer technique) (reviewed by McMichael, A. J., and O'Callaghan, C. A., J. Exp. Med. 187(9):1367-1371, 1998; Mcheyzer-Williams, M. G., et al, Immunol. Rev. 150: 5-21, 1996; Lalvani, A., et al, J. Exp. Med. 186:859-865, 1997).

As used herein, the terms "Env polypeptide" or "envelope polypeptide" refer to a molecule derived from an envelope protein, e.g. from HIV Env (SEQ ID NO:2 or variants thereof). The envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp120 is released from the surface of virions and infected cells. Env polypeptides may also include gp140 polypeptides. Env polypeptides can exist as monomers, dimers or multimers.

As used herein, a "gp120 polypeptide" is meant a molecule derived from a gp120 region of the Env polypeptide. The primary amino acid sequence of gp120 is approximately 511 amino acids. The amino acid sequence of gp120 contains five relatively conserved domains interspersed with five variable domains. The variable domains contain extensive amino acid substitutions, insertions and deletions. A "gp120 polypeptide" includes both single subunits or multimers.

An "Env polypeptide" or "gp120 polypeptide" as defined herein is not limited to a polypeptide having the exact sequence described herein, but includes proteins having Additionally, the term "Env polypeptide" (e.g., "gp120 polypeptide") encompasses proteins which include additional modifications to the native sequence, such as additional internal deletions, additions and substitutions. These modifications may be deliberate, as through site-directed mutagenesis, or may be accidental, such as through naturally occurring mutational events. Thus, for example, the Env polypeptide to be used in vaccine compositions, the modifications must be such that immunological activity (i.e., the ability to elicit an antibody response to the polypeptide) is not lost.

As used herein, the term "modified Env polypeptide" is an Env polypeptide (e.g., gp120 as defined above), which has been manipulated to delete or replace all or a part of variable regions V1, V1/V2, V1-V3 or V1-V4. Generally, modified Env (e.g., gp120) polypeptides have enough of the variable regions removed to expose the CD4 binding site, but leave enough of the structure to allow correct folding. Although not all possible variable region modifications have been exemplified herein, it is to be understood that other modifications are also encompassed by the present invention. In some embodiments the modified Env polypeptide comprises the amino acid sequence of SEQ ID NO: 4, 6, 8 or 10. In some embodiments the modified Env polypeptide is encoded by the nucleotide sequence of SEQ ID NO: 3, 5, 7 or 9 or a variant thereof.

A variant of a "modified Env polypeptide" or "Env polypeptide" as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both as long as the variant is capable of inducing an immune response. Guidance in determining which amino acid residues may be substituted, inserted, or deleted without abolishing biological or immunological activity may be found using computer programs well known in the art, for example, DNASTAR software. Variants of the present invention include "modified Env polypeptides" or "Env polypeptides" that are at least 80%, preferably 85%, more preferably 90%, even more preferably 95% and most preferably 96%, 97%, 98% or 99% homologous to a reference amino acid sequence.

"HIV" is Human Immunodeficiency Virus, a virus that causes immunodeficiency by attacking CD4+ cells in the body. The present invention is primarily focused on HIV clade C. HIV is organized into groups and subtypes (clades). Guidance on the application of the invention to different clades may also be found in HIV Sequence Compendium 2002 Kuiken C, Foley B, Freed E, Hahn B, Marx P, McCutchan F, Mellors J, Wolinsky S, and Korber B, editors. Published by the Theoretical Biology and Biophysics Group, Los Alamos National Laboratory, LA-UR number 03-3564, incorporated herein by reference. In particular, consensus sequence data for HIV-1 clades A, B, C and D and a number of isolates can be found on pages 490 to 550; consensus sequence data for HIV-2 clades A, B, C and D and a number of isolates can be found one pages 554 to 578.

One embodiment the HIV clade c env polypeptide is encoded by the polynucleotide sequence of SEQ ID NO:1, 3, 5, 7, or 9 or a variant thereof. In other embodiments the HIV clade C env polypeptide has the amino acid sequence of SEQ ID NO:2, 4, 6, 8, or 10 or a variant thereof.

The invention provides methods and compositions for raising an immune response in a subject by administering an HIV antigen. The HIV antigens include HIV clade C polynucleotides and polypeptides. The invention also provides methods and compositions for treating or preventing an HIV infection.

The terms "prevent," "preventing," and "prevention," as used herein, refer to a decrease in the occurrence of HIV in an animal. The prevention may be complete, e.g., the total absence of HIV in a subject. The prevention may also be partial, such that the occurrence of HIV in a subject is less than that which would have occurred without the present invention.

In one aspect, the invention provides for a method of inducing an immune response in a subject comprising administering an HIV clade C envelope polypeptide in an amount sufficient to induce an immune response in the subject. In one embodiment, the polypeptide comprises the amino acid sequence of SEQ ID NO:2. In another embodiment, the HIV clade C envelop polypeptide is modified so that the V1 region is deleted. In some embodiments, the HIV clade C envelope polypeptide is modified so that the V1/V2 regions are deleted. In yet a further, embodiment the polypeptide comprises the amino acid sequence of SEQ ID NO:4. In some embodiments, the HIV clade C envelope polypeptide is modified so that the V1, V2, and V3 regions are deleted. In yet a further, embodiment the polypeptide comprises the amino acid sequence of SEQ ID NO:6. In some embodiments, the HIV clade C envelope polypeptide is modified so that the V1, V2, V3 and V4 regions are deleted. In yet a further, embodiment the polypeptide comprises the amino acid sequence of SEQ ID NO:8. In yet a further embodiment, the method further includes administering a second HIV antigen. The second HIV antigen includes gp120 and gp160.

In another aspect, the invention provides for a method of inducing an immune response in a subject comprising administering a polynucleotide encoding a HIV clade C envelope polypeptide in an amount sufficient to induce an immune response in the subject. In one embodiment, the polynucleotide comprises the nucleotide sequence of SEQ ID NO:1. In another embodiment, the polynucleotide region encoding the V1 region of the HIV clade C envelop polypeptide is modified so that the V1 region is deleted. In some embodiments, the polynucleotide region encoding the V1N2 regions of the HIV clade C envelop polypeptide are modified so that the V1N2 regions are deleted. In yet a further, embodiment the polynucleotide comprises the nucleotide sequence of SEQ ID NO:3. In some embodiments, the polynucleotide regions encoding the V1, V2 and V3 regions of the HIV clade C envelop polypeptide are modified so that the V1, V2 and V3 regions are deleted. In yet a further, embodiment the polynucleotide comprises the nucleotide sequence of SEQ ID NO:5. In some embodiments, the polynucleotide region encoding the V1, V2, V3 and V4 regions of the HIV clade C envelop polypeptide are modified so that the V1, V2, V3 and V4 regions are deleted. In yet a further, embodiment the polynucleotide comprises the nucleotide sequence of SEQ ID NO:7. In yet a further embodiment, the method further includes administering a second HIV antigen. The second HIV antigen includes gp120 and gp160.

In another aspect, the invention provides for isolated and modified HIV clade C envelope polypeptides. In one aspect, the invention provides for an isolated HIV envelope polypeptide. In one embodiment, the polypeptide includes the amino acid sequence of SEQ ID NO:2.

In another aspect, the invention provides a modified HIV clade C envelope polypeptide in which the V1 region is deleted. In another aspect, the invention provides a modified HIV clade C envelope polypeptide in which the V1N2 regions are deleted. In one embodiment, the polypeptide includes the amino acid sequence of SEQ ID NO:4. In another aspect, the invention provides a modified HIV clade C envelope polypeptide in which the V1, V2 and V3 regions are deleted. In one embodiment, the polypeptide includes the amino acid sequence of SEQ ID NO:6. In another aspect, the invention provides a modified HIV clade C envelope polypeptide in which the V1, V2, V3 and V4 regions are deleted. In one embodiment, the polypeptide includes the amino acid sequence of SEQ ID NO:8.

In another aspect, the present invention provides for isolated and modified polynucleotides encoding an HIV envelope polypeptide. In one aspect the invention provides an isolated polynucleotide encoding an HIV clade C envelope polypeptide. In one embodiment, the polynucleotide comprises the nucleotide sequence of SEQ ID NO:1. In another embodiment, the polynucleotide region encoding the V1 region of the HIV clade C envelop polypeptide is modified so that the V1 region is deleted. In some embodiments, the polynucleotide regions encoding the V1/V2 regions of the HIV clade C envelop polypeptide are modified so that the V1/V2 regions are deleted. In yet a further, embodiment the polynucleotide comprises the nucleotide sequence of SEQ ID NO:3. In some embodiments, the polynucleotide regions encoding the V1, V2 and V3 regions of the HIV clade C envelop polypeptide are modified so that the V1, V2 and V3 regions are deleted. In yet a further, embodiment the polynucleotide comprises the nucleotide sequence of SEQ ID NO:5. In some embodiments, the polynucleotide regions encoding the V1, V2, V3 and V4 regions of the HIV clade C envelop polypeptide are modified so that the V1, V2, V3 and V4 regions are deleted. In yet a further, embodiment the polynucleotide comprises the nucleotide sequence of SEQ ID NO:7.

The invention also provides for vectors and compositions which include the HIV clade C envelope polynucleotides and polypeptides of the invention.

In another aspect, the invention provides for an HIV recombinant viral particle. The viral particle has a 1157 ipd envelope region having the nucleotide sequence of SEQ ID NO: 9. In another aspect, the invention provides an HIV recombinant viral particle which includes a 1157 ipd3 envelope region having the nucleotide sequence of SEQ ID NO: 10. In either of the last two aspects the HIV recombinant viral particle may further include the Nef amino acid sequence of SEQ ID NO:11. In further embodiments of the invention, the recombinant viral particle has two or more NF-kB regions. In yet a further embodiment, the HIV recombinant viral particle includes the nucleotide sequence of ATCC VR deposited under the terms of the Budapest Treaty with the American Type Culture Collection (ATCC) of University Boulevard, Manassas, Va. 20110-2209, U.S.A., and granted the above identified accession number. The HIV recombinant viral particles may be include in a composition and may be used in a method for assessing the efficacy of a candidate AIDS vaccine in a subject. The method includes the steps of administering a candidate AIDS vaccine to a non-human primate, infecting the non-human primate with the viral particle and detecting disease progression.

Polypeptides and Polynucleotides of the Invention

A polynucleotide of the present invention may be employed for producing a polypeptide by recombinant techniques. Such a polypeptide may be useful, for example, as an antigen for the induction of an immune response or as a reagent for the affinity purification of such an antibody.

In one embodiment, the polypeptides are generated using recombinant techniques, well known in the art. In this regard, oligonucleotide probes can be devised based on the known sequences of the Env polypeptide genome and used to probe genomic or cDNA libraries for Env genes. The gene can then be further isolated using standard techniques and, e.g., restriction enzymes employed to truncate the gene at desired portions of the full-length sequence. Similarly, the Env gene(s) can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The genes encoding the Env (e.g., full length and variable region deletion) polypeptides can be produced synthetically, based on the known sequences, e.g., sequences disclosed herein. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311; Stemmer et al. (1995) Gene 164:49-53.

Recombinant techniques are readily used to clone a gene encoding an Env polypeptide gene which can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer which hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, Methods Enzymol. (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. Proc. Natl. Acad. Sci. USA (1982) 79:6409.

Once coding sequences for the desired proteins have been isolated or synthesized, they can be cloned into any suitable vector or replicon for expression. A wide variety of vectors encoding modified polypeptides can be generated by creating expression constructs which operably link the polynucleotides of the invention. The construct is then introduced into a host cell for polypeptide expression. Non-limiting examples of such combinations are discussed in the Examples.

Numerous cloning vectors are known to those of skill in the art, and the selection of an appropriate cloning vector is a matter of choice. Examples of recombinant DNA vectors for cloning and host cells which they can transform include the bacteriophage .lambda. (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, DNA Cloning: Vols. I & II, supra; Sambrook et al., supra; B. Perbal, supra.

Insect cell expression systems, such as baculovirus systems, can also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit).

Viral systems, such as a vaccinia based infection/transfection system, as described in Tomei et al., J. Virol. (1993) 67:4017-4026 and Selby et al., J. Gen. Virol. (1993) 74:1103-1113, will also find use with the present invention. In this system, cells are first transfected in vitro with a vaccinia virus recombinant that encodes the bacteriophage T7 RNA polymerase. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired HIV clad C envelope polypeptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as *E. coli*, *Bacillus subtilis*, and *Streptococcus* spp., will find use with the present expression constructs. Yeast hosts useful in the present invention include inter alia, *Saccharomyces cerevisiae, Candida albicans, Candida maltosa,*

*Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica , Bombyx mori, Drosophila melanogaster, Spodoptera frugiperda*, and *Trichoplusia ni.*

Depending on the expression system and host selected, the proteins of the present invention are produced by growing host cells transformed by an expression vector described above under conditions whereby the protein of interest is expressed. The selection of the appropriate growth conditions is within the skill of the art.

In one embodiment, the transformed cells secrete the polypeptide product into the surrounding media. Certain regulatory sequences can be included in the vector to enhance secretion of the protein product, for example using a tissue plasminogen activator (TPA) leader sequence, a .gamma.-interferon signal sequence or other signal peptide sequences from known secretory proteins. The secreted polypeptide product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the HIV clad C envelope polypeptide substantially intact. Intracellular proteins can also be obtained by removing components from the cell wall or membrane, e.g., by the use of detergents or organic solvents, such that leakage of the Env polypeptides occurs. Such methods are known to those of skill in the art and are described in, e.g., Protein Purification Applications: A Practical Approach, (E. L. V. Harris and S. Angal, Eds., 1990).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced Env polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular HIV clad C envelope polypeptides of the present invention involves affinity purification, such as by immunoaffinity chromatography using anti-Env specific antibodies, or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the Env polypeptides can be further purified using conventional techniques well known in the art, such as by any of the techniques described above.

Relatively small polypeptides, i.e., up to about 50 amino acids in length, can be conveniently synthesized chemically, for example by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis. Synthesis. Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis, Synthesis, Biology, Vol. 1, for classical solution synthesis.

The polypeptides of the present invention can also be chemically prepared by other methods such as by the method of simultaneous multiple peptide synthesis. See, e.g., Houghten Proc. Natl. Acad. Sci. USA (1985) 82:5131-5135; U.S. Pat. No. 4,631,211.

Pharmaceutical Preparations

In one embodiment the antigens of the invention are present in pharmaceutical preparations. Generally they are in the form of a polypeptide which can be prepared by the various methods describe herein and known in the art. In some embodiments, the antigens are provided as polynucleotides encoding the antigen.

The HIV clade C envelope polypeptides and the polynucleotides encoding them are useful, for example, as vaccine compositions. Compositions of the invention can be used as vaccine compositions, for example, to enhance or induce an immune response of a subject to a HIV. Immune responses which can be enhanced or induced include both humoral and cell-mediated responses. Compositions comprising particular preparations of HIV clade C envelope molecules can be tested for the ability to induce an immune response using assays well known in the art. For example, a composition can be injected into a laboratory animal, such as a rat or mouse, and the animal can be monitored for the appearance of immune reactants, such as antibodies, directed against the Env polypeptide. Alternatively, assays such as cytotoxic T lymphocyte assays can be performed to determine whether a particular composition of Env molecule is immunogenic.

For use as a vaccine, a composition of the invention preferably comprises a HIV clade C envelope polypeptide or a modified HIV clade C envelope polypeptide. Vaccine compositions of the invention typically comprise a physiologically compatible carrier. Physiologically compatible carriers are well known to those in the art. Such carriers include, but are not limited to, a simple low salt solution which permits preservation of the integrity of the Env polypeptide, e.g., 10 mM NaCl, 0.1 mM EDTA, or to large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in Env compositions, for example, mineral salts such as hydrochlorides, hydrobromides, phosphates, or sulfates, as well as salts of organic acids such as acetates, proprionates, malonates, or benzoates. Compositions of the invention can also contain liquids, such as water, saline, glycerol, and ethanol, as well as substances such as wetting agents, emulsifying agents, or pH buffering agents.

Various methods can be used to administer an HIV clade C envelope molecule vaccine composition to a human, including intravenous, intramuscular, or subcutaneous injection. Vaccine compositions of the invention are administered at a dose effective to induce an immune response against the Env polypeptide. The particular dosages of the composition used to enhance an immune response will vary, for example, according to the Env compositions being used and the mammal to which the composition is administered. Generally, about 5 ug to about 50 ug of Env polypeptide per kg of patient body weight, about 50 ug to about 5 mg/kg, about 100 ug to about 500 ug/kg, or about 200 to about 250 ug/kg will be administered to an adult human. Such ranges by no means preclude use of a higher or lower amount of a component, as might be warranted in a particular application. For example, the actual dose and schedule may vary depending on whether the compositions are administered in combination with other pharmaceutical compositions, or depending on individual differences in pharmacokinetics, drug disposition, and metabolism.

The antigens and/or adjuvants of the invention can also be delivered using one or more gene vectors, administered via nucleic acid immunization or the like using standard gene delivery protocols. Methods for gene delivery are known in the art. See, e.g., U.S. Pat. Nos. 5,399,346, 5,580,859, 5,589,466. The constructs can be delivered either subcutaneously, epidermally, intradermally, intramuscularly, intravenous, mucosally (such as nasally, rectally and vaginally), intraperitoneally, orally or combinations thereof.

An exemplary replication-deficient gene delivery vehicle that may be used in the practice of the present invention is any of the alphavirus vectors, described in, for example, U.S. Pat. Nos. 6,342,372; 6,329,201 and International Publication WO 01/92552.

A number of viral based systems have been developed for gene transfer into mammalian cells. For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, BioTechniques (1989) 7:980-990; Miller, A. D., Human Gene Therapy (1990) 1:5-14; Scarpa et al., Virology (1991) 180:849-852; Burns et al., Proc. Natl. Acad. Sci. USA (1993) 90:8033-8037; and Boris-Lawrie and Temin, Cur. Opin. Genet. Develop. (1993) 3:102-109.

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476).

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al. Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering polynucleotides, mucosally and otherwise, is the enterically administered recombinant poxvirus vaccines described by Small, Jr., P. A., et al. (U.S. Pat. No. 5,676,950, issued Oct. 14, 1997, herein incorporated by reference) as well as the vaccinia virus and avian poxviruses. By way of example, vaccinia virus recombinants expressing the genes can be constructed as follows. The DNA encoding the antigens and/or adjuvants of the invention is first inserted into an appropriate vector so that it is adjacent to a vaccinia promoter and flanking vaccinia DNA sequences, such as the sequence encoding thymidine kinase (TK). This vector is then used to transfect cells that are simultaneously infected with vaccinia. Homologous recombination serves to insert the vaccinia promoter plus the gene encoding the coding sequences of interest into the viral genome. The resulting TK recombinant can be selected by culturing the cells in the presence of 5-bromodeoxyuridine and picking viral plaques resistant thereto.

Alternatively, avipoxviruses, such as the fowlpox and canarypox viruses, can also be used to deliver genes encoding the antigens and/or adjuvants of the invention. Recombinant avipox viruses, expressing immunogens from mammalian pathogens, are known to confer protective immunity when administered to non-avian species; The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545. Picornavirus-derived vectors can also be used. (See, e.g., U.S. Pat. Nos. 5,614,413 and 6,063,384). Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

A vaccinia based infection/transfection system can be conveniently used to provide for inducible, transient expression of the coding sequences of interest (for example, sequences encoding the antigens or adjuvants of the invention) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase that in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200: 1201-1206; Gao and Huang, Nuc. Acids Res. (1993) 21:2867-2872; Chen et al., Nuc. Acids Res. (1994) 22:2114-2120; and U.S. Pat. No. 5,135,855.

One or more additional HIV antigens can be used in the vaccine and methods of this invention. For instance, the HIV clad C env antigens can be used with additional HIV antigens. The additional HIV antigens may be administer simultaneously, prior or after administration of the HIV clad C env antigen.

In addition, an immuno-modulatory factor may be added to the pharmaceutical composition. An "immuno-modulatory factor" refers to a molecule, for example a protein that is capable of modulating an immune response or DNA vectors encoding a given immuno-modulatory factor. Non-limiting examples of immunomodulatory factors include lymphokines (also known as cytokines), such as IL-6, TGF-beta, IL-1, IL-2, IL-3, etc.); and chemokines (e.g., secreted proteins such as macrophage inhibiting factor). Certain cytokines, for example TRANCE, flt-3L, and a secreted form of CD40L are capable of enhancing the immunostimulatory capacity of APCs. Non-limiting examples of cytokines which may be used alone or in combination in the practice of the present invention include, interleukin-2 (IL-2), stem cell factor (SCF), interleukin 3 (IL-3), interleukin 6 (IL-6), interleukin 12 (IL-12), G-CSF, granulocyte macropliage-colony stimulating factor (GM-CSF), interleukin-1 alpha (IL-1.alpha.), interleukin-11 (IL-11), MIP-1.gamma., leukemia inhibitory factor (LIF), c-kit ligand, thrombopoietin (TPO), CD40 ligand (CD40L), tumor necrosis factor-related activation-induced cytokine (TRANCE) and flt3 ligand (flt-3L). Cytokines are commercially available from several vendors such as, for example, Genzyme (Framingham, Mass.), Amgen (Thousand Oaks, Calif.), R&D Systems and Immunex (Seattle, Wash.). The sequences of many of these molecules are also available, for example, from the GenBank database. It is intended, although not always explicitly stated, that molecules having similar biological activity as wild-type or purified cytokines (e.g., recombinantly produced or mutants thereof) and nucleic acid encoding these molecules are intended to be used within the spirit and scope of the invention.

The compositions of the invention will typically be formulated with pharmaceutically acceptable carriers or diluents. As used herein, the term "pharmaceutically acceptable carrier" refers to a carrier for administration of the antigens which does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; McGee et al. (1997) J. Microencapsul. 14(2):197-210; O'Hagan et al. (1993) Vaccine 1 (2):149-54. Such carriers are well known to those of ordinary skill in the art. Additionally, these carriers may function as immunostimulating agents ("adjuvants"). Furthermore, the antigen may be conjugated to a bacterial toxoid, such as toxoid from diphtheria, tetanus, cholera, etc., as well as toxins derived from *E. coli.*

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of acceptable excipients is available in the well-known Remington's Pharmaceutical Sciences.

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

Administration

The compositions disclosed herein can be administered to a subject to generate an immune response. Preferably, the composition can be used as a vaccine to treat or prevent HIV infection.

As used herein, "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

The compositions will include “immunologically effective amounts” of HIV antigen i.e. amounts sufficient to raise a specific immune response or, more preferably, to treat, reduce, or prevent HIV infection. An immune response can be detected by looking for antibodies to the HIV antigen used (e.g. IgG or IgA) in patient samples (e.g. in blood or serum, in mesenteric lymph nodes, in spleen, in gastric mucosa, and/or in feces). The precise effective amount for a given patient will depend upon the patient’s age, size, health, the nature and extent of the condition, the precise composition selected for administration, the patient’s taxonomic group, the capacity of the patient’s immune system to synthesize antibodies, the degree of protection desired, the formulation of the vaccine, the treating physician’s assessment of the medical situation, and other relevant factors. Thus, it is not useful to specify an exact effective amount in advance, but the amount will fall in a relatively broad range that can be determined through routine trials, and is within the judgment of the clinician. For purposes of the present invention, an effective dose will typically be from about 0.01 mg/kg to 50 mg/kg in the individual to which it is administered.

EXAMPLES

Example 1

V-loop deleted SHIV envC Induces Cross-Clade nAb Responses in Mice

A V-loop deleted SHIV-1157ipenv expression vector was prepared as follows: the entire SHIV-1157ip gp160 sequence was codon-optimized and cloned into the pTPS mutagenesis vector (Xu et al., 2002). Mutagenic primers were used to separately delete the V1/V2 loops and the V3 loop. The mutagenic primers were synthesized and included linker sequences GAG to maintain the Env core structure (Johnson et al., 2002). Mutagenesis was confirmed by DNA sequencing and the mutant gp160 gene was cloned into the pJW4303 expression vector. The resulting plasmid, pJW1157ipenvΔ123 was tested for purity by restriction digest/gel electrophoresis and for in vitro expression by transfection into 293T cells followed by Western blot analysis. The Western blot analysis showed a protein band of approximately 135 kb.

A recombinant vaccinia virus was made expressing 1157ipenvΔ123 and used to infect the human osteosarcoma cell line, 143 B. SHIV-1157ipΔ123 Env was prepared from cell lysates by size-exclusion and lentil-lectin chromatography (Earl et al., 1994).

Figure 3:
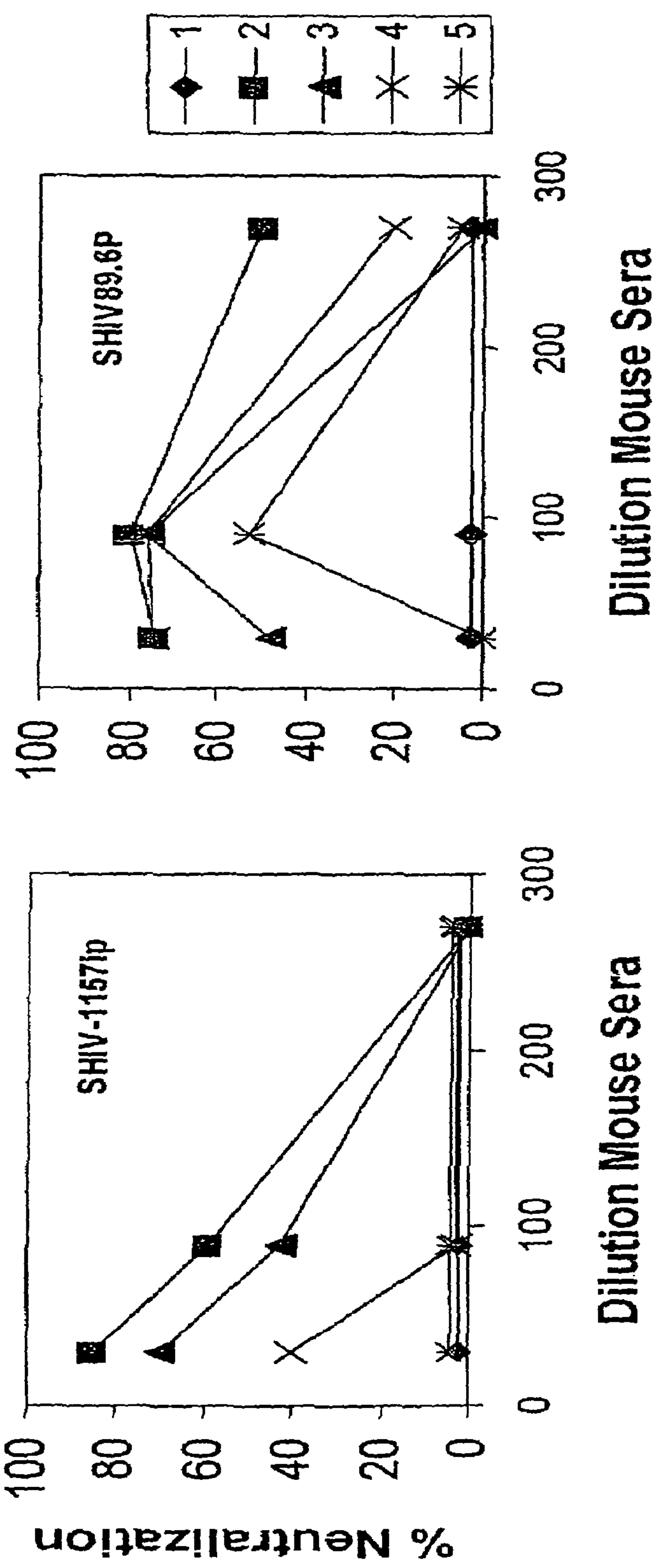
FIG. 3 illustrates neutralizing antibody activity against SHIV-1157ip and SHIV89.6P.

Five BALB/c mice were inoculated subcutaneously 2× with 20 ug of SHIV-1157ipΔ123 Env formulated in MPL+TDM emulsion. Sera from immunized mice were tested for neutralizing antibody activity against homologous SHIV-1157ip and against heterologous SHIV89.6P (FIG. 3). Three of 5 mice showed neutralizing antibody activity against SHIV-1157ip and 4 of the 5 mice showed neutralizing antibody activity against heterologous SHIV89.6P clade B.

The results demonstrate that immunization with a multiply V-loop deleted clade C Env, prepared from the full-length gp160 genome by methodology that maintains structural integrity of the multimeric form of the Env glycoprotein, is immunogenic and can induce cross-clade nAb responses.

Example 2

Construction and Adaptation of SHIV-1157i to Rhesus Macaques

A biologically relevant challenge virus was created to evaluate anti-HIV clade C immune prophylaxis.

SHIV-1157i Construction.

Figure 19A:
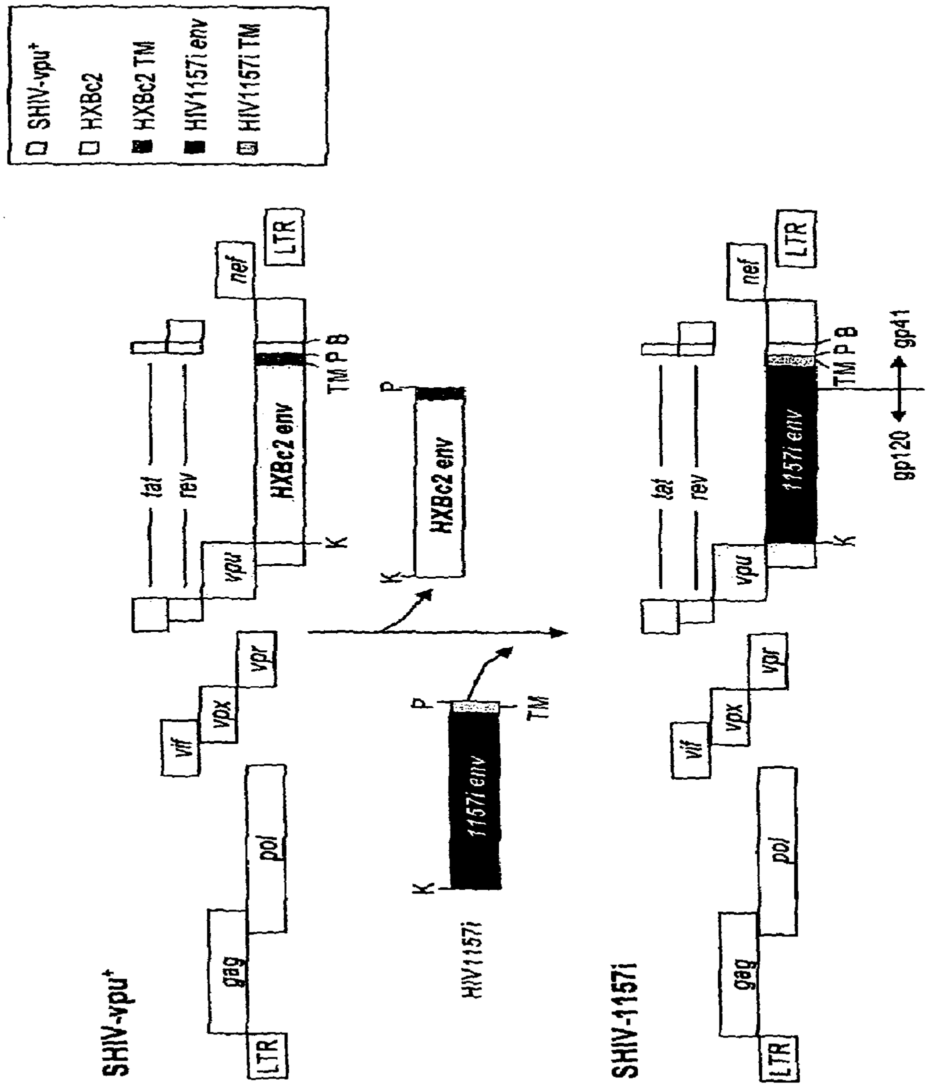
FIG. 19 illustration of the cloning strategy for SHIV-1157i.

SHIV-1157i was built upon the backbone of SHIV-vpu$^+$ (Li et al., *J. Virol*. (1995), 69; 7061-67) (FIG. 19*a*) and contained most of gp120 as well as the entire extracellular domain and transmembrane region of gp41 of the primary, original HIV 1157i isolate. The HIV 1157i isolate is a recently transmitted pediatric HIV clade C isolate from a six-month-old Zambian infant.

The initial cell-free SHIV-1157i stock was generated by transfecting 293T cells with proviral DNA and harvesting the supernatants. The virus replicated in human and rhesus monkey PBMC and in Ghost.CD4.CCR5.GFP cells but did not infect CEMx174 or CEMx174.GFP cells, which do not express CCR5, indicating that SHIV-1157i, like the original HIV1157i, uses CCR5 as coreceptor.

Adaptation of SHIV-1157i to Rhesus Macaques

Figure 19B:
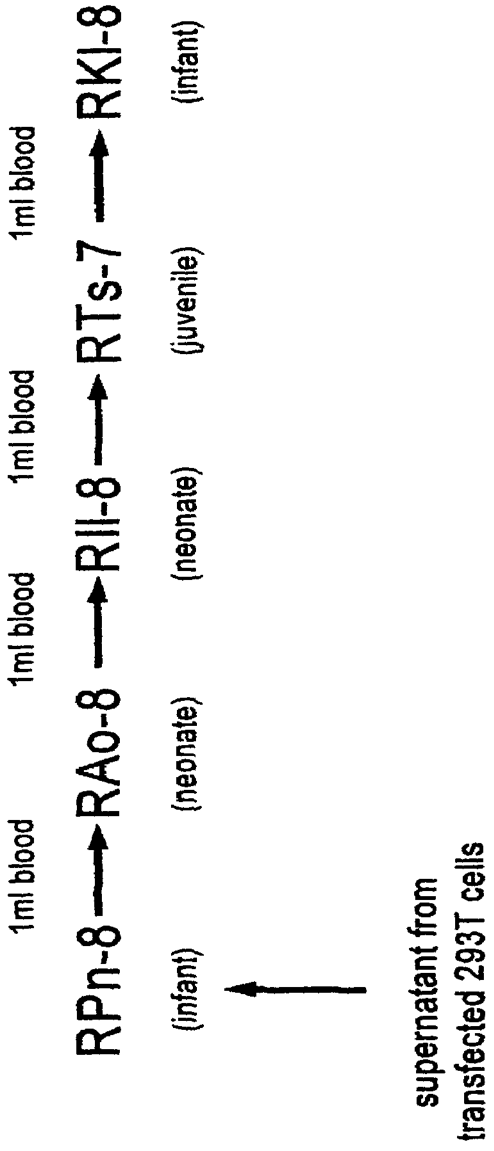
Figure 19C:
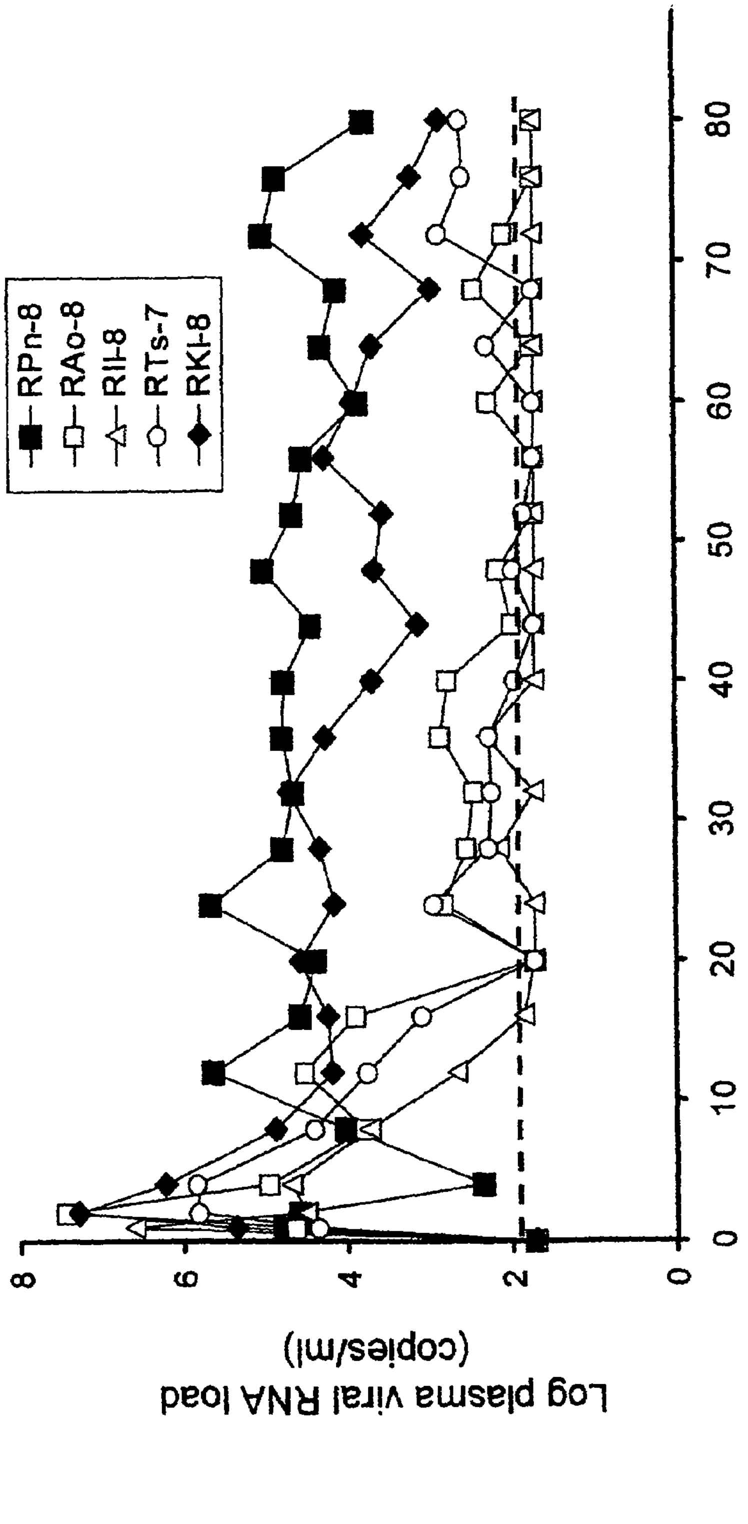

To adapt SHIV-1157i to rhesus macaques, infant rhesus monkey RPn-8 was inoculated intravenously (i.v.) with 6 ml of virus. Real-time RT-PCR revealed that SHIV-1157i replicated in this animal; peak viremia reached $6\times10^4$ RNA copies/ml at week 4 post-inoculation (p.i.). This first animal never cleared the virus and remained viremic throughout. Four additional animals were subjected to serial blood transfer (FIG. 19*b*), whereby 1 ml of whole blood collected at peak viremia (week 2 p.i.) was directly transferred into the following monkey recipients: neonates RAo-8 and RIl-8, juvenile RTs-7 and infant RKl-8. Compared to the first virus recipient RPn-8, peak viral RNA loads increased between 1 to 2 logs in subsequent recipients (FIG. 19*c*). All five monkeys in this cohort seroconverted by week 4. At week 6 p.i., the passaged virus, termed SHIV-1157ip, was isolated from PBMC of the last recipient, RKl-8, and a large stock was grown in rhesus monkey PBMC. Virus from this stock was replication-competent in PBMC of other naïve rhesus monkey donors.

SHIV-1157ip replicated neither in CEMx174 or CEMx174-GFP cells nor in U87.CD4, or U87.CD4 cells expressing CCR1, CCR2, CCR3, or CXCR4. SHIV-1157ip also failed to replicate in Ghost-BOB and Ghost-Bonzo cells. Productive infection was only observed in U87.CD4.CCR5 cells, indicating that SHIV-1157ip exclusively used CCR5 as coreceptor, even after several passages in a different species.

Example 3

Pathogenicity of SHIV-1157ip

Figure 4A:
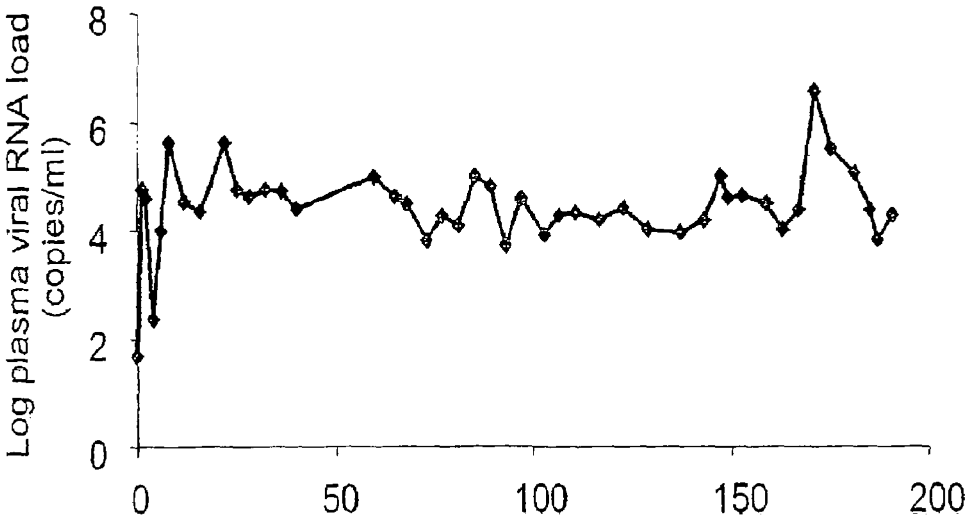
FIG. 4 illustrates CD4+T cell counts and vial RNA loads in Rhesus Monkeys.
Figure 4B:
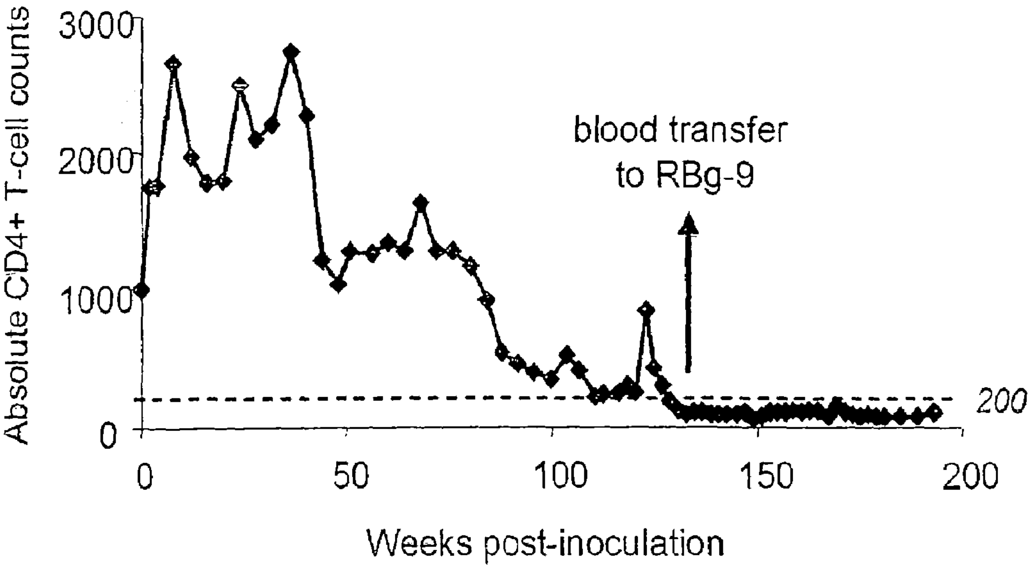

Signs of early disease (depletion of memory T cells in peripheral blood and persistently low $CD4^+/CD8^+$ ratios) were observed in two monkeys, RPn-8 and RKl-8, within the first year post-inoculation. This was followed by depletion of absolute $CD4^+$ T cells in peripheral blood. In animal RPn-8, AIDS, as defined by $CD4^+$ T cells persistently <200 cells/μl, developed at week 135 p.i.; in two other animals, RKl-8 and RTs-7, absolute $CD4^+$ T-cell counts have persistently been <500 cells/μl (FIG. 4). As an additional sign of lentivirus-induced disease, severe, persistent thrombocytopenia has developed in animal RPn-8, although no bleeding has been observed to date.

In order to determine whether a more aggressive virus had evolved in animal RPn-8 after it had developed AIDS, 10 ml of blood was transfused into a naïve recipient, RBg-9. Three months later, this recipient animal developed thrombocytopenia and depletion of peripheral blood memory T cells. Both of these abnormalities have persisted over the ensuing 18 months. Both donor and recipient have remained persistently viremic.

Example 4

Construction and Mucosal Trans-Mission of SHIV-1157ipd3N4

Figure 5:
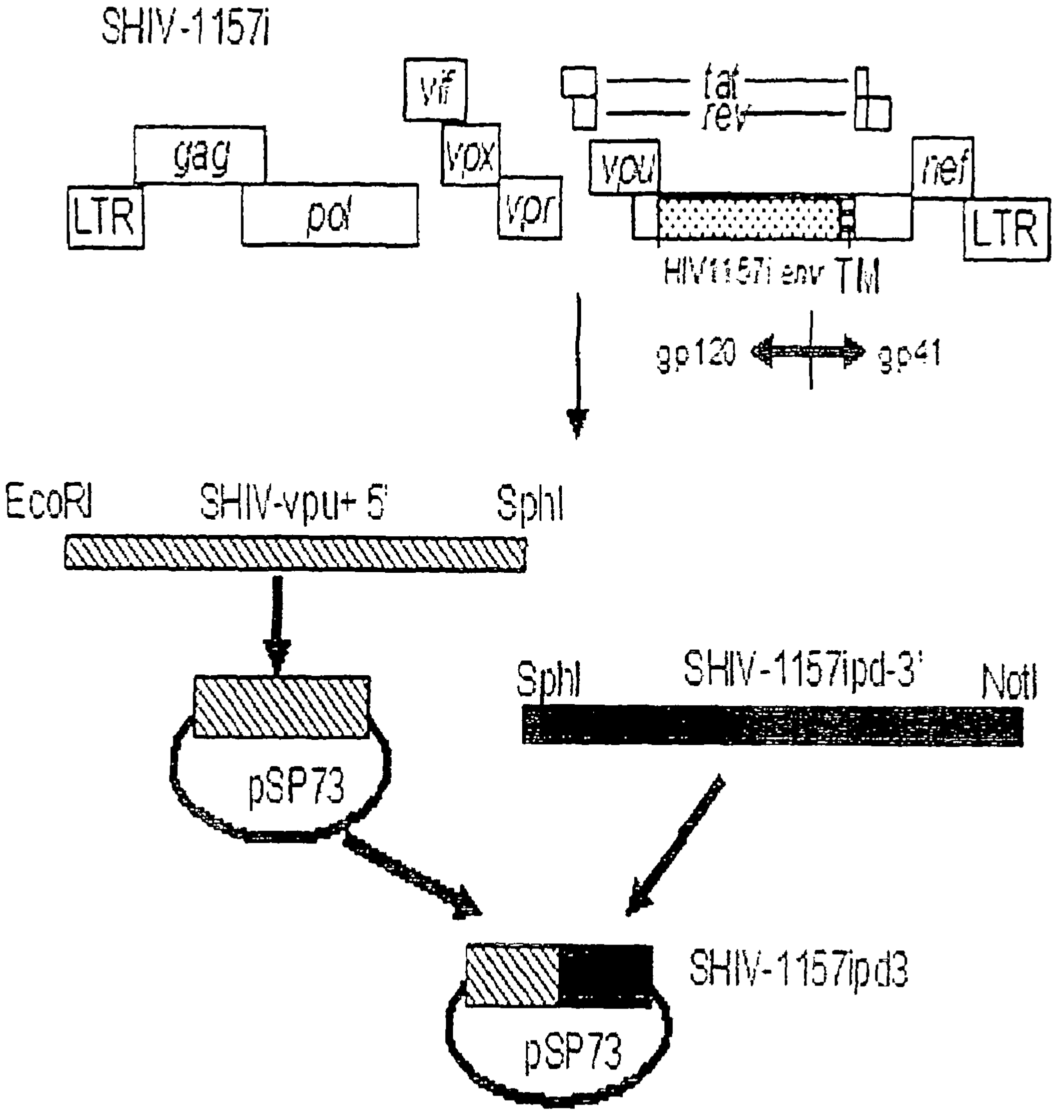
FIG. 5 illustrates construction of SHIV-1157ipd3.

After the first SHIV-1157i-infected monkey (RPn-8) had progressed to AIDS, the virus was re-isolated in order to generate another molecular clone. The re-isolated virus, termed SHIV-1157ipd, was isolated four weeks after animal RPn-8's absolute $CD4^+$ T-cell count dropped to <200 cells/μl. Clone 3 gave rise to the highest level of infectious virus and was selected for further studies (FIGS. 4, 5). Genetic analysis of SHIV-1157ipd env sequences revealed a number of mutations that resulted in single amino acid substitutions in gp120, especially in V1, V2 and V4. Mutations were also observed in gp41. Five out of five clones sequenced contained a 118-bp deletion in the 3' end of env. This 118-bp deletion was located in the intracellular domain of gp41 and led to a loss of 35 of the original amino acids (aa), and due to a frame shift, a gain of 57 aa. The envelope remained infectious.

Figure 6A:
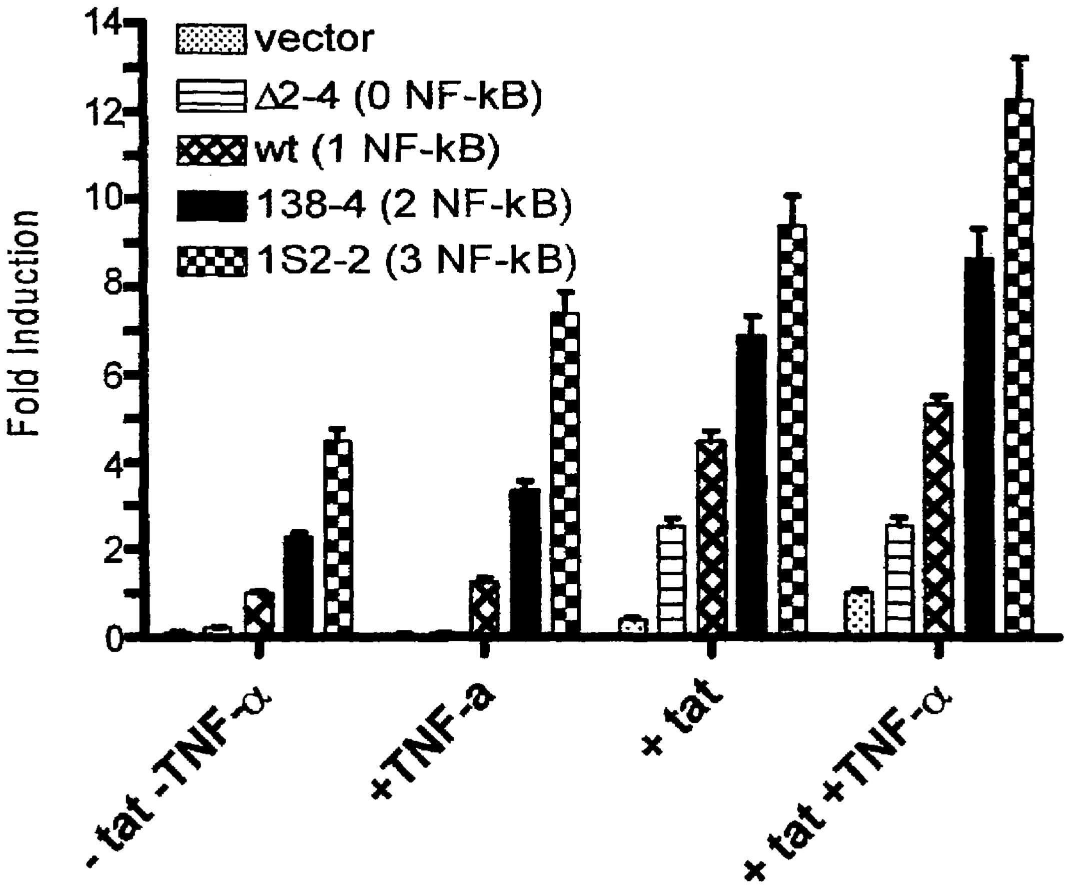
FIG. 6 illustrates luciferase expression levels in constructs with increasing numbers of NF-κB sites and replication of SHIV-1157ipd3 v. SHIV-1157ipd3N4.
Figure 6B:
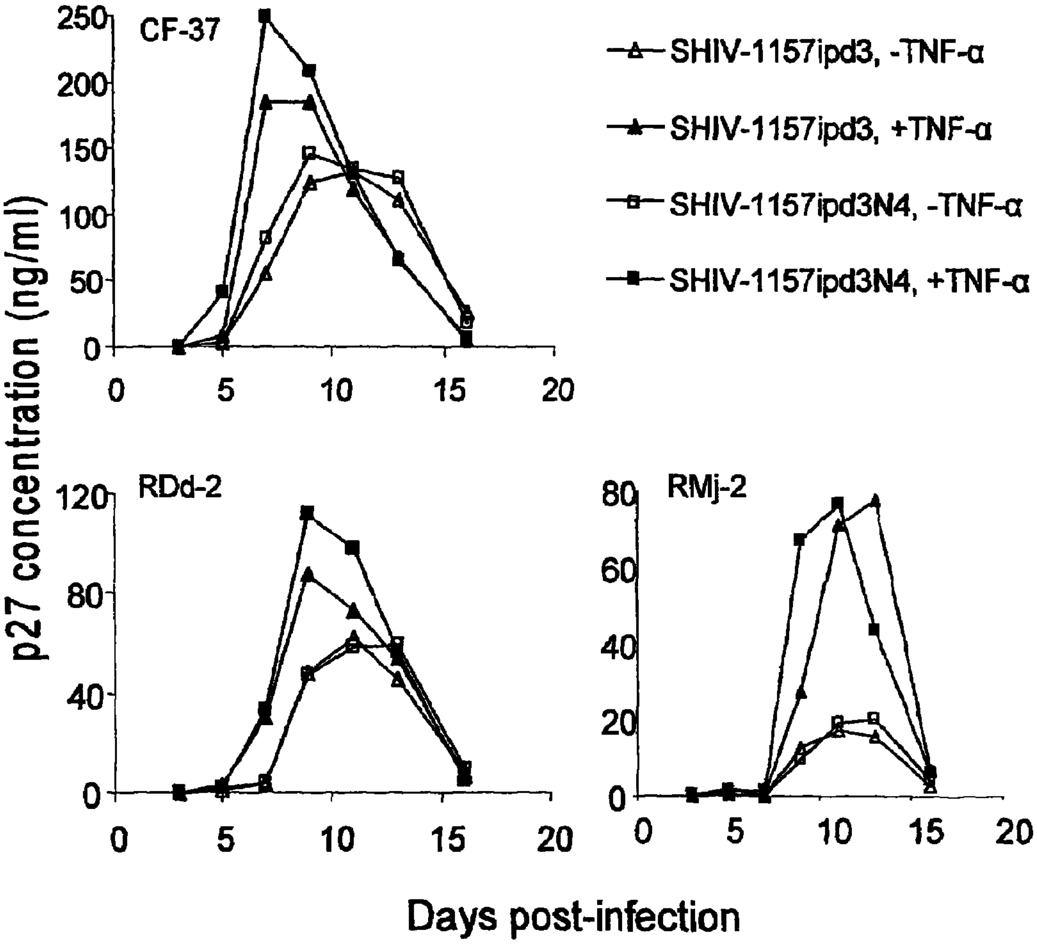

In order to maximize the replicative capacity and enhance viral loads in vivo, transcriptional control elements in the lentiviral LTR were added. Thus, the LTR of SHIV-1157ipd3 was modified to increase the number of NF-κB sites. In a set of solo-LTR constructs linked to the luciferase reporter gene, a direct correlation between LTR-mediated gene expression and the number of NF-κB sites in transient transfection assays was demonstrated (FIG. 6*a*). The effect was especially pronounced when a tat expression plasmid was cotransfected and TNF-α was added to the medium, consistent with the signal transduction cascade activated by this cytokine. After transfection and release of infectious virus, the modifications engineered into the 3' LTR will be copied into the 5' LTR in the subsequent viral replication cycle. The replication kinetics of late-stage viruses encoding two NF-κB sites produced higher levels of p27 Gag production and/or earlier peaks to stimulation with TNF-α than virus containing only one site (FIG. 6*b*).

Figure 7A:
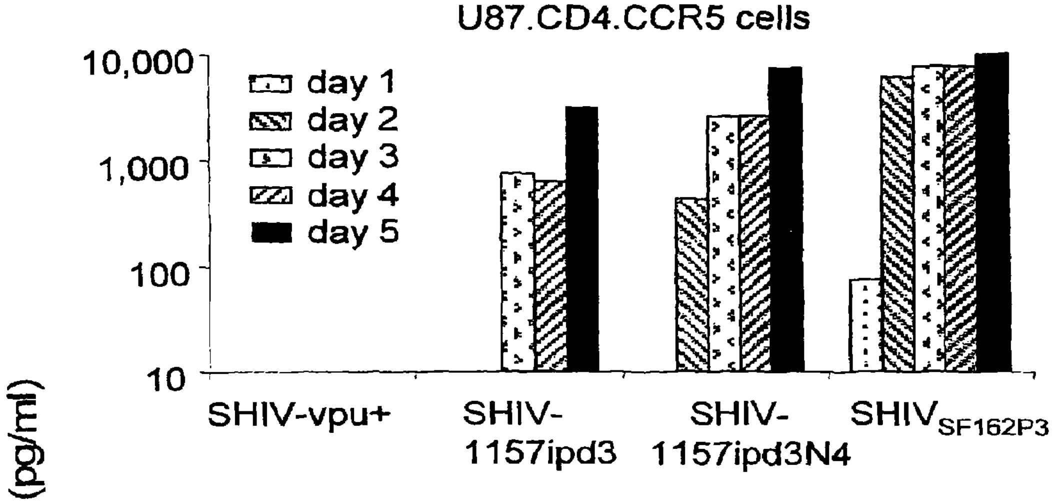
FIG. 7*a* illustrates coreceptor usage of SHIV-1157ipd3 and SHIV-1157ipd3N4.

The SHIV-1157ipd3 virus replicated neither in CEMx174 or CEMx174-GFP cells nor in U87.CD4, U87.CD4.CCR1, U87.CD4.CCR2, U87.CD4.CCR3, U87.CD4.CXCR4, GHOST-BOB and GHOST-BONZO cells. Productive infection occurred only in U87.CD4.CCR5 cells (FIG. 7*a*), indicating that late-stage SHIV-1157ipd3 and its 2 NF-κB-site counterpart, SHIV-1157ipd3N4, still use CCR5 as coreceptor exclusively.

Figure 7B:
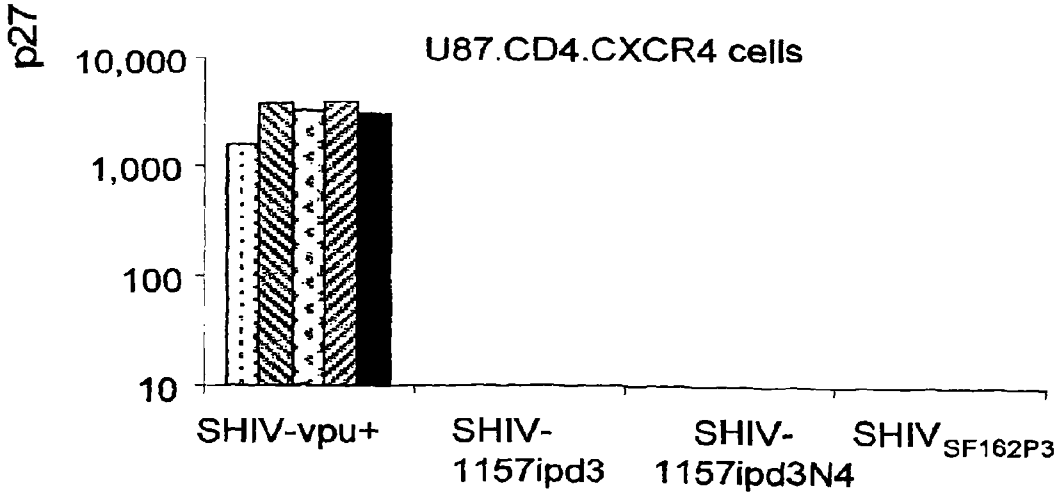
FIGS. 7*b* and *c* illustrate virus neutralization with several broadly reactive human nmAbs: b12, 2G12, 2F5 and 4E10, and b12, 2G12, 2F5, 4E10 and 4X, respectively.
Figure 7C:
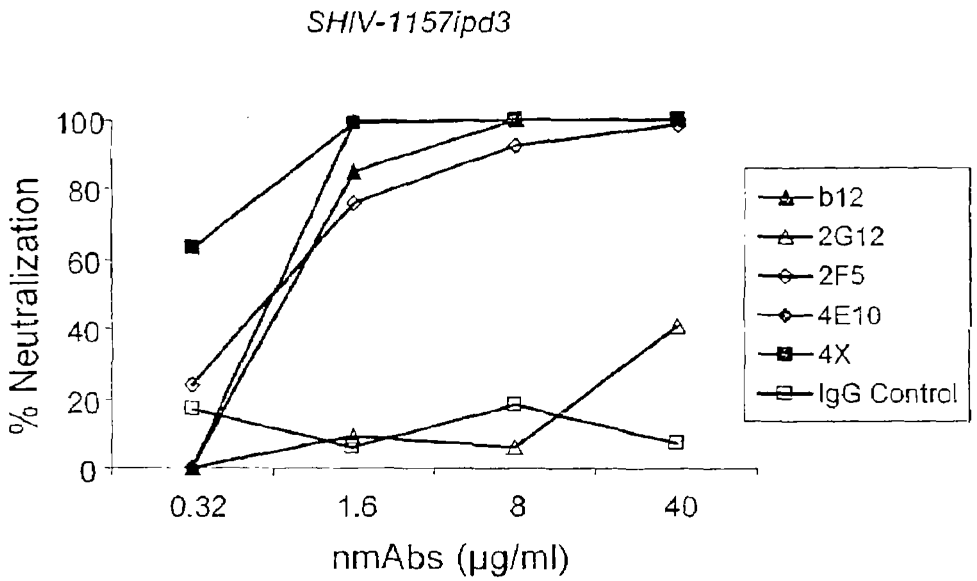

In order to determine whether late virus was susceptible to neutralization by the broadly reactive human nmAbs b12, 2G12, 2F5 and 4E10 (FIG. 7*b*) assays were performed in human PBMC. The late virus had lost its sensitivity to 2G12 which was correlated with the loss of a key N-linked glycosylation site at aa position 295 that is required for forming the complex 2G12 epitope (Scanlan et al., 2002); the 2G12 nmAb is unique in that it is targeted to a pure carbohydrate structure that consists of several mannan residues. Nevertheless, the late SHIV-1157ipd3N4 had not developed global neutralization resistance.

Thus, several SHIV envC strains were prepared that encode one of various forms of the env gene that was originally cloned from the R5 HIV 1157i, a clade C strain. This virus was isolated from a Zambian child who turned out to be a long-term non-progressor (LTNP) during the prospective follow-up. The SHIV constructs and their designations are as follows:

SHIV-1157i infectious molecular clone, not yet adapted to rhesus monkeys; "i" designates a virus strain (or env gene) isolated from an infant SHIV-1157ip biological isolate obtained after passage through several rhesus monkeys; "p" designates a passaged, monkey-adapted virus SHIV-1157ipd biological isolate, "d" indicates that the virus was re-isolated from an infected monkey with disease SHIV-1157ipd3 infectious molecular clone #3. The 3' half of the provirus was derived from a monkey with virus-induced disease SHIV-1157ipd3N4 identical to SHIV-1157ipd3 except that each LTR has 2 instead of the usual 1 NF-κB sites.

Example 5

Testing Vaccination in Animals Challenged with SHIV-1157ipd3N4

Figure 20:
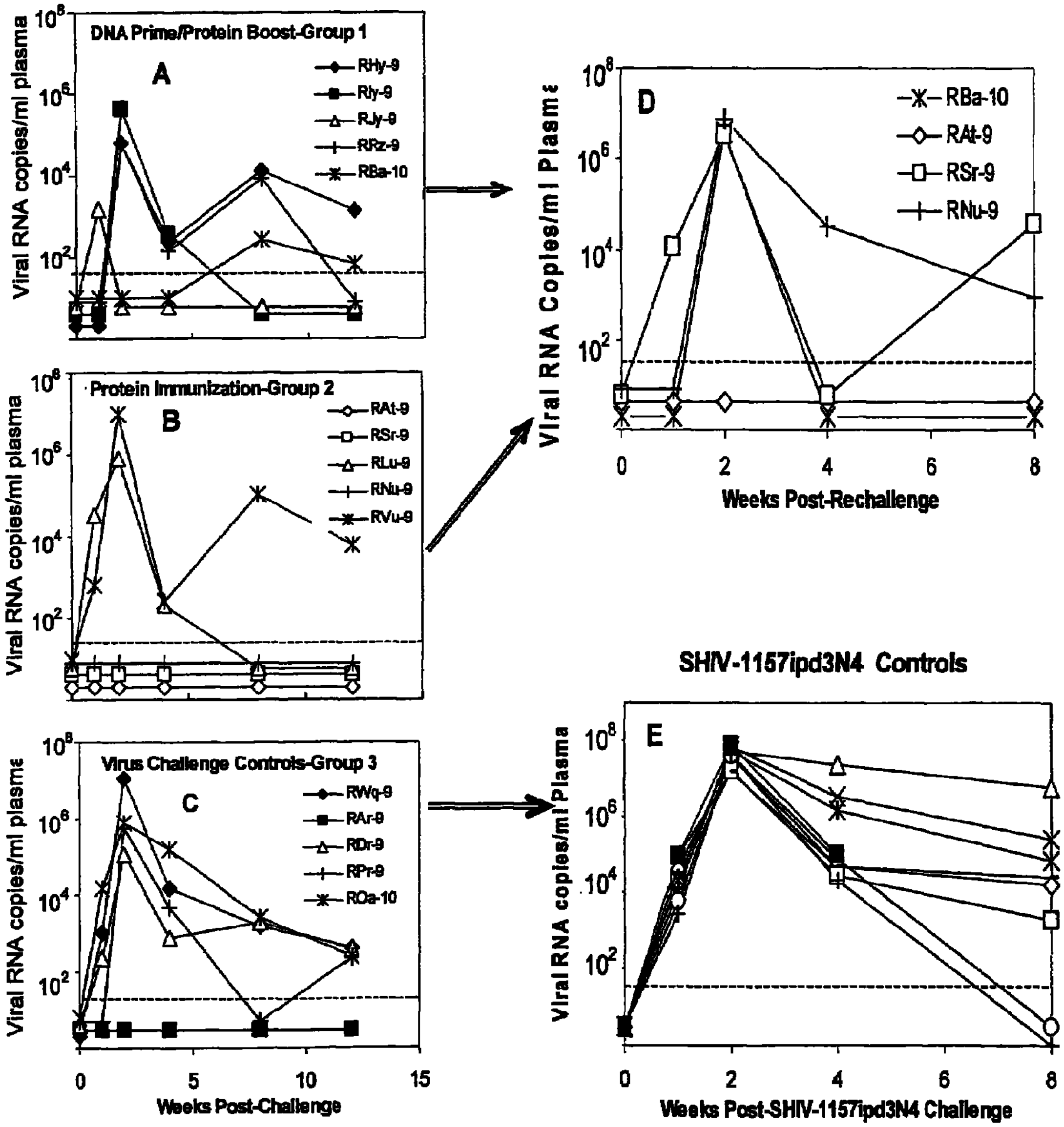
FIG. 20 illustration of viremia in vaccinated and control macaques.

Two groups of newborn macaques were vaccinated (Group 1 and Group 3). Group 1 animals were given a combination of DNA expression plasmids encoding SIVgag-proteasel, HIVtat and HIV1084ienv. Group 3 animals (controls) were given empty vector DNA. DNA was given at 2 time points—at birth and at 6 weeks. Animals were rested and then given soluble protein boosts consisting of SIV Gag-Pol particles derived from recombinant vaccinia virus infected cells, HIV Tat and HIV1084i gp160. Age-matched Group 2 animals were given soluble proteins with no DNA priming. Proteins were given at month 9, month 11 and at month 24. Cellular and humoral immunity were assessed 2 weeks after each vaccination time point. The animals were challenged orally with SHIV-1157ip (FIG. 20, panels A, B and C). All RM received a relatively low-dose of 3.7 $AID_{50}$ which could account for less than 100% infection among controls. In vitro, $CD8^+$ T cell-depleted PBMC from RM that had remained uninfected after oral challenge, were fully susceptible to SHIV-1157ip and SHIV-1157ipd3N4 infection, thus ruling out inherent resistance to these viruses.

Because some vaccines appeared to have contained SHIV-1157ip, they were re-challenged i.r. with 20 $AID_{50}$ of SHIV-1157ipd3N4. The rechallenged animals included one animal from Group 1 (DNA prime/protein boost), 3 animals from Group 2 (protein immunization alone), and one animal from the control group, RAr-9. Plasma vRNA levels for RAr-9 after rechallenge (FIG. 20E, red) and for a group of 8 additional non-vaccinated control animals identically challenged with SHIV-1157ipd3N4 are shown. By week 1, all control animals were infected, and peak viremia levels ranged from $1.3\text{–}7.7\times10^7$ vRNA copies/ml. In contrast, only 1 of 4 previously vaccinated RM had detectable virus by wk 1 (FIG. 20D). Of those that became infected, peak viremia levels were a log lower than in controls ($p=0.003$). Importantly, one of the protein-only vaccinated animals, RAt-9, still had no evidence of infection after rechallenge with SHIV-1157ipd3N4. At the time of rechallenge, this RM had strong cellular immunity to SIV Gag and HIV Tat.

To conserve RM, the rechallenge described was piggy-backed with i.r. SHIV-1157ipd3N4 challenge of the vaccines. All RM in the 3 vaccine groups became infected, but mean peak viremia levels for animals of the 3 vaccine groups combined were significantly less than controls ($2.4\times10^7$ vs $4.0\times$ $10^7$ vRNA copies/ml; p=0.006). Mean plasma viremia levels for the Group 3 RM alone that were DNA primed with clade C env and boosted with heterologous clade B gp160 were the lowest at $1.5\times10^7$ RNA copies/ml (p=0.014).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

The invention claimed is:

1. An isolated HIV envelope polypeptide, wherein said polypeptide comprises an amino acid sequence selected from the group consisting of SEQ ID NOS.:2, 4, 6, 8 and 10.

2. A composition comprising said HIV envelope polypeptide of claim 1 and a pharmacologically acceptable carrier.

3. An isolated polynucleotide encoding the HIV envelope polypeptide of claim 1.

4. A construct comprising said HIV envelope polynucleotide of claim 3.

5. A composition comprising said HIV envelope polynucleotide of claim 4 and a pharmacologically acceptable carrier.

6. A method for inducing an anti-human immunodeficiency virus (HIV) immune response in a subject in need thereof, wherein said method comprises administering an immunogenic composition comprising the polypeptide of claim 1 to said subject.

7. The method of claim 6, further comprising administering a second HIV antigen.

8. The method of claims 7, wherein said second HIV antigen is Gp120 or gp160.

9. The method of claim 6, wherein said immune response treats an HIV infection.

10. An HIV recombinant viral particle comprising the polypeptide of claim 1.

11. The HIV recombinant viral particle of claim 10, wherein said viral particle further comprises the Nef amino acid sequence of SEQ ID NO:11.

12. The recombinant viral particle of claim 10, wherein said viral particle comprises two or more NF-κB regions.

* * * * *

UNITED STATES PATENT AND TRADEMARK OFFICE

CERTIFICATE OF CORRECTION

PATENT NO. : 8,603,490 B2
APPLICATION NO. : 12/286159
DATED : December 10, 2013
INVENTOR(S) : Ruth M. Ruprecht It is certified that error appears in the above-identified patent and that said Letters Patent is hereby corrected as shown below:

Specification

At column 1, lines 18-20, the sentence, "The invention was supported, in whole or in part, by a grant P01 AI48240 from the National Institutes of Health-NIAID. The Government has certain rights in the invention." should read: "This invention was made with government support under grant number AI048240 awarded by The National Institutes of Health. The government has certain rights in the invention."

Signed and Sealed this
Twentieth Day of September, 2016

Michelle K. Lee
*Director of the United States Patent and Trademark Office*

SEQUENCE LISTING

```
<160> NUMBER OF SEQ ID NOS: 16

<210> SEQ ID NO 1
<211> LENGTH: 2547
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

atgcgcgtga aggagaagta ccagcacctg tggcgctggg gctggcgctg gggcaccatg     60

ctgctgggca tgctgatgat ctgctccgcc accgagaagc tgtgggtgac cgtgtactac    120

ggcgtgcccg tgtggaagga ggccaagacc accctgttct gcgcctccga cgccaaggcc    180

tacgagaagg aggtgcacaa catctgggcc acccacgcct gcgtgcccac cgaccccaac    240

ccccaggaga tcgtgctgga gaacgtgacc gagaacttca acatgtggaa ggacgacatg    300

gtggaccaga tgcacgagga catcatctcc ctgtgggacc agtccctgaa gccctgcgtg    360

aagctgaccc ccctgtgcgt gaccctgaag tgctccaact tcacccgcga gggcaacgtg    420

acctacaagg aggagatgga caaggtgaag aactgctcct tcaacgtgac caccggcatc    480

cgcgacaaga agcagaaggt gaacgccctg ttctaccgcc tggacatcac ccccctggac    540

gagaacaaca acaactcctc cgagtaccgc ttgatcaact gcaagtcctc caccatcacc    600

caggcctgcc ccaaggtgaa cttcgacccc atccccatcc actactgcgc ccccgccggc    660

tacgccatcc tgaagtgcaa caacaagacc ttcaacggca ccggcccctg ccacaacgtg    720

tccaccgtgc agtgcaccca cggcatcaag cccgtggtgt ccacccagct gctgctgaac    780

ggctccctgg ccgagcgcga gatcatcatc cgctccgaga acctgaccga caacgtgaag    840

accatcatcg tgcacttcaa cgagtccgtg gagatcaact gcacccgccc caacaacaac    900

acccgcaagt ccatccgcat cggccccggc caggccttct acgccaccgg cgacatcatc    960

ggcgacatcc gccaggccca ctgcaacatc tccaaggaga actggaacaa gaccctgcag   1020

tgggtgcgcg gcaagctgga ggagcacttc cccaacaaga ccatcgtgtt caagccctcc   1080

tccggcggcg acctggagat caccacccac tccttcaact gccgcggcga gttcttctac   1140

tgcaacacct ccaagctgtt caacggcacc gacaactcca cccacatgga caccggcaac   1200

gacaccgtga tcaccatccc ctgccgcatc aagcagatca tcaacatgtg gcaggaggtg   1260

gggcgcgcca tgtacgcccc ccccatcgag ggcaacatca cctgcaagtc caacatcacc   1320

ggcctgctgc tggtgcgcga cggcggccag gacaactcca ccaacaacac cgagaccttc   1380

cgccccggcg gcggcgacat gcgcaacaac tggcgctccg agctgtacaa gtacaaggtg   1440

gtggagatca agcccctggg catcgccccc accaaggcca agcgccgcgt ggtggagcgc   1500

gagaagcgcg ccgtgggcat cggcgccgtg ttcctgggct tcctgggcgc cgccggctcc   1560

accatgggcg ccgcctccat caccctgacc gtgcaggccc gccagctgct gtccggcatc   1620

gtgcagcagc aggacaacct gctgcgcgcc atcgaggccc agcagcacat gctgcagctg   1680

accgtgtggg gcatcaaaca gctgcaggcc cgcgtgctgg ccatcgagcg ctacctgcag   1740
```

```
gaccagcagc tgctgggcat ctggggctgc tccggcaagc tgatctgcac caccgccgtg   1800

ccctggaacg cctcctggtc caacaagtcc cagaccgaca tctgggagaa catgacctgg   1860

atgcagtggg acaaggagat ctccaagcac accgacacca tctaccgcct gctggaggac   1920

tcccagaacc agcaggagaa gaacgagaag gacctgctgg ccctggactc ctgggagaac   1980

ctgtggaact ggttctccat caccaagtgg ctgtggtaca tcaagatctt catcatgatc   2040

gtgggcggcc tgatcggcct gcgcatcatc ttcgccgtgc tgtccatcgt gtcccgcgtg   2100

cgccagggct actccccccct gtccttccag acccacctgc ccaccccccg cggccccgac   2160

cgccccgagg gcatcgagga ggagggcggc gagcgcgacc gcgaccgctc catccgcctg   2220

gtgaacggct ccctggccct gatctgggac gacctgcgct ccctgtgcct gttctcctac   2280

caccgcctgc gcgacctgct gctgatcgtg acccgcatcg tggagctgct gggccgccgc   2340

ggctgggagg ccctgaagta ctggtggaac ctgctgcagt actggtccca ggagctgaag   2400

aactccgccg tgtccctgct gaacgccacc gccatcgccg tggccgaggg caccgaccgc   2460

gtgatcgagg tggtgcaggg cgcctgccgc gccatccgcc acatcccccg ccgcatgcgc   2520

cagggcctgg agcgcatcct gctgtga                                        2547


<210> SEQ ID NO 2
<211> LENGTH: 848
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Lys Thr Thr Leu Phe Cys Ala Ser Asp Ala Lys Ala Tyr Glu Lys Glu
    50                  55                  60

Val His Asn Ile Trp Ala Thr His Ala Cys Val Pro Thr Asp Pro Asn
65                  70                  75                  80

Pro Gln Glu Ile Val Leu Glu Asn Val Thr Glu Asn Phe Asn Met Trp
                85                  90                  95

Lys Asp Asp Met Val Asp Gln Met His Glu Asp Ile Ile Ser Leu Trp
            100                 105                 110

Asp Gln Ser Leu Lys Pro Cys Val Lys Leu Thr Pro Leu Cys Val Thr
        115                 120                 125

Leu Lys Cys Ser Asn Phe Thr Arg Glu Gly Asn Val Thr Tyr Lys Glu
    130                 135                 140

Glu Met Asp Lys Val Lys Asn Cys Ser Phe Asn Val Thr Thr Gly Ile
145                 150                 155                 160

Arg Asp Lys Lys Gln Lys Val Asn Ala Leu Phe Tyr Arg Leu Asp Ile
                165                 170                 175

Thr Pro Leu Asp Glu Asn Asn Asn Asn Ser Ser Glu Tyr Arg Leu Ile
            180                 185                 190

Asn Cys Lys Ser Ser Thr Ile Thr Gln Ala Cys Pro Lys Val Asn Phe
        195                 200                 205

Asp Pro Ile Pro Ile His Tyr Cys Ala Pro Ala Gly Tyr Ala Ile Leu
```

-continued

```
    210                 215                 220

Lys Cys Asn Asn Lys Thr Phe Asn Gly Thr Gly Pro Cys His Asn Val
225                 230                 235                 240

Ser Thr Val Gln Cys Thr His Gly Ile Lys Pro Val Val Ser Thr Gln
                245                 250                 255

Leu Leu Leu Asn Gly Ser Leu Ala Glu Arg Glu Ile Ile Ile Arg Ser
            260                 265                 270

Glu Asn Leu Thr Asp Asn Val Lys Thr Ile Ile Val His Phe Asn Glu
        275                 280                 285

Ser Val Glu Ile Asn Cys Thr Arg Pro Asn Asn Asn Thr Arg Lys Ser
    290                 295                 300

Ile Arg Ile Gly Pro Gly Gln Ala Phe Tyr Ala Thr Gly Asp Ile Ile
305                 310                 315                 320

Gly Asp Ile Arg Gln Ala His Cys Asn Ile Ser Lys Glu Asn Trp Asn
                325                 330                 335

Lys Thr Leu Gln Trp Val Arg Gly Lys Leu Glu Glu His Phe Pro Asn
            340                 345                 350

Lys Thr Ile Val Phe Lys Pro Ser Ser Gly Gly Asp Leu Glu Ile Thr
        355                 360                 365

Thr His Ser Phe Asn Cys Arg Gly Glu Phe Phe Tyr Cys Asn Thr Ser
    370                 375                 380

Lys Leu Phe Asn Gly Thr Asp Asn Ser Thr His Met Asp Thr Gly Asn
385                 390                 395                 400

Asp Thr Val Ile Thr Ile Pro Cys Arg Ile Lys Gln Ile Ile Asn Met
                405                 410                 415

Trp Gln Glu Val Gly Arg Ala Met Tyr Ala Pro Pro Ile Glu Gly Asn
            420                 425                 430

Ile Thr Cys Lys Ser Asn Ile Thr Gly Leu Leu Leu Val Arg Asp Gly
        435                 440                 445

Gly Gln Asp Asn Ser Thr Asn Asn Thr Glu Thr Phe Arg Pro Gly Gly
    450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Lys Ala Lys Arg Arg
                485                 490                 495

Val Val Glu Arg Glu Lys Arg Ala Val Gly Ile Gly Ala Val Phe Leu
            500                 505                 510

Gly Phe Leu Gly Ala Ala Gly Ser Thr Met Gly Ala Ala Ser Ile Thr
        515                 520                 525

Leu Thr Val Gln Ala Arg Gln Leu Leu Ser Gly Ile Val Gln Gln Gln
    530                 535                 540

Asp Asn Leu Leu Arg Ala Ile Glu Ala Gln Gln His Met Leu Gln Leu
545                 550                 555                 560

Thr Val Trp Gly Ile Lys Gln Leu Gln Ala Arg Val Leu Ala Ile Glu
                565                 570                 575

Arg Tyr Leu Gln Asp Gln Gln Leu Leu Gly Ile Trp Gly Cys Ser Gly
            580                 585                 590

Lys Leu Ile Cys Thr Thr Ala Val Pro Trp Asn Ala Ser Trp Ser Asn
        595                 600                 605

Lys Ser Gln Thr Asp Ile Trp Glu Asn Met Thr Trp Met Gln Trp Asp
    610                 615                 620

Lys Glu Ile Ser Lys His Thr Asp Thr Ile Tyr Arg Leu Leu Glu Asp
625                 630                 635                 640
```

-continued

```
Ser Gln Asn Gln Gln Glu Lys Asn Glu Lys Asp Leu Leu Ala Leu Asp
                645                 650                 655

Ser Trp Glu Asn Leu Trp Asn Trp Phe Ser Ile Thr Lys Trp Leu Trp
            660                 665                 670

Tyr Ile Lys Ile Phe Ile Met Ile Val Gly Gly Leu Ile Gly Leu Arg
        675                 680                 685

Ile Ile Phe Ala Val Leu Ser Ile Val Ser Arg Val Arg Gln Gly Tyr
    690                 695                 700

Ser Pro Leu Ser Phe Gln Thr His Leu Pro Thr Pro Arg Gly Pro Asp
705                 710                 715                 720

Arg Pro Glu Gly Ile Glu Glu Glu Gly Gly Glu Arg Asp Arg Asp Arg
                725                 730                 735

Ser Ile Arg Leu Val Asn Gly Ser Leu Ala Leu Ile Trp Asp Asp Leu
            740                 745                 750

Arg Ser Leu Cys Leu Phe Ser Tyr His Arg Leu Arg Asp Leu Leu Leu
        755                 760                 765

Ile Val Thr Arg Ile Val Glu Leu Leu Gly Arg Arg Gly Trp Glu Ala
    770                 775                 780

Leu Lys Tyr Trp Trp Asn Leu Leu Gln Tyr Trp Ser Gln Glu Leu Lys
785                 790                 795                 800

Asn Ser Ala Val Ser Leu Leu Asn Ala Thr Ala Ile Ala Val Ala Glu
                805                 810                 815

Gly Thr Asp Arg Val Ile Glu Val Val Gln Gly Ala Cys Arg Ala Ile
            820                 825                 830

Arg His Ile Pro Arg Arg Met Arg Gln Gly Leu Glu Arg Ile Leu Leu
        835                 840                 845
```

<210> SEQ ID NO 3
<211> LENGTH: 2313
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
atgcgcgtga aggagaagta ccagcacctg tggcgctggg gctggcgctg gggcaccatg     60

ctgctgggca tgctgatgat ctgctccgcc accgagaagc tgtgggtgac cgtgtactac    120

ggcgtgcccg tgtggaagga ggccaagacc accctgttct gcgcctccga cgccaaggcc    180

tacgagaagg aggtgcacaa catctgggcc acccacgcct gcgtgcccac cgaccccaac    240

ccccaggaga tcgtgctgga gaacgtgacc gagaacttca acatgtggaa ggacgacatg    300

gtggaccaga tgcacgagga catcatctcc ctgtgggacc agtccctgaa gccctgcgtg    360

ggcgccggcg cctgccccaa ggtgaacttc gaccccatcc ccatccacta ctgcgccccc    420

gccggctacg ccatcctgaa gtgcaacaac aagaccttca acggcaccgg cccctgccac    480

aacgtgtcca ccgtgcagtg cacccacggc atcaagcccg tggtgtccac ccagctgctg    540

ctgaacggct ccctggccga gcgcgagatc atcatccgct ccgagaacct gaccgacaac    600

gtgaagacca tcatcgtgca cttcaacgag tccgtggaga tcaactgcac ccgccccaac    660

aacaacaccc gcaagtccat ccgcatcggc cccggccagg ccttctacgc caccggcgac    720

atcatcggcg acatccgcca ggcccactgc aacatctcca aggagaactg gaacaagacc    780

ctgcagtggg tgcgcggcaa gctggaggag cacttcccca acaagaccat cgtgttcaag    840

ccctcctccg gcggcgacct ggagatcacc acccactcct tcaactgccg cggcgagttc    900
```

-continued

```
ttctactgca acacctccaa gctgttcaac ggcaccgaca actccaccca catggacacc    960

ggcaacgaca ccgtgatcac catcccctgc cgcatcaagc agatcatcaa catgtggcag   1020

gaggtggggc gcgccatgta cgcccccccc atcgagggca acatcacctg caagtccaac   1080

atcaccggcc tgctgctggt gcgcgacggc ggccaggaca actccaccaa caacaccgag   1140

accttccgcc ccggcggcgg cgacatgcgc aacaactggc gctccgagct gtacaagtac   1200

aaggtggtgg agatcaagcc cctgggcatc gcccccacca aggccaagcg ccgcgtggtg   1260

gagcgcgaga agcgcgccgt gggcatcggc gccgtgttcc tgggcttcct gggcgccgcc   1320

ggctccacca tgggcgccgc ctccatcacc ctgaccgtgc aggcccgcca gctgctgtcc   1380

ggcatcgtgc agcagcagga caacctgctg cgcgccatcg aggcccagca gcacatgctg   1440

cagctgaccg tgtggggcat caaacagctg caggcccgcg tgctggccat cgagcgctac   1500

ctgcaggacc agcagctgct gggcatctgg ggctgctccg gcaagctgat ctgcaccacc   1560

gccgtgccct ggaacgcctc ctggtccaac aagtcccaga ccgacatctg ggagaacatg   1620

acctggatgc agtgggacaa ggagatctcc aagcacaccg acaccatcta ccgcctgctg   1680

gaggactccc agaaccagca ggagaagaac gagaaggacc tgctggccct ggactcctgg   1740

gagaacctgt ggaactggtt ctccatcacc aagtggctgt ggtacatcaa gatcttcatc   1800

atgatcgtgg gcggcctgat cggcctgcgc atcatcttcg ccgtgctgtc catcgtgtcc   1860

cgcgtgcgcc agggctactc ccccctgtcc ttccagaccc acctgcccac cccccgcggc   1920

cccgaccgcc ccgagggcat cgaggaggag ggcggcgagc gcgaccgcga ccgctccatc   1980

cgcctggtga acggctccct ggccctgatc tgggacgacc tgcgctccct gtgcctgttc   2040

tcctaccacc gcctgcgcga cctgctgctg atcgtgaccc gcatcgtgga gctgctgggc   2100

cgccgcggct gggaggccct gaagtactgg tggaacctgc tgcagtactg gtcccaggag   2160

ctgaagaact ccgccgtgtc cctgctgaac gccaccgcca tcgccgtggc cgagggcacc   2220

gaccgcgtga tcgaggtggt gcagggcgcc tgccgcgcca tccgccacat cccccgccgc   2280

atgcgccagg gcctggagcg catcctgctg tga                                2313
```

<210> SEQ ID NO 4
<211> LENGTH: 770
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Lys Thr Thr Leu Phe Cys Ala Ser Asp Ala Lys Ala Tyr Glu Lys Glu
    50                  55                  60

Val His Asn Ile Trp Ala Thr His Ala Cys Val Pro Thr Asp Pro Asn
65                  70                  75                  80

Pro Gln Glu Ile Val Leu Glu Asn Val Thr Glu Asn Phe Asn Met Trp
                85                  90                  95

Lys Asp Asp Met Val Asp Gln Met His Glu Asp Ile Ile Ser Leu Trp
            100                 105                 110
```

```
Asp Gln Ser Leu Lys Pro Cys Val Gly Ala Gly Ala Cys Pro Lys Val
        115                 120                 125

Asn Phe Asp Pro Ile Pro Ile His Tyr Cys Ala Pro Ala Gly Tyr Ala
    130                 135                 140

Ile Leu Lys Cys Asn Asn Lys Thr Phe Asn Gly Thr Gly Pro Cys His
145                 150                 155                 160

Asn Val Ser Thr Val Gln Cys Thr His Gly Ile Lys Pro Val Val Ser
                165                 170                 175

Thr Gln Leu Leu Leu Asn Gly Ser Leu Ala Glu Arg Glu Ile Ile Ile
            180                 185                 190

Arg Ser Glu Asn Leu Thr Asp Asn Val Lys Thr Ile Ile Val His Phe
        195                 200                 205

Asn Glu Ser Val Glu Ile Asn Cys Thr Arg Pro Asn Asn Asn Thr Arg
    210                 215                 220

Lys Ser Ile Arg Ile Gly Pro Gly Gln Ala Phe Tyr Ala Thr Gly Asp
225                 230                 235                 240

Ile Ile Gly Asp Ile Arg Gln Ala His Cys Asn Ile Ser Lys Glu Asn
                245                 250                 255

Trp Asn Lys Thr Leu Gln Trp Val Arg Gly Lys Leu Glu Glu His Phe
            260                 265                 270

Pro Asn Lys Thr Ile Val Phe Lys Pro Ser Ser Gly Gly Asp Leu Glu
        275                 280                 285

Ile Thr Thr His Ser Phe Asn Cys Arg Gly Glu Phe Phe Tyr Cys Asn
    290                 295                 300

Thr Ser Lys Leu Phe Asn Gly Thr Asp Asn Ser Thr His Met Asp Thr
305                 310                 315                 320

Gly Asn Asp Thr Val Ile Thr Ile Pro Cys Arg Ile Lys Gln Ile Ile
                325                 330                 335

Asn Met Trp Gln Glu Val Gly Arg Ala Met Tyr Ala Pro Pro Ile Glu
            340                 345                 350

Gly Asn Ile Thr Cys Lys Ser Asn Ile Thr Gly Leu Leu Leu Val Arg
        355                 360                 365

Asp Gly Gly Gln Asp Asn Ser Thr Asn Asn Thr Glu Thr Phe Arg Pro
    370                 375                 380

Gly Gly Gly Asp Met Arg Asn Asn Trp Arg Ser Glu Leu Tyr Lys Tyr
385                 390                 395                 400

Lys Val Val Glu Ile Lys Pro Leu Gly Ile Ala Pro Thr Lys Ala Lys
                405                 410                 415

Arg Arg Val Val Glu Arg Glu Lys Arg Ala Val Gly Ile Gly Ala Val
            420                 425                 430

Phe Leu Gly Phe Leu Gly Ala Ala Gly Ser Thr Met Gly Ala Ala Ser
        435                 440                 445

Ile Thr Leu Thr Val Gln Ala Arg Gln Leu Leu Ser Gly Ile Val Gln
    450                 455                 460

Gln Gln Asp Asn Leu Leu Arg Ala Ile Glu Ala Gln Gln His Met Leu
465                 470                 475                 480

Gln Leu Thr Val Trp Gly Ile Lys Gln Leu Gln Ala Arg Val Leu Ala
                485                 490                 495

Ile Glu Arg Tyr Leu Gln Asp Gln Gln Leu Leu Gly Ile Trp Gly Cys
            500                 505                 510

Ser Gly Lys Leu Ile Cys Thr Thr Ala Val Pro Trp Asn Ala Ser Trp
        515                 520                 525

Ser Asn Lys Ser Gln Thr Asp Ile Trp Glu Asn Met Thr Trp Met Gln
    530                 535                 540
```

Trp Asp Lys Glu Ile Ser Lys His Thr Asp Thr Ile Tyr Arg Leu Leu
545 550 555 560

Glu Asp Ser Gln Asn Gln Gln Glu Lys Asn Glu Lys Asp Leu Leu Ala
565 570 575

Leu Asp Ser Trp Glu Asn Leu Trp Asn Trp Phe Ser Ile Thr Lys Trp
580 585 590

Leu Trp Tyr Ile Lys Ile Phe Ile Met Ile Val Gly Gly Leu Ile Gly
595 600 605

Leu Arg Ile Ile Phe Ala Val Leu Ser Ile Val Ser Arg Val Arg Gln
610 615 620

Gly Tyr Ser Pro Leu Ser Phe Gln Thr His Leu Pro Thr Pro Arg Gly
625 630 635 640

Pro Asp Arg Pro Glu Gly Ile Glu Glu Glu Gly Gly Glu Arg Asp Arg
645 650 655

Asp Arg Ser Ile Arg Leu Val Asn Gly Ser Leu Ala Leu Ile Trp Asp
660 665 670

Asp Leu Arg Ser Leu Cys Leu Phe Ser Tyr His Arg Leu Arg Asp Leu
675 680 685

Leu Leu Ile Val Thr Arg Ile Val Glu Leu Leu Gly Arg Arg Gly Trp
690 695 700

Glu Ala Leu Lys Tyr Trp Trp Asn Leu Leu Gln Tyr Trp Ser Gln Glu
705 710 715 720

Leu Lys Asn Ser Ala Val Ser Leu Leu Asn Ala Thr Ala Ile Ala Val
725 730 735

Ala Glu Gly Thr Asp Arg Val Ile Glu Val Val Gln Gly Ala Cys Arg
740 745 750

Ala Ile Arg His Ile Pro Arg Arg Met Arg Gln Gly Leu Glu Arg Ile
755 760 765

Leu Leu
770

<210> SEQ ID NO 5
<211> LENGTH: 2232
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 5
atgcgcgtga aggagaagta ccagcacctg tggcgctggg gctggcgctg gggcaccatg 60
ctgctgggca tgctgatgat ctgctccgcc accgagaagc tgtgggtgac cgtgtactac 120
ggcgtgcccg tgtggaagga ggccaagacc accctgttct gcgcctccga cgccaaggcc 180
tacgagaagg aggtgcacaa catctgggcc acccacgcct gcgtgcccac cgaccccaac 240
ccccaggaga tcgtgctgga gaacgtgacc gagaacttca acatgtggaa ggacgacatg 300
gtggaccaga tgcacgagga catcatctcc ctgtgggacc agtccctgaa gccctgcgtg 360
ggcgccggcg cctgccccaa ggtgaacttc gaccccatcc ccatccacta ctgcgccccc 420
gccggctacg ccatcctgaa gtgcaacaac aagaccttca acggcaccgg cccctgccac 480
aacgtgtcca ccgtgcagtg cacccacggc atcaagcccg tggtgtccac ccagctgctg 540
ctgaacggct ccctggccga gcgcgagatc atcatccgct ccgagaacct gaccgacaac 600
gtgaagacca tcatcgtgca cttcaacgag tccgtggaga tcaactgcac cggcgccggc 660
gcccactgca acatctccaa ggagaactgg aacaagaccc tgcagtgggt gcgcggcaag 720

```
ctggaggagc acttccccaa caagaccatc gtgttcaagc cctcctccgg cggcgacctg    780

gagatcacca cccactcctt caactgccgc ggcgagttct tctactgcaa cacctccaag    840

ctgttcaacg gcaccgacaa ctccacccac atggacaccg gcaacgacac cgtgatcacc    900

atcccctgcc gcatcaagca gatcatcaac atgtggcagg aggtggggcg cgccatgtac    960

gcccccccca tcgagggcaa catcacctgc aagtccaaca tcaccggcct gctgctggtg   1020

cgcgacggcg gccaggacaa ctccaccaac aacaccgaga ccttccgccc cggcggcggc   1080

gacatgcgca acaactggcg ctccgagctg tacaagtaca aggtggtgga gatcaagccc   1140

ctgggcatcg cccccaccaa ggccaagcgc cgcgtggtgg agcgcgagaa gcgcgccgtg   1200

ggcatcggcg ccgtgttcct gggcttcctg ggcgccgccg gctccaccat gggcgccgcc   1260

tccatcaccc tgaccgtgca ggcccgccag ctgctgtccg gcatcgtgca gcagcaggac   1320

aacctgctgc gcgccatcga ggcccagcag cacatgctgc agctgaccgt gtggggcatc   1380

aaacagctgc aggcccgcgt gctggccatc gagcgctacc tgcaggacca gcagctgctg   1440

ggcatctggg gctgctccgg caagctgatc tgcaccaccg ccgtgccctg gaacgcctcc   1500

tggtccaaca agtcccagac cgacatctgg gagaacatga cctggatgca gtgggacaag   1560

gagatctcca agcacaccga caccatctac cgcctgctgg aggactccca gaaccagcag   1620

gagaagaacg agaaggacct gctggccctg gactcctggg agaacctgtg gaactggttc   1680

tccatcacca agtggctgtg gtacatcaag atcttcatca tgatcgtggg cggcctgatc   1740

ggcctgcgca tcatcttcgc cgtgctgtcc atcgtgtccc gcgtgcgcca gggctactcc   1800

cccctgtcct tccagaccca cctgcccacc ccccgcggcc ccgaccgccc cgagggcatc   1860

gaggaggagg gcggcgagcg cgaccgcgac cgctccatcc gcctggtgaa cggctccctg   1920

gccctgatct gggacgacct gcgctccctg tgcctgttct cctaccaccg cctgcgcgac   1980

ctgctgctga tcgtgacccg catcgtggag ctgctgggcc gccgcggctg ggaggccctg   2040

aagtactggt ggaacctgct gcagtactgg tcccaggagc tgaagaactc cgccgtgtcc   2100

ctgctgaacg ccaccgccat cgccgtggcc gagggcaccg accgcgtgat cgaggtggtg   2160

cagggcgcct gccgcgccat ccgccacatc ccccgccgca tgcgccaggg cctggagcgc   2220

atcctgctgt ga                                                       2232
```

```
<210> SEQ ID NO 6
<211> LENGTH: 743
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Lys Thr Thr Leu Phe Cys Ala Ser Asp Ala Lys Ala Tyr Glu Lys Glu
    50                  55                  60

Val His Asn Ile Trp Ala Thr His Ala Cys Val Pro Thr Asp Pro Asn
65                  70                  75                  80

Pro Gln Glu Ile Val Leu Glu Asn Val Thr Glu Asn Phe Asn Met Trp
```

-continued

```
                85                  90                  95

Lys Asp Asp Met Val Asp Gln Met His Glu Asp Ile Ile Ser Leu Trp
            100                 105                 110

Asp Gln Ser Leu Lys Pro Cys Val Gly Ala Gly Ala Cys Pro Lys Val
        115                 120                 125

Asn Phe Asp Pro Ile Pro Ile His Tyr Cys Ala Pro Ala Gly Tyr Ala
    130                 135                 140

Ile Leu Lys Cys Asn Asn Lys Thr Phe Asn Gly Thr Gly Pro Cys His
145                 150                 155                 160

Asn Val Ser Thr Val Gln Cys Thr His Gly Ile Lys Pro Val Val Ser
                165                 170                 175

Thr Gln Leu Leu Leu Asn Gly Ser Leu Ala Glu Arg Glu Ile Ile Ile
            180                 185                 190

Arg Ser Glu Asn Leu Thr Asp Asn Val Lys Thr Ile Ile Val His Phe
        195                 200                 205

Asn Glu Ser Val Glu Ile Asn Cys Thr Gly Ala Gly Ala His Cys Asn
    210                 215                 220

Ile Ser Lys Glu Asn Trp Asn Lys Thr Leu Gln Trp Val Arg Gly Lys
225                 230                 235                 240

Leu Glu Glu His Phe Pro Asn Lys Thr Ile Val Phe Lys Pro Ser Ser
                245                 250                 255

Gly Gly Asp Leu Glu Ile Thr Thr His Ser Phe Asn Cys Arg Gly Glu
            260                 265                 270

Phe Phe Tyr Cys Asn Thr Ser Lys Leu Phe Asn Gly Thr Asp Asn Ser
        275                 280                 285

Thr His Met Asp Thr Gly Asn Asp Thr Val Ile Thr Ile Pro Cys Arg
    290                 295                 300

Ile Lys Gln Ile Ile Asn Met Trp Gln Glu Val Gly Arg Ala Met Tyr
305                 310                 315                 320

Ala Pro Pro Ile Glu Gly Asn Ile Thr Cys Lys Ser Asn Ile Thr Gly
                325                 330                 335

Leu Leu Leu Val Arg Asp Gly Gly Gln Asp Asn Ser Thr Asn Asn Thr
            340                 345                 350

Glu Thr Phe Arg Pro Gly Gly Gly Asp Met Arg Asn Asn Trp Arg Ser
        355                 360                 365

Glu Leu Tyr Lys Tyr Lys Val Val Glu Ile Lys Pro Leu Gly Ile Ala
    370                 375                 380

Pro Thr Lys Ala Lys Arg Arg Val Val Glu Arg Glu Lys Arg Ala Val
385                 390                 395                 400

Gly Ile Gly Ala Val Phe Leu Gly Phe Leu Gly Ala Ala Gly Ser Thr
                405                 410                 415

Met Gly Ala Ala Ser Ile Thr Leu Thr Val Gln Ala Arg Gln Leu Leu
            420                 425                 430

Ser Gly Ile Val Gln Gln Gln Asp Asn Leu Leu Arg Ala Ile Glu Ala
        435                 440                 445

Gln Gln His Met Leu Gln Leu Thr Val Trp Gly Ile Lys Gln Leu Gln
    450                 455                 460

Ala Arg Val Leu Ala Ile Glu Arg Tyr Leu Gln Asp Gln Gln Leu Leu
465                 470                 475                 480

Gly Ile Trp Gly Cys Ser Gly Lys Leu Ile Cys Thr Thr Ala Val Pro
                485                 490                 495

Trp Asn Ala Ser Trp Ser Asn Lys Ser Gln Thr Asp Ile Trp Glu Asn
            500                 505                 510
```

-continued

```
Met Thr Trp Met Gln Trp Asp Lys Glu Ile Ser Lys His Thr Asp Thr
        515                 520                 525

Ile Tyr Arg Leu Leu Glu Asp Ser Gln Asn Gln Gln Glu Lys Asn Glu
    530                 535                 540

Lys Asp Leu Leu Ala Leu Asp Ser Trp Glu Asn Leu Trp Asn Trp Phe
545                 550                 555                 560

Ser Ile Thr Lys Trp Leu Trp Tyr Ile Lys Ile Phe Ile Met Ile Val
                565                 570                 575

Gly Gly Leu Ile Gly Leu Arg Ile Ile Phe Ala Val Leu Ser Ile Val
            580                 585                 590

Ser Arg Val Arg Gln Gly Tyr Ser Pro Leu Ser Phe Gln Thr His Leu
        595                 600                 605

Pro Thr Pro Arg Gly Pro Asp Arg Pro Glu Gly Ile Glu Glu Glu Gly
    610                 615                 620

Gly Glu Arg Asp Arg Asp Arg Ser Ile Arg Leu Val Asn Gly Ser Leu
625                 630                 635                 640

Ala Leu Ile Trp Asp Asp Leu Arg Ser Leu Cys Leu Phe Ser Tyr His
                645                 650                 655

Arg Leu Arg Asp Leu Leu Leu Ile Val Thr Arg Ile Val Glu Leu Leu
            660                 665                 670

Gly Arg Arg Gly Trp Glu Ala Leu Lys Tyr Trp Trp Asn Leu Leu Gln
        675                 680                 685

Tyr Trp Ser Gln Glu Leu Lys Asn Ser Ala Val Ser Leu Leu Asn Ala
    690                 695                 700

Thr Ala Ile Ala Val Ala Glu Gly Thr Asp Arg Val Ile Glu Val Val
705                 710                 715                 720

Gln Gly Ala Cys Arg Ala Ile Arg His Ile Pro Arg Arg Met Arg Gln
                725                 730                 735

Gly Leu Glu Arg Ile Leu Leu
            740


<210> SEQ ID NO 7
<211> LENGTH: 2169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

atgcgcgtga aggagaagta ccagcacctg tggcgctggg gctggcgctg gggcaccatg     60

ctgctgggca tgctgatgat ctgctccgcc accgagaagc tgtgggtgac cgtgtactac    120

ggcgtgcccg tgtggaagga ggccaagacc accctgttct gcgcctccga cgccaaggcc    180

tacgagaagg aggtgcacaa catctgggcc acccacgcct gcgtgcccac cgacccccaac    240

ccccaggaga tcgtgctgga gaacgtgacc gagaacttca acatgtggaa ggacgacatg    300

gtggaccaga tgcacgagga catcatctcc ctgtgggacc agtccctgaa gccctgcgtg    360

ggcgccggcg cctgccccaa ggtgaacttc gaccccatcc ccatccacta ctgcgccccc    420

gccggctacg ccatcctgaa gtgcaacaac aagaccttca acggcaccgg cccctgccac    480

aacgtgtcca ccgtgcagtg cacccacggc atcaagcccg tggtgtccac ccagctgctg    540

ctgaacggct ccctggccga gcgcgagatc atcatccgct ccgagaacct gaccgacaac    600

gtgaagacca tcatcgtgca cttcaacgag tccgtggaga tcaactgcac cggcgccggc    660

gcccactgca acatctccaa ggagaactgg aacaagaccc tgcagtgggt gcgcggcaag    720
```

```
ctggaggagc acttccccaa caagaccatc gtgttcaagc cctcctccgg cggcgacctg    780

gagatcacca cccactcctt caactgccgc ggcgagttct tctactgcaa cggcgccggc    840

ccctgccgca tcaagcagat catcaacatg tggcaggagg tggggcgcgc catgtacgcc    900

ccccccatcg agggcaacat cacctgcaag tccaacatca ccggcctgct gctggtgcgc    960

gacggcggcc aggacaactc caccaacaac accgagacct tccgccccgg cggcggcgac   1020

atgcgcaaca actggcgctc cgagctgtac aagtacaagg tggtggagat caagcccctg   1080

ggcatcgccc ccaccaaggc caagcgccgc gtggtggagc gcgagaagcg cgccgtgggc   1140

atcggcgccg tgttcctggg cttcctgggc gccgccggct ccaccatggg cgccgcctcc   1200

atcaccctga ccgtgcaggc ccgccagctg ctgtccggca tcgtgcagca gcaggacaac   1260

ctgctgcgcg ccatcgaggc ccagcagcac atgctgcagc tgaccgtgtg gggcatcaaa   1320

cagctgcagg cccgcgtgct ggccatcgag cgctacctgc aggaccagca gctgctgggc   1380

atctggggct gctccggcaa gctgatctgc accaccgccg tgccctggaa cgcctcctgg   1440

tccaacaagt cccagaccga catctgggag aacatgacct ggatgcagtg ggacaaggag   1500

atctccaagc acaccgacac catctaccgc ctgctggagg actcccagaa ccagcaggag   1560

aagaacgaga aggacctgct ggccctggac tcctgggaga acctgtggaa ctggttctcc   1620

atcaccaagt ggctgtggta catcaagatc ttcatcatga tcgtgggcgg cctgatcggc   1680

ctgcgcatca tcttcgccgt gctgtccatc gtgtcccgcg tgcgccaggg ctactccccc   1740

ctgtccttcc agacccacct gcccaccccc cgcggccccg accgccccga gggcatcgag   1800

gaggagggcg gcgagcgcga ccgcgaccgc tccatccgcc tggtgaacgg ctccctggcc   1860

ctgatctggg acgacctgcg ctccctgtgc ctgttctcct accaccgcct gcgcgacctg   1920

ctgctgatcg tgacccgcat cgtggagctg ctgggccgcc gcggctggga ggccctgaag   1980

tactggtgga acctgctgca gtactggtcc caggagctga agaactccgc cgtgtccctg   2040

ctgaacgcca ccgccatcgc cgtggccgag ggcaccgacc gcgtgatcga ggtggtgcag   2100

ggcgcctgcc gcgccatccg ccacatcccc cgccgcatgc gccagggcct ggagcgcatc   2160

ctgctgtga                                                          2169
```

```
<210> SEQ ID NO 8
<211> LENGTH: 722
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Lys Thr Thr Leu Phe Cys Ala Ser Asp Ala Lys Ala Tyr Glu Lys Glu
    50                  55                  60

Val His Asn Ile Trp Ala Thr His Ala Cys Val Pro Thr Asp Pro Asn
65                  70                  75                  80

Pro Gln Glu Ile Val Leu Glu Asn Val Thr Glu Asn Phe Asn Met Trp
                85                  90                  95

Lys Asp Asp Met Val Asp Gln Met His Glu Asp Ile Ile Ser Leu Trp
```

-continued

```
            100                 105                 110

Asp Gln Ser Leu Lys Pro Cys Val Gly Ala Gly Ala Cys Pro Lys Val
        115                 120                 125

Asn Phe Asp Pro Ile Pro Ile His Tyr Cys Ala Pro Ala Gly Tyr Ala
    130                 135                 140

Ile Leu Lys Cys Asn Asn Lys Thr Phe Asn Gly Thr Gly Pro Cys His
145                 150                 155                 160

Asn Val Ser Thr Val Gln Cys Thr His Gly Ile Lys Pro Val Val Ser
                165                 170                 175

Thr Gln Leu Leu Leu Asn Gly Ser Leu Ala Glu Arg Glu Ile Ile Ile
            180                 185                 190

Arg Ser Glu Asn Leu Thr Asp Asn Val Lys Thr Ile Ile Val His Phe
        195                 200                 205

Asn Glu Ser Val Glu Ile Asn Cys Thr Gly Ala Gly Ala His Cys Asn
    210                 215                 220

Ile Ser Lys Glu Asn Trp Asn Lys Thr Leu Gln Trp Val Arg Gly Lys
225                 230                 235                 240

Leu Glu Glu His Phe Pro Asn Lys Thr Ile Val Phe Lys Pro Ser Ser
                245                 250                 255

Gly Gly Asp Leu Glu Ile Thr Thr His Ser Phe Asn Cys Arg Gly Glu
            260                 265                 270

Phe Phe Tyr Cys Asn Gly Ala Gly Pro Cys Arg Ile Lys Gln Ile Ile
        275                 280                 285

Asn Met Trp Gln Glu Val Gly Arg Ala Met Tyr Ala Pro Pro Ile Glu
    290                 295                 300

Gly Asn Ile Thr Cys Lys Ser Asn Ile Thr Gly Leu Leu Leu Val Arg
305                 310                 315                 320

Asp Gly Gly Gln Asp Asn Ser Thr Asn Asn Thr Glu Thr Phe Arg Pro
                325                 330                 335

Gly Gly Gly Asp Met Arg Asn Asn Trp Arg Ser Glu Leu Tyr Lys Tyr
            340                 345                 350

Lys Val Val Glu Ile Lys Pro Leu Gly Ile Ala Pro Thr Lys Ala Lys
        355                 360                 365

Arg Arg Val Val Glu Arg Glu Lys Arg Ala Val Gly Ile Gly Ala Val
    370                 375                 380

Phe Leu Gly Phe Leu Gly Ala Ala Gly Ser Thr Met Gly Ala Ala Ser
385                 390                 395                 400

Ile Thr Leu Thr Val Gln Ala Arg Gln Leu Leu Ser Gly Ile Val Gln
                405                 410                 415

Gln Gln Asp Asn Leu Leu Arg Ala Ile Glu Ala Gln Gln His Met Leu
            420                 425                 430

Gln Leu Thr Val Trp Gly Ile Lys Gln Leu Gln Ala Arg Val Leu Ala
        435                 440                 445

Ile Glu Arg Tyr Leu Gln Asp Gln Gln Leu Leu Gly Ile Trp Gly Cys
    450                 455                 460

Ser Gly Lys Leu Ile Cys Thr Thr Ala Val Pro Trp Asn Ala Ser Trp
465                 470                 475                 480

Ser Asn Lys Ser Gln Thr Asp Ile Trp Glu Asn Met Thr Trp Met Gln
                485                 490                 495

Trp Asp Lys Glu Ile Ser Lys His Thr Asp Thr Ile Tyr Arg Leu Leu
            500                 505                 510

Glu Asp Ser Gln Asn Gln Gln Glu Lys Asn Glu Lys Asp Leu Leu Ala
        515                 520                 525
```

-continued

```
Leu Asp Ser Trp Glu Asn Leu Trp Asn Trp Phe Ser Ile Thr Lys Trp
    530                 535                 540

Leu Trp Tyr Ile Lys Ile Phe Ile Met Ile Val Gly Gly Leu Ile Gly
545                 550                 555                 560

Leu Arg Ile Ile Phe Ala Val Leu Ser Ile Val Ser Arg Val Arg Gln
                565                 570                 575

Gly Tyr Ser Pro Leu Ser Phe Gln Thr His Leu Pro Thr Pro Arg Gly
            580                 585                 590

Pro Asp Arg Pro Glu Gly Ile Glu Glu Glu Gly Gly Glu Arg Asp Arg
        595                 600                 605

Asp Arg Ser Ile Arg Leu Val Asn Gly Ser Leu Ala Leu Ile Trp Asp
    610                 615                 620

Asp Leu Arg Ser Leu Cys Leu Phe Ser Tyr His Arg Leu Arg Asp Leu
625                 630                 635                 640

Leu Leu Ile Val Thr Arg Ile Val Glu Leu Leu Gly Arg Arg Gly Trp
                645                 650                 655

Glu Ala Leu Lys Tyr Trp Trp Asn Leu Leu Gln Tyr Trp Ser Gln Glu
            660                 665                 670

Leu Lys Asn Ser Ala Val Ser Leu Leu Asn Ala Thr Ala Ile Ala Val
        675                 680                 685

Ala Glu Gly Thr Asp Arg Val Ile Glu Val Val Gln Gly Ala Cys Arg
    690                 695                 700

Ala Ile Arg His Ile Pro Arg Arg Met Arg Gln Gly Leu Glu Arg Ile
705                 710                 715                 720

Leu Leu


<210> SEQ ID NO 9
<211> LENGTH: 3925
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

gcatgctgta gagcaagaaa tggagccagt agatcctaga ctagagccct ggaagcatcc      60

aggaagcagg cctaaaactg cttgtaccaa ttgctattgt aaaaagtgtt gctttcattg     120

ccaagtttgt ttcataacaa aagccctagg catctcctat ggcaggaaga agcggagaca     180

gcgacgaaga gctcatcaga acagtcagac tcatcaagct tctctatcaa agcagtaagt     240

agtacatgta atgcaatcta tacaaataga aatagtagca ttagtagtag caataataat     300

agcaatagtt gtgtggtcca tagtaatcat agaatatagg aaaatattaa gacaaagaaa     360

aatagacagg ttaattaata gactaataga aagagcagaa gacagtggca atgagagtga     420

aggagaaata tcagcacttg tggagatggg ggtggagatg gggcatcatg ctccttggga     480

tgttgatgat ctgtagtgct acagaaaaat tgtgggtcac agtctattat ggggtacctg     540

tatggaaaga agcaaaaact actttattct gtgcatcaaa tgctaaagca tatgagaaag     600

aagtacataa catctgggct acacatgcct gtgtacccac agaccccaac ccacaagaaa     660

tagttttggg aaatgtaaca gaaaatttta acatgtggaa aaatgacatg gtggatcaga     720

tgcatgagga tataatcagt ttatgggatc aaagcctaaa gccatgtgta aagttgactt     780

cactctgtgt cactttaaag tgtagtaatt ttaccgggaa gagtaatgtt acctacaaag     840

gggatatgga agtaaaaaat tgctctttca atgtaaccac agaaataaga gataagaagc     900

agaaagtgta tgctcttttt tatagacttg atataacacc acttgatgac aactctagtg     960
```

-continued

```
agtatatatt aataaattgc aattcctcaa ccataacaca agcctgtcca aaggtcaatt   1020
ttgacccaat tcctatacat tattgtgctc cagctggtta tgcgattcta aagtgtaata   1080
ataagacatt taatgggaca ggaccatgcc ataatgtcag tacagtacaa tgtacacatg   1140
gaattaagcc agtggtatca actcaactac tgttaaacgg tagcctagca gaaggggaga   1200
taataattag atctgaaaat ctgacagaca atgtcaaaac aataatagta cactttaatg   1260
aatctgtaga aattacttgt acaagaccca acaataatac aagaaaaagt ataagcatag   1320
gaccaggaca agcaatctat gccacaggtg atataatagg agacataaga caagcacact   1380
gtaacattag taaagaaaat tggaacaaaa ctttacaatg ggtaaggga aaattaaaag    1440
aacacttccc taataaaaca atagtattta aaccatcctc aggaggggat ctagaaatta   1500
caacacatag ctttaattgt agaggagaat ttttctattg caacacatca aaactgttta   1560
atagtacaga caatagtaca cacatgggta cagaaaataa tacaatcatc acaatcccat   1620
gtagaataaa acaaattata aacatgtggc aggaggtagg acgagcaatg tatgcccccc   1680
ccatagaagg aaacataaca tgtaaatcaa atatcacagg actactactg gtacgtgatg   1740
gaggatggga caacagtaca aatgacacag aaacattcag gcctggagga ggagatatga   1800
gggacaattg gagaagtgaa ttatataaat ataaggtggt agaagtcaag ccattgggaa   1860
tagcacccac taaggcaaaa aggagagtgg tggagagaga aaaaagagca gtgggaatag   1920
gagctgtgtt ccttgggttc ttgggagcag caggaagcac tatgggcgcg gcgtcaataa   1980
cgctgacggt acaggccaga caactgttgt ctggtatagt gcagcagcaa gacaatttgc   2040
tgagagctat agaggcgcaa caacatatgt tgcaactcac agtctggggc attaagcagc   2100
tccaggcgag agtcctggct atagaaagat acctacagga tcaacagctc ctagggattt   2160
ggggctgctc tggaaaactc atctgcacca ctgctgtgcc ttggaacgac agttggagta   2220
ataaatctca aacagatatt tgggagaaca tgacctggat gcagtgggat agagaaatta   2280
gtagacacac agacacaata tacaggttgc ttgaagactc acaaaaccag caggagaaaa   2340
atgaaaaaga tttattagca ttggacagtt ggaaaaattt gtggaattgg tttagcataa   2400
caaggtggct gtggtatata aaaatattca taatgatagt aggaggcctg ataggtttga   2460
gaataatttt tgctgtgctc tcgatagtga atagagttag gcagggatac tcaccattat   2520
cgtttcagac ccacctccca cttccgaggg gagccgacag gcccgaagga atagaagaag   2580
aaggtggaga gagagacaga gacagatcca ttcgattagt gaccggatcc ttagcactta   2640
tctgggacga tctgcggagc ctgtgcctct tcagctacca ccgcttgaga gacttactct   2700
tgattgtaac gaggactgtg gaactcctgg gacgcagagg gtgggaagcc ctcaaatatt   2760
ggtggaatct cctactgtat tggagtcagg aactaaagaa tagtgctgtt agcttgctca   2820
acgccacagc catagcagta agacaatatg ggtggagcta tttccatgag gcggtccagg   2880
ccgtctggag atctgcgaca gagactcttg cgggcgcgtg ggagacttta tgggagattc   2940
ttaggagagg tggaagatgg atactcgcaa tccccaggag gattagacaa gggctcgagc   3000
tcactctctt gtgagggaca gaaatacaat cagggacagc atatgaatac tccatggaga   3060
aacccagctg aagagggaga aaaattagca tacagaaaac aaaatatgga tgatatagat   3120
gaggaagatg atgacttggt aggggtatca gtgaggccaa aagttctcct aagaacaatg   3180
agttacaaat tggcaataga catgtctcat tttataaaag aaaagggggg actggaaggg   3240
atttattaca gtgcaagaag acatagaatc ttagacatat acttagaaaa ggaagaaggc   3300
atcataccag attggcagga ttacacctca ggaccaggaa ttagataccc aaagacattt   3360
```

```
ggctggctat ggaaattagt ccctgtagat gtatcagatg aggcacagga ggatgaggag   3420

cattacttaa tgcatccagc tcaaacttcc cagtgggatg acccttgggg agaggttcta   3480

gcatggaagt ttgatccaac tctggcctac acttatgagg catatgttag atacccagaa   3540

gagtttggaa gcaagtcagg cctgtcagag gaagaggtta gaagaaggct aaccgcaaga   3600

ggccttctta acatggctga caagaaggaa actcgctgaa acagcaggga ctttccacaa   3660

ggggatgtta cggggaggta ctggggagga gccggtcggg aacgcccact ttcttgatgt   3720

ataaatatca ctgcatttcg ctctgtattc agtcgctctg cggagaggct ggcagattga   3780

gccctgggag gttctctcca gcactagcag gtagagcctg ggtgttccct gctagactct   3840

caccagcact tggccggtgc tgggcagagt gactccacgc ttgcttactt aaagccctct   3900

tcaataaagc tgccatttag aagta                                         3925
```

<210> SEQ ID NO 10
<211> LENGTH: 867
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Met Arg Val Lys Glu Lys Tyr Gln His Leu Trp Arg Trp Gly Trp Arg
1               5                   10                  15

Trp Gly Ile Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Lys Thr Thr Leu Phe Cys Ala Ser Asn Ala Lys Ala Tyr Glu Lys Glu
    50                  55                  60

Val His Asn Ile Trp Ala Thr His Ala Cys Val Pro Thr Asp Pro Asn
65                  70                  75                  80

Pro Gln Glu Ile Val Leu Gly Asn Val Thr Glu Asn Phe Asn Met Trp
                85                  90                  95

Lys Asn Asp Met Val Asp Gln Met His Glu Asp Ile Ile Ser Leu Trp
            100                 105                 110

Asp Gln Ser Leu Lys Pro Cys Val Lys Leu Thr Ser Leu Cys Val Thr
        115                 120                 125

Leu Lys Cys Ser Asn Phe Thr Gly Lys Ser Asn Val Thr Tyr Lys Gly
    130                 135                 140

Asp Met Glu Val Lys Asn Cys Ser Phe Asn Val Thr Thr Glu Ile Arg
145                 150                 155                 160

Asp Lys Lys Gln Lys Val Tyr Ala Leu Phe Tyr Arg Leu Asp Ile Thr
                165                 170                 175

Pro Leu Asp Asp Asn Ser Ser Glu Tyr Ile Leu Ile Asn Cys Asn Ser
            180                 185                 190

Ser Thr Ile Thr Gln Ala Cys Pro Lys Val Asn Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys His Asn Val Ser Thr Val Gln
225                 230                 235                 240

Cys Thr His Gly Ile Lys Pro Val Val Ser Thr Gln Leu Leu Leu Asn
                245                 250                 255
```

-continued

```
Gly Ser Leu Ala Glu Gly Glu Ile Ile Ile Arg Ser Glu Asn Leu Thr
            260                 265                 270

Asp Asn Val Lys Thr Ile Ile Val His Phe Asn Glu Ser Val Glu Ile
        275                 280                 285

Thr Cys Thr Arg Pro Asn Asn Asn Thr Arg Lys Ser Ile Ser Ile Gly
    290                 295                 300

Pro Gly Gln Ala Ile Tyr Ala Thr Gly Asp Ile Ile Gly Asp Ile Arg
305                 310                 315                 320

Gln Ala His Cys Asn Ile Ser Lys Glu Asn Trp Asn Lys Thr Leu Gln
                325                 330                 335

Trp Val Arg Gly Lys Leu Lys Glu His Phe Pro Asn Lys Thr Ile Val
            340                 345                 350

Phe Lys Pro Ser Ser Gly Gly Asp Leu Glu Ile Thr Thr His Ser Phe
        355                 360                 365

Asn Cys Arg Gly Glu Phe Phe Tyr Cys Asn Thr Ser Lys Leu Phe Asn
    370                 375                 380

Ser Thr Asp Asn Ser Thr His Met Gly Thr Glu Asn Asn Thr Ile Ile
385                 390                 395                 400

Thr Ile Pro Cys Arg Ile Lys Gln Ile Ile Asn Met Trp Gln Glu Val
                405                 410                 415

Gly Arg Ala Met Tyr Ala Pro Pro Ile Glu Gly Asn Ile Thr Cys Lys
            420                 425                 430

Ser Asn Ile Thr Gly Leu Leu Leu Val Arg Asp Gly Gly Trp Asp Asn
        435                 440                 445

Ser Thr Asn Asp Thr Glu Thr Phe Arg Pro Gly Gly Gly Asp Met Arg
    450                 455                 460

Asp Asn Trp Arg Ser Glu Leu Tyr Lys Tyr Lys Val Val Glu Val Lys
465                 470                 475                 480

Pro Leu Gly Ile Ala Pro Thr Lys Ala Lys Arg Arg Val Val Glu Arg
                485                 490                 495

Glu Lys Arg Ala Val Gly Ile Gly Ala Val Phe Leu Gly Phe Leu Gly
            500                 505                 510

Ala Ala Gly Ser Thr Met Gly Ala Ala Ser Ile Thr Leu Thr Val Gln
        515                 520                 525

Ala Arg Gln Leu Leu Ser Gly Ile Val Gln Gln Gln Asp Asn Leu Leu
    530                 535                 540

Arg Ala Ile Glu Ala Gln Gln His Met Leu Gln Leu Thr Val Trp Gly
545                 550                 555                 560

Ile Lys Gln Leu Gln Ala Arg Val Leu Ala Ile Glu Arg Tyr Leu Gln
                565                 570                 575

Asp Gln Gln Leu Leu Gly Ile Trp Gly Cys Ser Gly Lys Leu Ile Cys
            580                 585                 590

Thr Thr Ala Val Pro Trp Asn Asp Ser Trp Ser Asn Lys Ser Gln Thr
        595                 600                 605

Asp Ile Trp Glu Asn Met Thr Trp Met Gln Trp Asp Arg Glu Ile Ser
    610                 615                 620

Arg His Thr Asp Thr Ile Tyr Arg Leu Leu Glu Asp Ser Gln Asn Gln
625                 630                 635                 640

Gln Glu Lys Asn Glu Lys Asp Leu Leu Ala Leu Asp Ser Trp Lys Asn
                645                 650                 655

Leu Trp Asn Trp Phe Ser Ile Thr Arg Trp Leu Trp Tyr Ile Lys Ile
            660                 665                 670

Phe Ile Met Ile Val Gly Gly Leu Ile Gly Leu Arg Ile Ile Phe Ala
        675                 680                 685
```

Val Leu Ser Ile Val Asn Arg Val Arg Gln Gly Tyr Ser Pro Leu Ser
690 695 700

Phe Gln Thr His Leu Pro Leu Pro Arg Gly Ala Asp Arg Pro Glu Gly
705 710 715 720

Ile Glu Glu Glu Gly Gly Glu Arg Asp Arg Asp Arg Ser Ile Arg Leu
725 730 735

Val Thr Gly Ser Leu Ala Leu Ile Trp Asp Asp Leu Arg Ser Leu Cys
740 745 750

Leu Phe Ser Tyr His Arg Leu Arg Asp Leu Leu Leu Ile Val Thr Arg
755 760 765

Thr Val Glu Leu Leu Gly Arg Arg Gly Trp Glu Ala Leu Lys Tyr Trp
770 775 780

Trp Asn Leu Leu Leu Tyr Trp Ser Gln Glu Leu Lys Asn Ser Ala Val
785 790 795 800

Ser Leu Leu Asn Ala Thr Ala Ile Ala Val Arg Gln Tyr Gly Trp Ser
805 810 815

Tyr Phe His Glu Ala Val Gln Ala Val Trp Arg Ser Ala Thr Glu Thr
820 825 830

Leu Ala Gly Ala Trp Gly Asp Leu Trp Glu Ile Leu Arg Arg Gly Gly
835 840 845

Arg Trp Ile Leu Ala Ile Pro Arg Arg Ile Arg Gln Gly Leu Glu Leu
850 855 860

Thr Leu Leu
865

<210> SEQ ID NO 11
<211> LENGTH: 263
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 11

Met Gly Gly Ala Ile Ser Met Arg Arg Ser Arg Pro Ser Gly Asp Leu
1 5 10 15

Arg Gln Arg Leu Leu Arg Ala Arg Gly Glu Thr Tyr Gly Arg Phe Leu
20 25 30

Gly Glu Val Glu Asp Gly Tyr Ser Gln Ser Pro Gly Gly Leu Asp Lys
35 40 45

Gly Ser Ser Ser Leu Ser Cys Glu Gly Gln Lys Tyr Asn Gln Gly Gln
50 55 60

His Met Asn Thr Pro Trp Arg Asn Pro Ala Glu Glu Gly Glu Lys Leu
65 70 75 80

Ala Tyr Arg Lys Gln Asn Met Asp Asp Ile Asp Glu Glu Asp Asp Asp
85 90 95

Leu Val Gly Val Ser Val Arg Pro Lys Val Leu Leu Arg Thr Met Ser
100 105 110

Tyr Lys Leu Ala Ile Asp Met Ser His Phe Ile Lys Glu Lys Gly Gly
115 120 125

Leu Glu Gly Ile Tyr Tyr Ser Ala Arg Arg His Arg Ile Leu Asp Ile
130 135 140

Tyr Leu Glu Lys Glu Glu Gly Ile Ile Pro Asp Trp Gln Asp Tyr Thr
145 150 155 160

Ser Gly Pro Gly Ile Arg Tyr Pro Lys Thr Phe Gly Trp Leu Trp Lys
165 170 175

Leu Val Pro Val Asp Val Ser Asp Glu Ala Gln Glu Asp Glu Glu His
180 185 190

Tyr Leu Met His Pro Ala Gln Thr Ser Gln Trp Asp Asp Pro Trp Gly
195 200 205

Glu Val Leu Ala Trp Lys Phe Asp Pro Thr Leu Ala Tyr Thr Tyr Glu
210 215 220

Ala Tyr Val Arg Tyr Pro Glu Glu Phe Gly Ser Lys Ser Gly Leu Ser
225 230 235 240

Glu Glu Glu Val Arg Arg Arg Leu Thr Ala Arg Gly Leu Leu Asn Met
245 250 255

Ala Asp Lys Lys Glu Thr Arg
260

<210> SEQ ID NO 12
<211> LENGTH: 597
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Met Arg Val Trp Trp Trp Gly Leu Gly Leu Met Ile Leu Trp Val Thr
1 5 10 15

Val Tyr Tyr Gly Val Pro Val Trp Lys Glu Ala Lys Thr Thr Leu Phe
20 25 30

Cys Ala Ser Asp Ala Lys Ala Tyr Glu Glu Val His Asn Ile Trp Ala
35 40 45

Thr His Ala Cys Val Pro Thr Asp Pro Asn Pro Gln Glu Val Leu Glu
50 55 60

Asn Val Thr Glu Asn Phe Asn Met Trp Asp Met Val Asp Gln Met His
65 70 75 80

Glu Asp Ile Ile Ser Leu Trp Asp Gln Ser Leu Lys Pro Cys Val Ala
85 90 95

Cys Pro Lys Val Asn Phe Asp Pro Ile Pro Ile His Tyr Cys Ala Pro
100 105 110

Ala Gly Tyr Ala Ile Leu Lys Cys Asn Asn Lys Thr Phe Asn Gly Gly
115 120 125

Pro Cys Asn Val Ser Thr Val Gln Cys Thr His Gly Ile Lys Pro Val
130 135 140

Val Ser Thr Gln Leu Leu Leu Asn Gly Ser Leu Ala Glu Ile Ile Ile
145 150 155 160

Arg Ser Glu Asn Leu Thr Asn Val Lys Thr Ile Ile Val His Val Ile
165 170 175

Cys Thr Gly Gly Ala His Cys Asn Ile Ser Trp Asn Thr Leu Gln Val
180 185 190

Lys Leu Glu His Phe Pro Asn Thr Val Phe Lys Pro Ser Ser Gly Gly
195 200 205

Asp Leu Glu Ile Thr Thr His Ser Phe Asn Cys Arg Gly Glu Phe Phe
210 215 220

Tyr Cys Asn Pro Cys Ile Lys Gln Ile Ile Asn Met Trp Gln Val Gly
225 230 235 240

Arg Ala Met Tyr Ala Pro Pro Ile Gly Asn Ile Thr Cys Lys Ser Asn
245 250 255

Ile Thr Gly Leu Leu Leu Arg Asp Gly Gly Asn Thr Glu Phe Arg Pro
260 265 270

```
Gly Gly Gly Asp Met Arg Asn Trp Arg Ser Glu Leu Tyr Lys Tyr Lys
        275                 280                 285

Val Val Ile Pro Leu Gly Ile Ala Pro Thr Lys Ala Lys Arg Lys Val
    290                 295                 300

Val Glu Arg Lys Arg Ala Val Gly Ile Gly Ala Phe Leu Gly Phe Leu
305                 310                 315                 320

Gly Ala Ala Gly Ser Thr Met Gly Ala Ala Ser Thr Leu Thr Val Gln
                325                 330                 335

Ala Arg Gln Leu Leu Ser Gly Ile Val Gln Gln Gln Asn Leu Leu Arg
            340                 345                 350

Ala Ile Glu Ala Gln Gln His Met Leu Gln Leu Thr Val Trp Gly Ile
        355                 360                 365

Lys Gln Leu Gln Ala Arg Val Leu Ala Ile Glu Arg Tyr Leu Gln Asp
    370                 375                 380

Gln Gln Leu Leu Gly Ile Trp Gly Cys Ser Gly Lys Leu Ile Cys Thr
385                 390                 395                 400

Thr Val Pro Trp Asn Ser Trp Ser Lys Ser Asp Ile Trp Asn Met Thr
                405                 410                 415

Trp Met Gln Trp Asp Lys Glu Ile Thr Thr Ile Tyr Leu Leu Asp Ser
            420                 425                 430

Gln Gln Gln Glu Lys Asn Glu Lys Leu Leu Ala Leu Asp Ser Trp Asn
        435                 440                 445

Leu Trp Asn Trp Phe Ile Thr Trp Leu Trp Tyr Ile Lys Ile Phe Ile
    450                 455                 460

Met Ile Val Gly Gly Leu Ile Gly Leu Arg Ile Ile Phe Ala Val Leu
465                 470                 475                 480

Ser Val Arg Val Arg Gln Gly Tyr Ser Pro Leu Ser Phe Gln Thr Pro
                485                 490                 495

Pro Arg Gly Pro Asp Arg Ile Glu Glu Glu Gly Gly Glu Asp Arg Asp
            500                 505                 510

Arg Ser Ile Arg Leu Val Gly Leu Ala Leu Trp Asp Asp Leu Arg Ser
        515                 520                 525

Leu Cys Leu Phe Ser Tyr His Arg Leu Arg Asp Leu Ile Val Arg Glu
    530                 535                 540

Leu Leu Gly Arg Gly Trp Glu Ala Leu Lys Tyr Leu Gln Tyr Trp Glu
545                 550                 555                 560

Leu Lys Ser Ala Val Ser Leu Leu Thr Ala Ile Ala Val Ala Glu Gly
                565                 570                 575

Thr Asp Arg Val Ile Glu Val Gln Cys Arg Ala Ile Ile Pro Arg Arg
            580                 585                 590

Arg Gln Gly Glu Leu
        595
```

<210> SEQ ID NO 13
<211> LENGTH: 839
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Arg Val Arg Gly Ile Gln Arg Asn Tyr Pro Gln Trp Trp Ile Trp
1               5                   10                  15

Gly Ile Leu Gly Phe Leu Met Ile Tyr Asn Gly Met Gly Ser Leu Trp
            20                  25                  30
```

-continued

```
Val Thr Val Tyr Tyr Gly Val Pro Val Trp Lys Glu Ala Lys Thr Thr
        35                  40                  45

Leu Phe Cys Ala Ser Asp Ala Lys Ala Tyr Glu Arg Glu Val His Asn
    50                  55                  60

Ile Trp Ala Thr His Ala Cys Val Pro Thr Asp Pro Asn Pro Gln Glu
65                  70                  75                  80

Leu Val Leu Glu Asn Val Thr Glu Asn Phe Asn Met Trp Glu Asn Asp
                85                  90                  95

Met Val Asp Gln Met His Glu Asp Ile Ile Ser Leu Trp Asp Gln Ser
            100                 105                 110

Leu Lys Pro Cys Val Lys Leu Thr Pro Leu Cys Val Thr Leu Asn Cys
        115                 120                 125

Thr Asp Val Lys Ser Ala Asn Ser Thr Ser Glu Asp Met Arg Asn Cys
    130                 135                 140

Ser Phe Asn Val Thr Thr Glu Ile Lys Asp Arg Lys Lys Leu Glu Gln
145                 150                 155                 160

Ala Leu Phe Tyr Arg Leu Asp Ile Val Pro Leu Lys Asn Ser Ser Ser
                165                 170                 175

Ser Asn Phe Ser Glu Tyr Arg Leu Ile Asn Cys Asn Thr Ser Thr Val
            180                 185                 190

Ser Gln Ala Cys Pro Lys Val Asn Phe Asp Pro Ile Pro Ile His Tyr
        195                 200                 205

Cys Ala Pro Ala Gly Tyr Ala Ile Leu Lys Cys Asn Asn Lys Thr Phe
    210                 215                 220

Asn Gly Ser Gly Pro Cys Asn Asn Val Ser Thr Val Gln Cys Thr His
225                 230                 235                 240

Gly Ile Lys Pro Val Val Ser Thr Gln Leu Leu Leu Asn Gly Ser Leu
                245                 250                 255

Ala Glu Glu Asp Ile Ile Ile Arg Ser Glu Asn Leu Thr Asn Asn Val
            260                 265                 270

Lys Thr Ile Ile Val His Leu Lys Asp Tyr Val Lys Ile Val Cys Thr
        275                 280                 285

Arg Pro Asn Asn Asn Thr Arg Lys Ser Met Arg Ile Gly Pro Gly Gln
    290                 295                 300

Ala Phe Tyr Ala Thr Gly Glu Ile Ile Gly Asn Ile Arg Glu Ala His
305                 310                 315                 320

Cys Asn Ile Ser Gly Ser Lys Trp Asn Asn Thr Leu Gln Arg Val Lys
                325                 330                 335

Lys Lys Leu Gly Glu His Phe Pro Asn Asn Thr Thr Val Asp Phe Lys
            340                 345                 350

Pro Ser Ser Gly Gly Asp Leu Glu Ile Thr Thr His Ser Phe Asn Cys
        355                 360                 365

Arg Gly Glu Phe Phe Tyr Cys Asn Thr Ser Lys Leu Phe Asn Gly Thr
    370                 375                 380

Ser Glu Ser Asn Ser Thr Ile Thr Leu Pro Cys Lys Ile Lys Gln Ile
385                 390                 395                 400

Ile Asn Met Trp Gln Gly Val Gly Arg Ala Met Tyr Ala Pro Pro Ile
                405                 410                 415

Ala Gly Asn Ile Thr Cys Lys Ser Asn Ile Thr Gly Leu Leu Leu Thr
            420                 425                 430

Arg Asp Gly Gly Asn Gly Asn Gly Thr Glu Ile Phe Arg Pro Gly Gly
        435                 440                 445

Gly Asp Met Arg Asp Asn Trp Arg Ser Glu Leu Tyr Lys Tyr Lys Val
```

```
    450                 455                 460

Val Lys Ile Glu Pro Leu Gly Ile Ala Pro Thr Lys Ala Lys Arg Arg
465                 470                 475                 480

Val Val Arg Arg Gly Lys Arg Ala Val Gly Ile Gly Ala Leu Phe Leu
                485                 490                 495

Gly Phe Leu Gly Ala Ala Gly Ser Thr Met Gly Ala Ala Ser Leu Thr
            500                 505                 510

Leu Thr Val Gln Ala Arg Gln Leu Leu Ser Gly Ile Val Gln Gln Gln
        515                 520                 525

Asn Asn Leu Leu Arg Ala Ile Glu Ala Gln Gln His Met Leu Gln Leu
    530                 535                 540

Thr Val Trp Gly Ile Lys Gln Leu Gln Ala Arg Val Leu Ala Ile Glu
545                 550                 555                 560

Arg Tyr Leu Gln Asp Gln Gln Leu Leu Gly Ile Trp Gly Cys Ser Gly
                565                 570                 575

Lys Leu Ile Cys Thr Thr Asp Val Pro Trp Asn Ser Ser Trp Ser Ser
            580                 585                 590

Lys Ser Tyr Glu Asp Ile Trp Thr Asn Met Thr Trp Met Gln Trp Asp
        595                 600                 605

Lys Glu Ile Asn Asn Tyr Thr Asn Thr Ile Tyr Gln Leu Leu Val Asp
    610                 615                 620

Ser Gln Thr Gln Gln Glu Lys Asn Glu Lys Glu Leu Leu Ala Leu Asp
625                 630                 635                 640

Ser Trp Lys Asn Leu Trp Asn Trp Phe Asn Ile Thr Asn Trp Leu Trp
                645                 650                 655

Tyr Ile Lys Ile Phe Ile Met Ile Val Gly Gly Leu Ile Gly Leu Arg
            660                 665                 670

Ile Ile Phe Ala Val Leu Ser Met Val Asn Arg Val Arg Gln Gly Tyr
        675                 680                 685

Ser Pro Leu Ser Phe Gln Thr Leu Thr Pro Asn Pro Arg Gly Pro Asp
    690                 695                 700

Arg Leu Gly Arg Ile Glu Glu Glu Gly Gly Glu Gln Asp Arg Asp Arg
705                 710                 715                 720

Ser Ile Arg Leu Val Ser Gly Phe Leu Ala Leu Ala Trp Asp Asp Leu
                725                 730                 735

Arg Ser Leu Cys Leu Phe Ser Tyr His Arg Leu Arg Asp Cys Ile Leu
            740                 745                 750

Ile Val Ala Arg Ala Ala Glu Leu Leu Gly Arg Ser Ser Leu Arg Gly
        755                 760                 765

Leu Gln Lys Gly Trp Glu Ala Leu Lys Tyr Leu Gly Ser Leu Val Gln
    770                 775                 780

Tyr Trp Gly Leu Glu Leu Lys Lys Ser Ala Val Ser Leu Leu Asp Thr
785                 790                 795                 800

Thr Ala Thr Ala Val Ala Glu Gly Thr Asp Arg Val Ile Glu Leu Val
                805                 810                 815

Gln Arg Ile Cys Arg Ala Ile Cys Asn Ile Pro Arg Arg Ile Arg Gln
            820                 825                 830

Gly Phe Glu Ala Ala Leu Gln
        835
```

<210> SEQ ID NO 14
<211> LENGTH: 1727
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 14

```
caggagcgag cgctcggtgg cgatgcccac gggcctgacg cgtgtggcga cctcccagcc     60
aaatcccacg cacggagtgc tacgcgacca cccgcaacct cccgcctgcc ccaaggtgaa    120
cttcgacccc atccccatcc actactgcgc ccccgccggc tacgccatcc tgaagtgcaa    180
caacaagacc ttcaacggcc cggcccctgc acaacgtgtc caccgtgcag tgcacccacg    240
gcatcaagcc cgtggtgtcc acccagctgc tgctgaacgg ctccctggcc gaggaatcat    300
catccgctcc gagaacctga ccacaacgtg aagaccatca tcgtgcacta agatcgtgag    360
atctgcaccg ccccgcccac tgcaacatct ccaatggaac aaaccctgca gggtgaagct    420
gggagcactt ccccaacaaa ccatcgttca agccctcctc cggcggcgac ctggagatca    480
ccacccactc cttcaactgc cgcggcgagt tcttctactg caaccccccc tgcatcaagc    540
agatcatcaa catgtggcag ggtgggcgcg ccatgtacgc cccccccatc gggcaacatc    600
acctgcaagt ccaacatcac cggcctgctg ctgcgcgacg gcggcaccaa ccaccgagac    660
ttccgccccg gcggcggcga catgcgcaca actggcgctc cgagctgtac aagtacaagg    720
tggtgagatc agcccctggg catcgccccc accaaggcca agcgccgcgt ggtggagcgc    780
gaagcgcgcc gtgggcatcg gcgcctgttc ctgggcttcc tgggcgccgc cggctccacc    840
atgggcgccg cctcctaccc tgaccgtgca ggcccgccag ctgctgtccg gcatcgtgca    900
gcagcagaca acctgctgcg cgccatcgag gcccagcagc acatgctgca gctgaccgtg    960
tggggcatca acagctgcag gcccgcgtgc tggccatcga gcgctacctg caggaccagc   1020
agctgctggg catctggggc tgctccggca agctgatctg caccaccgcg tgccctggaa   1080
ccctcctggt cccaagtcca gacatctgga acatgacctg gatgcagtgg gacaaggaga   1140
tccaaacacc acaccatcta ccctgctggg gactcccaga ccagcaggag aagaacgaga   1200
aggactgctg gccctggact cctggagaac ctgtggaact ggttccatca ccaatggctg   1260
tggtacatca agatcttcat catgatcgtg ggcggcctga tcggcctgcg catcatcttc   1320
gccgtgctgt ccatgtgccg cgtgcgccag ggctactccc ccctgtcctt ccagaccccc   1380
cacccccgcg gccccgaccg ccggcatcga ggaggagggc ggcgagcgac cgcgaccgct   1440
ccatccgcct ggtgcggctc ctggccctgc tgggacgacc tgcgctccct gtgcctgttc   1500
tcctaccacc gcctgcgcga ctctgatcgt gcccgccgga gctgctgggc cgccggctgg   1560
gaggccctga agtacggcct gtgcagtact ggccggagct gaagaatccg ccttccctgc   1620
tgacccaccg ccatcgccgt ggccgagggc accgaccgct atcgagtgtc aggcctgccg   1680
cgccatcgca catcccccgc cgcatcgcca gggctgagcc ctgcgta                 1727
```

<210> SEQ ID NO 15
<211> LENGTH: 2520
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15

```
atgcgcgtgc gcggcatcca gcgcaactac ccccagtggt ggatctgggg catcctgggc     60
ttcctgatga tctacaacgg catgggctcc ctgtgggtga ccgtgtacta cggcgtgccc    120
gtgtggaagg aggccaagac caccctgttc tgcgcctccg acgccaaggc ctacgagcgc    180
```

-continued

```
gaggtgcaca acatctgggc cacccacgcc tgcgtgccca ccgaccccaa cccccaggag    240
ctggtgctgg agaacgtgac cgagaacttc aacatgtggg agaacgacat ggtggaccag    300
atgcacgagg acatcatctc cctgtgggac cagtccctga agccctgcgt gaagctgacc    360
cccctgtgcg tgaccctgaa ctgcaccgac gtgaagtccg ccaactccac ctccgaggac    420
atgcgcaact gctccttcaa cgtgaccacc gagatcaagg accgcaagaa gctggagcag    480
gccctgttct accgcctgga catcgtgccc ctgaagaact cctcctcctc caacttctcc    540
gagtaccgcc tgatcaactg caacacctcc accgtgtccc aggcctgccc caaggtgaac    600
ttcgacccca tccccatcca ctactgcgcc cccgccggct acgccatcct gaagtgcaac    660
aacaagacct tcaacggctc cggcccctgc aacaacgtgt ccaccgtgca gtgcacccac    720
ggcatcaagc ccgtggtgtc cacccagctg ctgctgaacg gctccctggc cgaggaggac    780
atcatcatcc gctccgagaa cctgaccaac aacgtgaaga ccatcatcgt gcacctgaag    840
gactacgtga agatcgtgtg cacccgcccc aacaacaaca cccgcaagtc catgcgcatc    900
ggccccggcc aggccttcta cgccaccggc gagatcatcg gcaacatccg cgaggcccac    960
tgcaacatct ccggctccaa gtggaacaac accctgcagc gcgtgaagaa gaagctgggc   1020
gagcacttcc ccaacaacac caccatcgac ttcaagccct cctccggcgg cgacctggag   1080
atcaccaccc actccttcaa ctgccgcggc gagttcttct actgcaacac ctccaagctg   1140
ttcaacggca cctccgagtc caactccacc atcaccctgc cctgcaagat caagcagatc   1200
atcaacatgt ggcagggcgt gggccgcgcc atgtacgccc cccccatcgc cggcaacatc   1260
acctgcaagt ccaacatcac cggcctgctg ctgacccgcg acggcggcaa cggcaacggc   1320
accgagatct tccgccccgg cggcggcgac atgcgcgaca actggcgctc cgagctgtac   1380
aagtacaagg tggtgaagat cgagcccctg ggcatcgccc ccaccaaggc caagcgccgc   1440
gtggtggagc gcggcaagcg cgccgtgggc atcggcgccc tgttcctggg cttcctgggc   1500
gccgccggct ccaccatggg cgccgcctcc ctgaccctga ccgtgcaggc ccgccagctg   1560
ctgtccggca tcgtgcagca gcagaacaac ctgctgcgcg ccatcgaggc ccagcagcac   1620
atgctgcagc tgaccgtgtg gggcatcaag cagctgcagg cccgcgtgct ggccatcgag   1680
cgctacctgc aggaccagca gctgctgggc atctggggct gctccggcaa gctgatctgc   1740
accaccgacg tgccctggaa ctcctcctgg tcctccaagt cctacgagga catctggacc   1800
aacatgacct ggatgcagtg ggacaaggag atcaacaact acaccaacac catctaccag   1860
ctgctggtgg actcccagac ccagcaggag aagaacgaga aggagctgct ggccctggac   1920
tcctggaaga acctgtggaa ctggttcaac atcaccaact ggctgtggta catcaagatc   1980
ttcatcatga tcgtgggcgg cctgatcggc ctgcgcatca tcttcgccgt gctgtccatg   2040
gtgaaccgcg tgcgccaggg ctactccccc ctgtccttcc agaccctgac ccccaacccc   2100
cgcggccccg accgcctggg ccgcatcgag gaggagggcg gcgagcagga ccgcgaccgc   2160
tccatccgcc tggtgtccgg cttcctggcc ctggcctggg acgacctgcg ctccctgtgc   2220
ctgttctcct accaccgcct gcgcgactgc atcctgatcg tggcccgcgc cgccgagctg   2280
ctgggccgct cctccctgcg cggcctgcag aagggctggg aggccctgaa gtacctgggc   2340
tccctggtgc agtactgggg cctggagctg aagaagtccg ccatctccct gctggacacc   2400
accgccatcg ccgtggccga gggcaccgac cgcatcatcg agctgatcca gcgcatctgc   2460
cgcgccatct gcaacatccc ccgccgcatc cgccagggct tcgaggccgc cctgcagtaa   2520
```

<210> SEQ ID NO 16

-continued

```
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Gly Ala Ile Ser Met Arg Arg Ser Arg Pro Ser Gly Asp Leu
1               5                   10                  15

Arg Gln Arg Leu Leu Arg Ala Arg Gly Glu Thr Tyr Gly Arg Leu Leu
            20                  25                  30

Gly Glu Val Glu Asp Gly Tyr Ser Gln Ser Pro Gly Gly Leu Asp Lys
        35                  40                  45

Gly Leu Ser Ser Leu Ser Cys Glu Gly Gln Lys Tyr Asn Gln Gly Gln
    50                  55                  60

Tyr Met Asn Thr Pro Trp Arg Asn Pro Ala Glu Glu Arg Glu Lys Leu
65                  70                  75                  80

Ala Tyr Arg Lys Gln Asn Met Asp Asp Ile Asp Glu Glu Asp Asp Asp
                85                  90                  95

Leu Val Gly Val Ser Val Arg Pro Lys Val Pro Leu Arg Thr Met Ser
            100                 105                 110

Tyr Lys Leu Ala Ile Asp Met Ser His Phe Ile Lys Glu Lys Gly Gly
        115                 120                 125

Leu Glu Gly Ile Tyr Tyr Ser Ala Arg Arg His Arg Ile Leu Asp Ile
    130                 135                 140

Tyr Leu Glu Lys Glu Glu Gly Ile Ile Pro Asp Trp Gln Asp Tyr Thr
145                 150                 155                 160

Ser Gly Pro Gly Ile Arg Tyr Pro Lys Thr Phe Gly Trp Leu Trp Lys
                165                 170                 175

Leu Val Pro Val Asn Val Ser Asp Glu Ala Gln Glu Asp Glu Glu His
            180                 185                 190

Tyr Leu Met His Pro Ala Gln Thr Ser Gln Trp Asp Asp Pro Trp Gly
        195                 200                 205

Glu Val Leu Ala Trp Lys Phe Asp Pro Thr Leu Ala Tyr Thr Tyr Glu
    210                 215                 220

Ala Tyr Val Arg Tyr Pro Glu Glu Phe Gly Ser Lys Ser Gly Leu Ser
225                 230                 235                 240

Glu Glu Glu Val Arg Arg Arg Leu Thr Ala Arg Gly Leu Leu Asn Met
                245                 250                 255

Ala Asp Lys Lys Glu Thr Arg
            260
```